(12) United States Patent
Dicosimo et al.

(10) Patent No.: US 8,334,120 B2
(45) Date of Patent: Dec. 18, 2012

(54) PERHYDROLASES FOR ENZYMATIC PERACID GENERATION

(75) Inventors: Robert Dicosimo, Chadds Ford, PA (US); Mark S. Payne, Wilmington, DE (US); Tyler Yin, Saint Paul, MN (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/248,260

(22) Filed: Sep. 29, 2011

(65) Prior Publication Data

US 2012/0016025 A1   Jan. 19, 2012

Related U.S. Application Data

(62) Division of application No. 12/572,094, filed on Oct. 1, 2009, now Pat. No. 8,062,875.

(60) Provisional application No. 61/102,505, filed on Oct. 3, 2008, provisional application No. 61/102,512, filed on Oct. 3, 2008, provisional application No. 61/102,514, filed on Oct. 3, 2008, provisional application No. 61/102,520, filed on Oct. 3, 2008, provisional application No. 61/102,531, filed on Oct. 3, 2008, provisional application No. 61/102,539, filed on Oct. 3, 2008.

(51) Int. Cl.
| | |
|---|---|
| C12P 7/40 | (2006.01) |
| C12N 9/00 | (2006.01) |
| C12N 9/16 | (2006.01) |
| C12N 1/20 | (2006.01) |
| C12N 15/00 | (2006.01) |
| C07H 21/04 | (2006.01) |

(52) U.S. Cl. ..... 435/136; 435/183; 435/196; 435/252.3; 435/320.1; 510/310; 514/557; 536/23.2

(58) Field of Classification Search .................. None
See application file for complete search history.

(56) References Cited

U.S. PATENT DOCUMENTS

| | | |
|---|---|---|
| 3,974,082 A | 8/1976 | Weyn |
| 4,444,886 A | 4/1984 | Esders et al. |
| 4,585,150 A | 4/1986 | Beacham et al. |
| 4,678,103 A | 7/1987 | Dirksing |
| 5,108,457 A | 4/1992 | Poulose et al. |
| 5,116,575 A | 5/1992 | Badertscher et al. |
| 5,152,461 A | 10/1992 | Proctor |
| 5,281,525 A | 1/1994 | Mitsushima et al. |
| 5,296,161 A | 3/1994 | Wiersema et al. |
| 5,338,676 A | 8/1994 | Mitsushima et al. |
| 5,364,554 A | 11/1994 | Stanislowski et al. |
| 5,398,846 A | 3/1995 | Corba et al. |
| 5,528,152 A | 6/1996 | Hinoshita et al. |
| 5,532,157 A | 7/1996 | Fink |
| 5,605,793 A | 2/1997 | Stemmer |
| 5,624,634 A | 4/1997 | Brougham et al. |
| 5,683,724 A | 11/1997 | Hei et al. |
| 5,811,238 A | 9/1998 | Stemmer et al. |
| 5,830,721 A | 11/1998 | Stemmer et al. |
| 5,837,458 A | 11/1998 | Minshull et al. |
| 5,862,949 A | 1/1999 | Markey et al. |
| 5,932,532 A | 8/1999 | Ghosh et al. |
| 5,954,213 A | 9/1999 | Gerhart et al. |
| 6,183,807 B1 | 2/2001 | Gutzmann et al. |
| 6,210,639 B1 | 4/2001 | Vlass et al. |
| 6,223,942 B1 | 5/2001 | Markey et al. |
| 6,319,888 B2 | 11/2001 | Wei et al. |
| 6,391,840 B1 | 5/2002 | Thompson et al. |
| 6,465,233 B1 | 10/2002 | Knauseder et al. |
| 6,518,307 B2 | 2/2003 | McKenzie et al. |
| 6,545,047 B2 | 4/2003 | Gutzmann et al. |
| 6,635,286 B2 | 10/2003 | Hei et al. |
| 6,645,233 B1 | 11/2003 | Ayers et al. |
| 6,758,411 B2 | 7/2004 | Conway et al. |
| 6,995,125 B2 | 2/2006 | Dasque et al. |
| 7,384,787 B2 | 6/2008 | Kazlauskas et al. |
| 7,448,556 B2 | 11/2008 | Muehlhausen et al. |
| 7,550,420 B2 | 6/2009 | DiCosimo et al. |
| 7,612,030 B2 | 11/2009 | DiCosimo et al. |
| 7,723,083 B2 | 5/2010 | DiCosimo et al. |
| 7,964,378 B2 | 6/2011 | Dicosimo et al. |
| 2002/0030063 A1 | 3/2002 | Leray et al. |
| 2004/0127381 A1 | 7/2004 | Scialla et al. |
| 2005/0008526 A1 | 1/2005 | Bianchetti et al. |
| 2008/0176299 A1 | 7/2008 | DiCosimo et al. |
| 2008/0176783 A1 | 7/2008 | DiCosimo et al. |
| 2009/0005590 A1 | 1/2009 | DiCosimo et al. |
| 2009/0305366 A1 | 12/2009 | DiCosimo et al. |
| 2009/0311763 A1 | 12/2009 | DiCosimo et al. |
| 2009/0312420 A1 | 12/2009 | DiCosimo et al. |
| 2009/0325266 A1 | 12/2009 | DiCosimo et al. |
| 2010/0041752 A1 | 2/2010 | DiCosimo et al. |

(Continued)

FOREIGN PATENT DOCUMENTS

CN            101326288 A         12/2008

(Continued)

OTHER PUBLICATIONS

U.S. Appl. No. 11/943,872, filed Jun. 7, 2010, DiCosimo et al.
Abbottet al., Physical Properties and Kinetic Behavior of a Cephalosporin . . . , Appl. Microbiol. 30(3):413-419 (1975).
Belghith, Stabilization of Penicillium Occitanis Cellulases by Sray Drying in Presence . . . , Enzyme and Microbial Tech., 28, pp. 253-258, XP-002558791(2001).
Berman, H.M. et al., The Protein Data Bank. Nucleic Acids Research, 28 pp. 235-242 (2000).

(Continued)

Primary Examiner — Christian Fronda

(57) ABSTRACT

Disclosed herein are variants enzymes that are structurally classified as CE-7 enzymes and have perhydrolysis activity. Also disclosed herein is a process for producing peroxycarboxylic acids from carboxylic acid esters using the aforementioned variant enzymes as well as methods and compositions comprising the variant enzymes. Further, disinfectant formulations comprising the peroxycarboxylic acids produced by the processes described herein are provided.

9 Claims, 3 Drawing Sheets

U.S. PATENT DOCUMENTS

| | | | |
|---|---|---|---|
| 2010/0048448 A1 | 2/2010 | DiCosimo et al. |
| 2010/0086510 A1 | 4/2010 | DiCosimo et al. |
| 2010/0086534 A1 | 4/2010 | DiCosimo et al. |
| 2010/0086535 A1 | 4/2010 | DiCosimo et al. |
| 2010/0086621 A1 | 4/2010 | DiCosimo et al. |
| 2010/0087528 A1 | 4/2010 | DiCosimo et al. |
| 2010/0136639 A1 | 6/2010 | DiCosimo et al. |
| 2010/0152292 A1 | 6/2010 | DiCosimo et al. |
| 2010/0168234 A1 | 7/2010 | DiCosimo et al. |
| 2010/0168235 A1 | 7/2010 | DiCosimo et al. |
| 2010/0168236 A1 | 7/2010 | DiCosimo et al. |
| 2010/0168237 A1 | 7/2010 | DiCosimo et al. |
| 2011/0081693 A1 | 4/2011 | DiCosimo et al. |

FOREIGN PATENT DOCUMENTS

| | | |
|---|---|---|
| CN | 101558161 A | 10/2009 |
| EP | 0807156 B1 | 11/1997 |
| EP | 2121951 A1 | 11/2009 |
| EP | 1960529 B1 | 2/2010 |
| WO | WO96/32149 | 10/1996 |
| WO | WO97/41833 | 11/1997 |
| WO | WO99/03984 | 1/1999 |
| WO | WO00/61713 | 10/2000 |
| WO | WO02/22467 | 3/2002 |
| WO | WO2004/058961 A1 | 7/2004 |
| WO | WO2005/035705 A2 | 4/2005 |
| WO | WO2006/119060 A1 | 11/2006 |
| WO | WO2007/070609 A2 | 6/2007 |
| WO | WO2007/106293 A1 | 9/2007 |
| WO | WO2008/073139 A1 | 6/2008 |
| WO | WO2009/067279 A1 | 5/2009 |

OTHER PUBLICATIONS

H.M. Berman, Announcing the Worldwide Protein Data Bank, Nature Structural Biology 10 (12), p. 980 (2003).

Bernhardt, P., et al., "Molecular basis of perhydrolase activity in serin hyrdolases", Angew. Chemie Int. Ed., vol. 44, pp. 2742-2746 (2005).

Braeken, L. et al., Modeling of the Adsorption of Organic Compounds on Polymeric Nanofiltration Membranes in Solutions Containing . . . , Chem Phys Chem, 6:1606-1612 (2005).

Chenna, R., et al., "Multiple sequence alignment with the clustal series of programs", Nucleic Acids Research, vol. 31, pp. 3497-3500 (2003).

Chica, R.A., et al., "Semi-rational approaches to engineering . . . ", Curr. Opin. Biotechnol., vol. 16, pp. 378-384 (2005).

Copeland, et al., "*Thermotoga lettingae* acetyl xylan esterase", A8F440_THELT, XP002501372, Nov. 13, 2007.

Cardoza et al., A Cephalosporin C Acetylhydrolase is Present in the Cultures of *Nocardia lactamdurans*, Appl. Microbiol. Biotechnol., 54(3):406-412 (2000).

Castillo et al., On the Activity Loss of Hydrolases in Organic Solvents . . . , J. Mol. Catalysis Elsevier, vol. 35, No. 4-6, pp. 147-153, Sep. 1, 2005.

Datsenko, K.A., et al., "One step inactivation of chromosomal genes in *Escherichia coli* K-12 using PCR products", Proc. Natl. Acad. Sci., vol. 97, pp. 6640-6645 (2000).

Degrassi et al., The Acetyl Xyland Esterase of *Bacillus pumilus* Belongs to a Family . . . , Microbiology., 146:1585-1591 (2000).

Deshpande, M.V., "Ethanol production from cellulose . . . " Appl. Biochem. Biotechnol., vol. 36, pp. 227-234 (1992).

DiCosimo, Thermophilic Perhydrolases for Peracetic Acid Production, Sim Annual Meeting and Exhibition, XP0002557717, Jul. 30, 2009.

Fromant et al., Direct Random Mutagenesis of Gene-Sized DNA Fragments Using Polymerase Chain Reaction, Analytical Biochemistry 224, 347-353 (1995).

Funasaki, N. et al., Intramolecular Hydrophobic Association of Two Alkyl Chains of Ollgoethylene Glycol Diethers and Diesters in Water, J. Phys. Chem. 88:5786-5790 (1984).

Gabrielson, J., et al., "Evaluation of redox indicators . . . ", J. Microbiol. Methods, vol. 50, pp. 63-73 (2002).

Gilbert et al., Recent Advances in Carbohydrate Bioengineering, The Royal Society of Chemistry, Cambridge, pp. 3-12. (1999).

Gunning, Y. M. et al., Phase Behavior and Component Partitioning in Low Water Content Amorphous Carbohydrates . . . , J. Agric. Food Chem. 48:395-399 (2000).

Guo, H.H., et al., "Protein tolerance to random amino acid change", Proc. Natl. Acad. Sci., vol. 101, pp. 9205-9210 (2004).

Higgins, D.G., et al., "Fast and sensitive multiple sequence alignments on a microcomputer", Comput. Appl. Biol. Sci., vol. 5, pp. 151-153 (1989).

Ikeda et al., Complete Genome Sequence and Comparative Analysis of the Industrial Microorganism Streptomyces Avermitilis, Nat. Biotechnol. 21 (5), 526-531 (2003).

Justus Liebigs Annalen der Chemie; 105:206 (1858).

Kirk, O., et al., "Enzyme catalyzed degradation and formulation of peroxycarboxylic acids", Biocatalysts, vol. 11, pp. 65-77 (1994).

Kobayashi et al., Purification and Properties of an Alkaline Protease from Alkalophilic *Bacillus* sp. KSM-K16, Appl. Microbiol. Biotechnol. 43 (3), 473-481 (1995).

Krastanova et al., Heterologous Expression, Purificaiton, Crystallization, X-Ray Analysis and . . . , Biochimica ET Biophysica Acta, vol. 1748, No. 2, May 2005, pp. 222-230.

Kunst et al., The Complete Genome Sequence of the Gram-Positive Bacterium *Bacillus subtilis*, Nature 390:249-256 (1997).

Kuo, S-J. et al., Solvent Polarity Influences Product Selectivity of Lipase-Mediated Esterification Reactions in Microaqueous Media, J. Am. Oil Chem. Soc. 73:1427-1433 (1996).

C. Laane et al., Rules for Optimization of Biocatalysis in Organic Solvents, Biotechnol. Bioeng. 30:81-87 (1987).

Lennon, G., et al., "The I.M.A.G.E. Consortium: An integrated molecular analysis of genomes and their expression", Genomics, vol. 33, pp. 151-152 (1996).

Lee, Y.E. et al., Genetic Organization, Sequence and Biochemical Characterization of Recombinant . . . , J Gen Microbiol.,139:1235-1243 (1993).

Lin-Goerke et al., PCR-based Random Mutagenesis Using Manganese and Reduced dNTP Concentration, Biotechniques, 23(3):409-12 (1997).

Lorenz et al., Isolation, Analysis and Expresion of Two Genes from Thermoanaerobacterium . . . , J. Bacteriol 179:5436-5441 (1997).

Minning, M, et al., "Determination of peracid and putative enzymatic peracid formulation by an easy colorimetric assay", Analytica Chimica Acta, vol. 378, pp. 293-298 (1999).

Mitsushima et al Gene Cloning, Nucleotide Sequence, and Expression . . . , Appl. Env. Microbiol. 61(6):2224-2229, (1995).

Melnikov et al., Random Mutagenesis by Recombinational Capture of PCR Products in *Bacillus subtilis* and *Acinetobacter calcoaceticus*, Nucleic Acids Res. 27(4)1056-62 (1999).

Needleman, S.B., et al, "A general method applicable to the search for similarities in the amino acid sequence of two proteins", J. Mol. Biol., vol. 48, pp. 443-453 (1970).

Nelson et al., Evidence for Lateral Gene Transfer Between Archaea and Bacteria From Genome Sequence of *Thermotoga maritime*, Nature, 399:323-329 (1999).

Nixon et al., Assembly of an Active Enzyme by the Linkage of Two Protein Modules, PNAS, 94:1069-1073 (1997).

Oshii et al., Effects of protein on Retention of ADH enzyme Activity Encapsulated . . . , Journal of Food Engr., vol. 87, No. 1, pp. 34-39, Feb. 23, 2008.

Payne, M.S., et al., "Use of alkaline phosphotase fusions to study protein secretion in *Bacillus subtilis*", J. Bacteriol., vol. 173, pp. 2278-2282 (1991).

Pearson, W.R., "Searching protein sequence databases—is optimal best?" Comput. Methods Genome Res., [Proc. Int. Symp.] (1994), Meeting date 1992, pp. 111-120.

Pinkernell, U. et al., Simultaneous HPLC Determination of Peroxyacetic Acid and Hydrogen Peroxide, Anal. Chem., 69(17):3623-3627 (1997).

Rpolitino et al., Purification and Characterization of a Cephalosporin Esterase . . . , Appl. Environ. Microbiol., 63(12):4807-4811 (1997).

Rey et al., Complete Genome Sequence of the Industrial Bacterium *Bacillus licheniformis* and . . . , Genome Biol., 5(10): article 77, R77.1-R77-12, (2004).

Rice, P., et al., "Emboss: the European molecular biology open software suite", Trends Genet., vol. 16, pp. 276-277 (2000).

Ru et al, On the Salt-Induced Activation of Lyophilized Enzyme in Organic Solvents, J. Am. Chem. Soc. vol. 122, No. 8, pp. 1465-1571, Feb. 9, 2000.

Sakai et al., Purification and Properties of Cephalosporing-C Deacetylase from the Yeast . . . , J. Ferment. Bioeng. 85:53-57 (1998).

Seelig, Univ. of Berlin Laboratory; 24: 3466 (1891).

Seffernick, J.L., et al. "Melamine deaminase and atrazine chlorohydrolase: 98 percent identical but functionally different", J. Bacteriol., vol. 183, pp. 2405-2410 (2001).

Serdakowski et al., Enzyme Activation for Organic Solvents Made Easy, Treads in Biotechnology, Trends in Biotechnology, Review, vol. 26, No. 1, pp. 48-54, Nov. 26, 2007.

Siezen et al., Genome-Scale Genotype-Phenotype Matching of Two *Lactococcus lactis* Isolates from Plants Identifies . . . , Appl. Environ. Microbiol. (2008) 74(2): 424-436).

Smith, T.F., et al., "Identification of common molecular subsequences", J. Mol. Biol., vol. 147, pp. 195-197 (1981).

Stöchiometrie und Verwandtschaftslehre vol. 183, [K. Loskit, On the Knowledge of Triglycerides, p. 135-155], vol. 134, Nos. 1 and 2, May 1928.

Sulter, G.J., et al., "Proliferation and metabolic significance . . . ", Arch. Microbiol., vol. 153, pp. 485-489 (1990).

Takami et al., Complete Genome Sequences of the Alkaliphilic Bacterium *Bacillus halodurans* and . . . , NAR, 28(21):4317-4331 (2000).

Tavazza, M., et al., "Nucleotide sequence, genomic organization . . . ", NCBI Gen. ID No. 58632, Apr. 18, 2005, Accession No. CAA44355.

Thompson, J.D., et al., "Clustal W: Improving the sensitivity of progressive . . . " Nucleic Acids Res., vol. 22, pp. 4673-4680 (1994).

Vincent et al., Multifunctional Xylooligosaccharide/Cephalosporin C Deacetylase . . . , J. Mol. Biol., 330:593-606 (2003).

Witkowski, A., et al., "Conversion of a beta-ketoacyl synthase to a malonyl decarboxylase . . . " Biochemistry, vol. 38, pp. 11643-11650 (1999).

Wurtz, Annales de Chimie; 55:443 (1859).

Yernool, D.A., et al., "Molecular and functional characterization . . . " NCBI Gen. ID No. 2429094, Sep. 23, 2002, Accession No. AAB70869.

Corresponding International Search Report and Written Opinion (PCT/ US2009/059230) dated Dec. 22, 2009.

U.S. Appl. No. 12/572,094, Requirement for Restriction/Election, mailed Mar. 31, 2011.

U.S. Appl. No. 12/572,094, Non-Final Rejection, mailed May 16, 2011.

U.S. Appl. No. 12/572,094, Notice of Allowance and Fees Due, mailed Sep. 6, 2011.

Figure 1

```
SEQ ID NO:32    1 MAFFDMPLEELKKYRPERYEEKDFDEFWRETLKESEGFPLDPVFEKVDFH  50
SEQ ID NO:36    1 MAFFDLPLEELKKYRPERYEEKDFDEFWEETLAESEKFPLDPVFERMESH  50
                  *****:********************* *** *** *******::: *

SEQ ID NO:32   51 LKTVETYDVTFSGYRGQRIKGWLLVPKLAEEKLPCVVQYIGYNGGRGFPH 100
SEQ ID NO:36   51 LKTVEAYDVTFSGYRGQRIKGWLLVPKLEEEKLPCVVQYIGYNGGRGFPH 100
                  *****:********************** ********************

SEQ ID NO:32  101 DWLFWPSMGYICFVMDTRGQGSGWMKGDTPDYPEGPVDPQYPGFMTRGIL 150
SEQ ID NO:36  101 DWLFWPSMGYICFVMDTRGQGSGWLKGDTPDYPEGPVDPQYPGFMTRGIL 150
                  ************************:*************************

SEQ ID NO:32  151 DPGTYYYRRVFVDAVRAVEAAISFPRVDSRKVVVAGGSQGGGIALAVSAL 200
SEQ ID NO:36  151 DPRTYYYRRVFTDAVRAVEAAASFPQVDQERIVIAGGSQGGGIALAVSAL 200
                  ** ******** ******** ***:**   ::*:****************

SEQ ID NO:32  201 SNRVKALLCDVPFLCHFRRAVQLVDTHPYVEITNFLKTHRDKEEIVFRTL 250
SEQ ID NO:36  201 SKKAKALLCDVPFLCHFRRAVQLVDTHPYAEITNFLKTHRDKEEIVFRTL 250
                  * : *************************:********************

SEQ ID NO:32  251 SYFDGVNFAARAKVPALFSVGLMDTICPPSTVFAAYNHYAGPKEIRIYPY 300
SEQ ID NO:36  251 SYFDGVNFAARAKIPALFSVGLMDNICPPSTVFAAYNYYAGPKEIRIYPY 300
                  *************:**********:************ ************

SEQ ID NO:32  301 NNHEGGGSFQAIEQVKFLKRLFEEG 325
SEQ ID NO:36  301 NNHEGGGSFQAVEQVKFLKKLFEKG 325
                  ***********:*******:*** *
```

Figure 2a

```
SEQ ID NO:32    MAFFDMPLEELKKYRPERYEEKDFDEFWRETLKESEGFPLDPVFEKVDFHLKTVETYDVT
SEQ ID NO:36    MAFFDLPLEELKKYRPERYEEKDFDEFWEETLAESEKFPLDPVFERMESHLKTVEAYDVT
SEQ ID NO:202   MVYFDMPLEDLRKYLPQRYEEKDFDDFWKQTIHETRGYFQEPILKKVDFYLQNVETFDVT
SEQ ID NO:203   MAFFDLPLEELKKYRPERYEEKDFDEFWECTLAENEKFPLDPVFERMESHLKTVEAYDVT
SEQ ID NO:204   MAFFDLPLEELKKYRPERYEEKDFDEFWKETLAESEKFPLDPVFERMESHLKTVEVYDVT
SEQ ID NO:205   MALFDMPLEKLRSYLPDRYEEEDFDLFWKETLEESRKFPLDPIFERVDYLLENVEVYDVT
                *. **:***.*:.* *:****:*** **,.*: *.. :  :*::::::  *:.**.:***

SEQ ID NO:32    FSGYRGQRIKGWLLVPKLA-EEKLPCVVQYICYNGGRGFPHDWLFWPSMCYICFVMDTRG
SEQ ID NO:36    FSGYRGQRIKGWLLVPKLE-EEKLPCVVQYIGYNGGRGFPHDWLFWPSMGYICFVMDTRG
SEQ ID NO:202   FSGYRGQKIKGWLILPKFR-NGKLPCVVEFVGYGGGRGFPYDWLLWSAAGYAHFIMDTRG
SEQ ID NO:203   FSGYMGQRIKGWLLVPKLE-EEKLPCVVQYIGYNGGRGFPHDWLFWPSMGYICFVMDTRG
SEQ ID NO:204   FSGYRGQRIKGWLLVPKLE-EEKLPCVVQYIGYNGGRGFPHDWLFWPSMGYICFVMDTRG
SEQ ID NO:205   FSGYRGQRIKAWLILPVVKKEERLPCIVEFIGYRGGRGFPFDWLFWSSAGYAHFVMDTRG
                ****  **:**.**::*  _  :  :***:*:::** ******.***:*.: **  *:*****

SEQ ID NO:32    QGSGWMKGDTPDYPEGPVDPQYPGFMTRGILDPGTYYYRRVFVDAVRAVEAAISFPRVDS
SEQ ID NO:36    QGSGWLKGDTPDYPEGPVDPQYPGFMTRGILDPRTYYYRRVFTDAVRAVEAAASFPQVDQ
SEQ ID NO:202   QGSNWMKGDTPDYEDNPSDPQYPGFLTKGVLNPETYYYRRVFMDAFMAVETISQLEQIDS
SEQ ID NO:203   QGSGWMKGDTPDYPEDPVDPQYPGFMTRGILDPRTYYYRRVFTDAVRAVEAAASFPRVDH
SEQ ID NO:204   QGSGWLKGDTPDYPEDPVDPQYPGFMTRGILDPRTYYYRRVFTDAVRAVEAAASFPRVDH
SEQ ID NO:205   QGTSRVKGDTPDYCDEPINPQFPGFMTRGILDPRTYYYRRVFTDAVRAVETASSFPGIDP
                **:..:******* : * :**:***:*:*:*:*:******** **.  ***:  .:  :*

SEQ ID NO:32    RKVVVAGGSQGGGIALAVSALSNRVKALLCDVPFLCHFRRAVQLVDTHPYVEITNFLKTH
SEQ ID NO:36    ERIVIAGGSQGGGIALAVSALSKKAKALLCDVPFLCHFRRAVQLVDTHPYAEITNFLKTH
SEQ ID NO:202   QTILLSGASQGGGIALAVSALSSKVMALLCDVPFLCHYKRAVQITDSMPYAEITRYCKTH
SEQ ID NO:203   ERIVIAGGSQGGGIALAVSALSKKAKALLCDVPFLCHFRRAVQLVDTHPYAEITNFLKTH
SEQ ID NO:204   ERIVIAGGSQGGGIALAVSALSKKAKALLCDVPFLCHFRRAVQLVDTHPYAEITNFLKTH
SEQ ID NO:205   ERIAVVGTSQGGGIALAVAALSEIPKALVSNVPFLCHFRRAVQITDNAPYSEIVNYLKVH
                . : : * **********:***.    **::******::****:.*. ** **..: *.*

SEQ ID NO:32    RDKEEIVFRTLSYFDGVNFAARAKVPALFSVGLMDTICPPSTVFAAYNHYAGPKEIRIYP
SEQ ID NO:36    RDKEEIVFRTLSYFDGVNFAARAKIPALFSVGLMDNICPPSTVFAAYNYYAGPKEIRIYP
SEQ ID NO:202   IDKIQTVFRTLSYFDGVNFAARAKCPALFSVGLMDDICPPSTVFAAYNYYAGEKDIRIYP
```

Figure 2b

```
SEQ ID NO:203    RDKEEIVFRTLSYFDGVNFAVRAKIPALFSVGLMDNICPPSTVFAAYNHYAGPKEIRIYP
SEQ ID NO:204    RDKEEIVFRTLSYFDGVNFAVRAKIPALFSVGLMDNICPPSTVFAAYNHYAGPKEIRIYP
SEQ ID NO:205    RDKEEIVFRTLSYFDGVNFAARAKIPALFSVLMDKTCPPSTVFAAYNHYAGPKEIKVYP
                 **  : *************.*** ******.***    ************:*** *:*:*:**

SEQ ID NO:32     YNNIIEGGGSFQAIEQVKFLKRLFEEG----
SEQ ID NO:36     YNNHEGGGSFQAVEQVKFLKKLFEKG---
SEQ ID NO:202    YNNIIEGGGSFIITLEKLKFVKKTISMRE--
SEQ ID NO:203    YNNHEGGGSFQAIEQVKFLKRLFEKG---
SEQ ID NO:204    YNNIIEGGGSFQAIEQVKFLKRLFEKG---
SEQ ID NO:205    FNEHEGGESFQRMEELRFMKRILKGEFKA
                 :*:**** **: :*:::*:*:  :.
```

PERHYDROLASES FOR ENZYMATIC PERACID GENERATION

CROSS-REFERENCE TO RELATED APPLICATIONS

This application claims the benefit of U.S. Provisional Application Nos. 61/102,505; 61/102,512; 61/102,514; 61/102,520; 61/102,531; and 61/102,539; each filed Oct. 3, 2008, each of which is incorporated by reference herein in their entireties.

FIELD OF THE INVENTION

This invention relates to the field of enzymatic peroxycarboxylic acid synthesis and in situ enzyme catalysis. More specifically, compositions and methods related to variant enzyme catalysts having improved perhydrolysis activity are provided. At least one peroxycarboxylic acid is produced at sufficient concentrations as to be efficacious for the disinfection or sanitization of surfaces, medical instrument sterilization, food processing equipment sterilization, and suitable for use in textile and laundry care applications such as bleaching, destaining, deodorizing, disinfection or sanitization.

BACKGROUND OF THE INVENTION

Peroxycarboxylic acid compositions have been reported to be effective antimicrobial agents. Methods to clean, disinfect, and/or sanitize hard surfaces, meat products, living plant tissues, and medical devices against undesirable microbial growth have been described (e.g., U.S. Pat. No. 6,545,047; U.S. Pat. No. 6,183,807; U.S. Pat. No. 6,518,307; U.S. Pat. No. 5,683,724; and U.S. Patent Application Publication No. 2003/0026846). Peroxycarboxylic acids have also been reported to be useful in preparing bleaching compositions for laundry detergent applications (U.S. Pat. No. 3,974,082; U.S. Pat. No. 5,296,161; and U.S. Pat. No. 5,364,554).

Peroxycarboxylic acids can be prepared by the chemical reaction of a carboxylic acid and hydrogen peroxide (see *Organic Peroxides*, Daniel Swern, ed., Vol. 1, pp 313-516; Wiley Interscience, New York, 1971). The reaction is usually catalyzed by a strong inorganic acid, such as concentrated sulfuric acid. The reaction of hydrogen peroxide with a carboxylic acid is an equilibrium reaction, and the production of peroxycarboxylic acid is favored by the use of an excess concentration of peroxide and/or carboxylic acid, or by the removal of water.

Some peroxycarboxylic acid-based disinfectants or bleaching agents are comprised of an equilibrium mixture of peroxycarboxylic acid, hydrogen peroxide, and the corresponding carboxylic acid. One disadvantage of these commercial peroxycarboxylic acid cleaning systems is that the peroxycarboxylic acid is oftentimes unstable in solution over time. One way to overcome the stability problem is to generate the peroxycarboxylic acid prior to use by combining multiple reaction components that are individually stable for extended periods of time. Preferably, the individual reaction components are easy to store, relatively safe to handle, and capable of quickly producing an efficacious concentration of peroxycarboxylic acid upon mixing.

The CE-7 family of carbohydrate esterases has recently been reported to have perhydrolase activity. These "perhydrolase" enzymes have been demonstrated to be particularly effective for producing peroxycarboxylic acids from a variety of carboxylic acid ester substrates when combined with a source of peroxygen (See WO2007/070609 and U.S. Patent Application Publication Nos. 2008/0176299, 2008/176783, and 2009/0005590 to DiCosimo et al.; each herein incorporated by reference in their entireties). Some members of the CE-7 family of carbohydrate esterases have been demonstrated to have perhydrolytic activity sufficient to produce 4000-5000 ppm peracetic acid from acetyl esters of alcohols, diols, and glycerols in 1 minute and up to 9000 ppm between 5 minutes and 30 minutes once the reaction components were mixed (DiCosimo et al., U.S. Patent Application Publication No. 2009/0005590).

The ability to commercialize many bleaching and/or disinfection products based on enzymatic perhydrolysis may be dependent upon the cost of producing the enzyme catalyst. The use of enzyme catalysts having improved perhydrolytic activity may reduce the amount of enzyme catalyst in the commercial product and may significantly decrease the cost of production. As such, there remains a need to identify enzyme catalysts having improved perhydrolytic activity.

Further, enzymatic perhydrolysis is typically conducted using aqueous reaction conditions. Enzyme catalysts having perhydrolytic activity typically exhibit hydrolytic activity, forming carboxylic acids that may lower the pH of the reaction mixture. As such, it is desirable to utilize a perhydrolase that has high selectivity for perhydrolysis of an ester to peroxycarboxylic acid relative to hydrolysis of the same ester to carboxylic acid; the "P/H" ratio (rate of perhydrolysis/rate of hydrolysis) is one method of characterizing the selectivity of a perhydrolase for perhydrolysis.

The problem to be solved is to provide enzyme catalysts characterized by improved perhydrolytic activity. The improvement may be an increase in perhydrolase specific activity for carboxylic acid esters and/or an improvement in selectivity for perhydrolysis over hydrolysis when producing peroxycarboxylic acids from carboxylic acid esters.

SUMMARY OF THE INVENTION

The stated problem has been solved by providing enzyme catalysts having improved perhydrolase specific activity and/or improved selectivity for perhydrolysis over hydrolysis when producing peroxycarboxylic acids from carboxylic acid esters. More specifically, CE-7 perhydrolase variants are provided having improved perhydrolase specific activity and/or an improvement in selectivity (i.e., an improvement in the ratio of perhydrolysis/hydrolysis activity). Compositions and processes comprising the present variants are also provided.

One aspect is for an isolated polynucleotide encoding a polypeptide having perhydrolysis activity, said polypeptide being structurally classified as a carbohydrate esterase family 7 enzyme and (a) having at least 95% amino acid sequence identity to SEQ ID NO: 5, SEQ ID NO: 10, SEQ ID NO: 15, SEQ ID NO: 20, or SEQ ID NO: 25, provided that a substitution to amino acid residue 277 of SEQ ID NO: 5, SEQ ID NO: 10, SEQ ID NO: 15, SEQ ID NO: 20, or SEQ ID NO: 25 is selected from the group consisting of serine, threonine, valine, and alanine or (b) having at least 95% amino acid sequence identity to SEQ ID NO: 30, provided that a substitution to amino acid residue 278 of SEQ ID NO: 30 is selected from the group consisting of serine, threonine, valine, and alanine. In some embodiments, the polypeptide comprises SEQ ID NOs: 5, 10, 15, 20, 25, or 30. In some embodiments, the nucleotide sequence comprises SEQ ID NOs: 1, 2, 3, 4, 6, 7, 8, 9, 11, 12, 13, 14, 16, 17, 18, 19, 21, 22, 23, 24, 26, 27, 28, or 29.

Another aspect is for an isolated polypeptide having perhydrolysis activity and being structurally classified as a carbohydrate esterase family 7 enzyme, said polypeptide having at least 95% amino acid sequence identity to (a) SEQ ID NO: 5, SEQ ID NO: 10, SEQ ID NO: 15, SEQ ID NO: 20, or SEQ ID NO: 25, provided that a substitution to amino acid 277 of SEQ ID NO: 5, SEQ ID NO: 10, SEQ ID NO: 15, SEQ ID NO: 20, or SEQ ID NO: 25 is selected from the group consisting of serine, threonine, valine, and alanine; or (b) SEQ ID NO: 30, provided that a substitution to amino acid 278 of SEQ ID NO: 30 is selected from the group consisting of serine, threonine, valine, and alanine. In some embodiments, the polypeptide comprises SEQ ID NOs: 5, 10, 15, 20, 25, or 30.

In a further aspect, a process for producing a peroxycarboxylic acid from a carboxylic acid ester is provided comprising (a) providing a set of reaction components, said components comprising:
(1) a carboxylic acid ester selected from the group consisting of:
(i) one or more esters having the structure $[X]_m R_5$ wherein
X is an ester group of the formula $R_6C(O)O$;
$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;
$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_6$ optionally comprises one or more ether linkages;
m is 1 to the number of carbon atoms in $R_5$,
said one or more esters having solubility in water of at least 5 ppm at 25° C.;
(ii) one or more glycerides having the structure

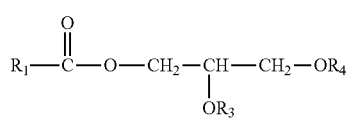

wherein $R_1$ is a C1 to C7 straight chain or branched chain alkyl optionally substituted with an hydroxyl or a C1 to C4 alkoxy group and $R_3$ and $R_4$ are individually H or $R_1C(O)$;
(iii) one or more esters of the formula

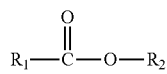

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)$—$O)_nH$ and n is 1 to 10;
(iv) one or more acetylated monosaccharides, acetylated disaccharides, or acetylated polysaccharides; and
(v) any combination of (i) through (iv);

(2) a source of peroxygen; and
(3) the polypeptide having perhydrolysis activity as described above; and (b) combining said reaction components under suitable aqueous reaction conditions whereby a peroxycarboxylic acid is produced.

In an additional aspect, a process is provided to disinfect or sanitize a hard surface or inanimate object using an enzymatically-produced peroxycarboxylic acid composition, said process comprising:

(a) providing a set of reaction components, said components comprising:
(1) a carboxylic acid ester selected from the group consisting of:
(i) one or more esters having the structure $[X]_m R_5$ wherein
X is an ester group of the formula $R_6C(O)O$;
$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;
$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;
m is 1 to the number of carbon atoms in $R_5$,
said one or more esters having solubility in water of at least 5 ppm at 25° C.;
(ii) one or more glycerides having the structure

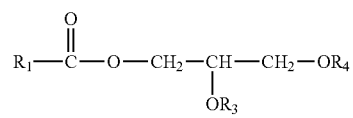

wherein $R_1$ is a C1 to C7 straight chain or branched chain alkyl optionally substituted with an hydroxyl or a C1 to C4 alkoxy group and $R_3$ and $R_4$ are individually H or $R_1C(O)$;
(iii) one or more esters of the formula

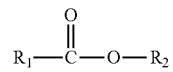

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)$—$O)_nH$ and n is 1 to 10;
(iv) one or more acetylated monosaccharides, acetylated disaccharides, or acetylated polysaccharides; and
(v) any combination of (i) through (iv);
(2) a source of peroxygen; and
(3) the polypeptide having perhydrolysis activity described above;

(b) combining said reaction components under suitable aqueous reaction conditions whereby a peroxycarboxylic acid product is formed;
(c) optionally diluting said peroxycarboxylic acid product; and
(d) contacting said hard surface or inanimate object with the peroxycarboxylic acid produced in step (b) or step (c) whereby said surface or said inanimate object is disinfected.

Another aspect is for a peroxycarboxylic acid generating system comprising:
(a) a substrate selected from the group consisting of:
(i) one or more esters having the structure

wherein
X is an ester group of the formula $R_6C(O)O$;
$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;
$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;
m is 1 to the number of carbon atoms in $R_5$,
said one or more esters having solubility in water of at least 5 ppm at 25° C.;
(ii) one or more glycerides having the structure

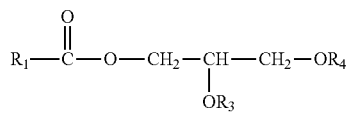

wherein $R_1$ is a C1 to C7 straight chain or branched chain alkyl optionally substituted with an hydroxyl or a C1 to C4 alkoxy group and $R_3$ and $R_4$ are individually H or $R_1C(O)$;
(iii) one or more esters of the formula

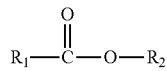

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(C_2CH_2O)_n$, or $(CH_2CH(CH_3)—O)_nH$ and n is 1 to 10;
(iv) one or more acetylated monosaccharides, acetylated disaccharides, or acetylated polysaccharides; and
(v) any combination of (i) through (iv);
(b) a source of peroxygen; and
(c) the polypeptide having perhydrolysis activity described above.

A further aspect is for a process for treating an article of clothing or a textile for bleaching, stain removal, odor reduction, sanitization or disinfection using an enzymatically-produced peroxycarboxylic acid composition, said process comprising:

(a) providing a set of reaction components, said components comprising:
(1) a carboxylic acid ester selected from the group consisting of:
(i) one or more esters having the structure

wherein
X is an ester group of the formula $R_6C(O)O$;
$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;
$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;
m is 1 to the number of carbon atoms in $R_5$,
said one or more esters having a solubility in water of at least 5 ppm at 25° C.;
(ii) one or more glycerides having the structure

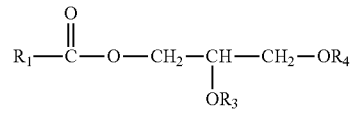

wherein $R_1$ is a C1 to C7 straight chain or branched chain alkyl optionally substituted with an hydroxyl or a C1 to C4 alkoxy group and $R_3$ and $R_4$ are individually H or $R_1C(O)$;
(iii) one or more esters of the formula

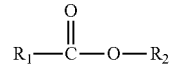

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10;
(iv) one or more acetylated monosaccharides, acetylated disaccharides, or acetylated polysaccharides; and
(v) any combination of (i) through (iv).
(2) a source of peroxygen; and
(3) the polypeptide having perhydrolysis activity described above;
(b) combining said reaction components under suitable aqueous reaction conditions whereby a peroxycarboxylic acid product is formed;
(c) optionally diluting said peroxycarboxylic acid product; and
(d) contacting said article of clothing or textile with the peroxycarboxylic acid produced in step (b) or step (c); wherein said article of clothing or textile is destained, deodorized, disinfected, bleached, or a combination thereof.

In a further aspect, a formulation is provided comprising
(a) a first mixture comprising an enzyme catalyst comprising the polypeptide having perhydrolysis activity described above and a carboxylic acid ester selected from the group consisting of monoacetin, diacetin, triacetin and mixtures thereof; said first mixture optionally comprising a further component selected from the group consisting of an inorganic or organic buffer, a corrosion inhibitor, a wetting agent, and combinations thereof; and (b) a second mixture comprising a source of peroxygen and water, said second mixture optionally further comprising a hydrogen peroxide stabilizer.

In an additional aspect, a formulation is provided comprising (a) a first mixture comprising a enzyme catalyst comprising the polypeptide having perhydrolysis activity described above and an acetylated saccharide selected from the group consisting of acetylated monosaccharides, acetylated disaccharides, acetylated polysaccharides, and combinations thereof, said first mixture optionally further comprising an inorganic or organic buffer, a corrosion inhibitor, and a wetting agent; and (b) a second mixture comprising a source of peroxygen and water, said second mixture optionally comprising a hydrogen peroxide stabilizer.

In another aspect, an isolated polynucleotide encoding a *Thermotoga* acetyl xylan esterase polypeptide having perhydrolysis activity is provided, wherein the polypeptide comprises the C-terminal conserved region of SEQ ID NO: 31, provided that the polypeptide has a substitution to amino acid 93 of SEQ ID NO: 31 selected from the group consisting of serine, threonine, valine, and alanine.

In a further aspect, an isolated *Thermotoga* acetyl xylan esterase polypeptide is provided, wherein said polypeptide having perhydrolysis activity and comprises the C-terminal conserved region of SEQ ID NO: 31, provided that the polypeptide has a substitution to amino acid 93 of SEQ ID NO: 31 selected from the group consisting of serine, threonine, valine, and alanine.

BRIEF DESCRIPTION OF THE FIGURES

FIG. 1 is CLUSTALW sequence comparison between acetyl xylan esterases from *Thermotoga neapolitana* (SEQ ID NO: 32) and *Thermotoga maritima* MSB8 (SEQ ID NO: 36).

FIG. 2 is a CLUSTALW sequence comparison between acetyl xylan esterases from six *Thermotoga* species.

BRIEF DESCRIPTION OF THE BIOLOGICAL SEQUENCES

The following sequences comply with 37 C.F.R. §§1.821-1.825 ("Requirements for patent applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NOs: 1, 2, 3, and 4 are nucleic acid sequences of variant acetyl xylan esterase coding regions derived from the wild-type sequence of an acetyl xylan esterase from *Thermotoga neapolitana*.

SEQ ID NO: 5 represents the deduced amino acid sequence of the acetyl xylan esterase variants derived from the wild-type sequence of an acetyl xylan esterase from *Thermotoga neapolitana*, where the Xaa residue at position 277 is Ala, Val, Ser, or Thr.

SEQ ID NOs: 6, 7, 8, and 9 are nucleic acid sequences of variant acetyl xylan esterase coding regions derived from the wild-type sequence of an acetyl xylan esterase from *Thermotoga maritima* MSB8.

SEQ ID NO: 10 represents the deduced amino acid sequence of the acetyl xylan esterase variants derived from the wild-type sequence of an acetyl xylan esterase from *Thermotoga maritima*, where the Xaa residue at position 277 is Ala, Val, Ser, or Thr.

SEQ ID NOs: 11, 12, 13, and 14 are nucleic acid sequences of variant acetyl xylan esterase coding regions derived from the wild-type sequence of an acetyl xylan esterase from *Thermotoga lettingae*.

SEQ ID NO: 15 represents the deduced amino acid sequence of the acetyl xylan esterase variants derived from the wild-type sequence of an acetyl xylan esterase from *Thermotoga lettingae*, where the Xaa residue at position 277 is Ala, Val, Ser, or Thr.

SEQ ID NOs: 16, 17, 18, and 19 are nucleic acid sequences of variant acetyl xylan esterase coding regions derived from the wild-type sequence of an acetyl xylan esterase from *Thermotoga petrophila*.

SEQ ID NO: 20 represents the deduced amino acid sequences of the acetyl xylan esterase variants derived from the wild-type sequence of an acetyl xylan esterase from *Thermotoga petrophila*, where the Xaa residue at position 277 is Ala, Val, Ser, or Thr.

SEQ ID NOs: 21, 22, 23, and 24 are nucleic acid sequences of one variant acetyl xylan esterase coding regions derived from the wild-type sequence of an acetyl xylan esterase from *Thermotoga* sp. RQ2 described herein as "RQ2(a)".

SEQ ID NO: 25 represents the deduced amino acid sequence of the acetyl xylan esterase variants derived from the wild-type sequence of an acetyl xylan esterase from *Thermotoga* sp. RQ2 described herein as "RQ2(a)", where the Xaa residue at position 277 is Ala, Val, Ser, or Thr.

SEQ ID NOs: 26, 27, 28, and 29 are nucleic acid sequences of a second variant acetyl xylan esterase coding regions derived from *Thermotoga* sp. RQ2.

SEQ ID NO: 30 represents the deduced amino acid sequence of the acetyl xylan esterase variants derived from the wild-type sequence of acetyl xylan esterase from *Thermotoga* sp. RQ2 described herein as "RQ2(b)", where the Xaa residue at position 278 is Ala, Val, Ser, or Thr.

SEQ ID NO: 31 represents a C-terminal conserved region of *Thermotoga acetyl* xylan esterases.

SEQ ID NO: 32 is an acetyl xylan esterase from *Thermotoga neapolitana* (GENBANK® accession #AAB70869).

SEQ ID NOs: 33 and 34 are primers described in Example 1.

SEQ ID NO: 35 is the amplified and codon optimized *Thermotoga neapolitana* nucleic acid product described in Example 1.

SEQ ID NO: 36 is an acetyl xylan esterase from *Thermotoga maritima* (GENBANK® accession #NP_227893.1).

SEQ ID NO: 37 is the amplified *Thermotoga maritima* nucleic acid product described in Example 10.

SEQ ID NOs: 38 and 39 are primers described in Example 10.

SEQ ID NO: 40 is the codon optimized sequence of a *T. neapolitana* acetyl xylan esterase.

SEQ ID NO: 41 is the codon optimized sequence of a *T. maritima* acetyl xylan esterase.

SEQ ID NOs: 42-193 are forward and reverse primers found in Table 1.

SEQ ID NOs: 194-201 are forward and reverse primers found in Table 6.

SEQ ID NO: 202 is the deduced amino acid sequence of a *Thermotoga lettingae* acetyl xylan esterase.

SEQ ID NO: 203 is the deduced amino acid sequence of a *Thermotoga petrophila* acetyl xylan esterase.

SEQ ID NO: 204 is the deduced amino acid sequence of a first acetyl xylan esterase from *Thermotoga* sp. RQ2 described herein as "RQ2(a)".

SEQ ID NO: 205 is the deduced amino acid sequence of a second acetyl xylan esterase from *Thermotoga* sp. RQ2 described herein as "RQ2(b)".

SEQ ID NOs: 206 and 207 are forward and reverse primer as described in Example 10.

SEQ NO: 208 is the nucleic acid sequence of the nucleic acid product amplified by SEQ ID NO: 206 and 207 that was used to prepare plasmid pSW207.

DETAILED DESCRIPTION OF THE INVENTION

Disclosed herein are variant enzymes that are structurally classified as CE-7 enzymes and have perhydrolysis activity. Also disclosed herein is a process for producing peroxycarboxylic acids from carboxylic acid esters using the aforementioned variant enzymes as well as several processes of using the variants in disinfecting and laundry care applications. Further, disinfectant and/or laundry care formulations comprising the peroxycarboxylic acids produced by the processes described herein are provided.

In this disclosure, a number of terms and abbreviations are used. The following definitions apply unless specifically stated otherwise.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the terms "substrate", "suitable substrate", and "carboxylic acid ester substrate" interchangeably refer specifically to:

(a) one or more esters having the structure

wherein

X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;

m is 1 to the number of carbon atoms in $R_5$, said one or more esters having a solubility in water of at least 5 ppm at 25° C.; or (b) one or more glycerides having the structure

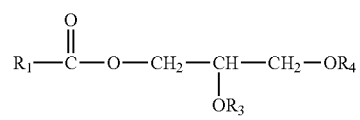

wherein $R_1$ is a C1 to C7 straight chain or branched chain alkyl optionally substituted with an hydroxyl or a C1 to C4 alkoxy group and $R_3$ and $R_4$ are individually H or $R_1C(O)$; or (c) one or more esters of the formula

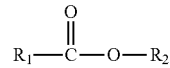

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; or (d) one or more acetylated monosaccharides, acetylated disaccharides, or acetylated polysaccharides; or (e) any combination of (a) through (d).

Examples of said carboxylic acid ester substrate may include monoacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; propylene glycol diacetate; ethylene glycol diacetate; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol; 1,2-hexanediol; 2,5-hexanediol; 1,6-hexanediol; or any combination thereof.

As used herein, the term "peracid" is synonymous with peroxyacid, peroxycarboxylic acid, peroxy acid, percarboxylic acid, and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane; 1,2,3-propanetriol triacetate and all other synonyms of CAS Registry Number 102-76-1.

As used herein, the term "monobutyrin" is synonymous with glycerol monobutyrate, glycerin monobutyrate, and glyceryl monobutyrate.

As used herein, the term "dibutyrin" is synonymous with glycerol dibutyrate and glyceryl dibutyrate.

As used herein, the term "tributyrin" is synonymous with glycerol tributyrate, 1,2,3-tributyrylglycerol, and all other synonyms of CAS Registry Number 60-01-5.

As used herein, the term "monopropionin" is synonymous with glycerol monopropionate, glycerin monopropionate, and glyceryl monopropionate.

As used herein, the term "dipropionin" is synonymous with glycerol dipropionate and glyceryl dipropionate.

As used herein, the term "tripropionin" is synonymous with glyceryl tripropionate, glycerol tripropionate, 1,2,3-tripropionylglycerol, and all other synonyms of CAS Registry Number 139-45-7.

As used herein, the term "ethyl acetate" is synonymous with acetic ether, acetoxyethane, ethyl ethanoate, acetic acid ethyl ester, ethanoic acid ethyl ester, ethyl acetic ester and all other synonyms of CAS Registry Number 141-78-6.

As used herein, the term "ethyl lactate" is synonymous with lactic acid ethyl ester and all other synonyms of CAS Registry Number 97-64-3.

As used herein, the terms "acetylated sugar" and "acetylated saccharide" refer to mono-, di- and polysaccharides comprising at least one acetyl group. Examples include, but are not limited to, glucose pentaacetate; xylose tetraacetate; acetylated xylan; acetylated xylan fragments; β-D-ribofuranose-1,2,3,5-tetraacetate; tri-O-acetyl-D-galactal; and tri-O-acetyl-glucal.

As used herein, the terms "hydrocarbyl", "hydrocarbyl group", and "hydrocarbyl moiety" is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In a preferred embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the terms "monoesters" and "diesters" of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol; 1,2-hexanediol; 2,5-hexanediol; 1,6-hexanediol; and mixtures thereof, refer to said compounds comprising at least one ester group of the formula RC(O)O, wherein R is a C1 to C7 linear hydrocarbyl moiety. In one embodiment, the carboxylic acid ester substrate is selected from the group consisting of propylene glycol diacetate (PGDA), ethylene glycol diacetate (EDGA), and mixtures thereof.

As used herein, the term "propylene glycol diacetate" is synonymous with 1,2-diacetoxypropane, propylene diacetate, 1,2-propanediol diacetate, and all other synonyms of CAS Registry Number 623-84-7.

As used herein, the term "ethylene glycol diacetate" is synonymous with 1,2-diacetoxyethane, ethylene diacetate, glycol diacetate, and all other synonyms of CAS Registry Number 111-55-7.

As used herein, the terms "suitable enzymatic reaction mixture", "components suitable for in situ generation of a peracid", "suitable reaction components", and "suitable aqueous reaction mixture" refer to the materials and water in which the reactants and enzyme catalyst come into contact. The components of the suitable aqueous reaction mixture are provided herein and those skilled in the art appreciate the range of component variations suitable for this process. In one embodiment, the suitable enzymatic reaction mixture produces peroxycarboxylic acid in situ upon combining the reaction components. As such, the reaction components may be provided as a multi-component system wherein one or more of the reaction components remains separated until use. In another embodiment, the reaction components are first combined to form an aqueous solution of peroxycarboxylic acid which is subsequently contacted with the surface to be disinfected and/or bleached. The design of systems and means for separating and combining multiple active components are known in the art and generally will depend upon the physical form of the individual reaction components. For example, multiple active fluids (liquid-liquid) systems typically use multichamber dispenser bottles or two-phase systems (e.g., U.S. Patent Application Publication No. 2005/0139608; U.S. Pat. No. 5,398,846; U.S. Pat. No. 5,624,634; U.S. Pat. No. 6,391,840; E.P. Patent 0807156B1; U.S. Patent Application Publication No. 2005/0008526; and PCT Publication No. WO 00/61713A1) such as found in some bleaching applications wherein the desired bleaching agent is produced upon mixing the reactive fluids. Other forms of multi-component systems used to generate peroxycarboxylic acid may include, but are not limited to those designed for one or more solid components or combinations of solid-liquid components, such as powders (e.g., U.S. Pat. No. 5,116,575), multi-layered tablets (e.g., U.S. Pat. No. 6,210,639), water dissolvable packets having multiple compartments (e.g., U.S. Pat. No. 6,995,125) and solid agglomerates that react upon the addition of water (e.g., U.S. Pat. No. 6,319,888). In one embodiment, a multi-component formulation is provided as two individual components whereby a peroxycarboxylic acid disinfectant is generated upon combining the two components. In another embodiment, a formulation is provided comprising:

a) a first component comprising:
i) an enzyme powder as disclosed herein; and
ii) a carboxylic acid ester substrate, said first component optionally comprising a further ingredient selected from the group consisting of an inorganic or organic buffer, a corrosion inhibitor, a wetting agent, and combinations thereof; and b) a second component comprising a source of peroxygen and water, said second component optionally comprising a hydrogen peroxide stabilizer.

In another embodiment, the carboxylic acid ester in the first mixture is selected from the group consisting of monoacetin, diacetin, triacetin, and combinations thereof. In another embodiment, the carboxylic acid ester in the first mixture is an acetylated saccharide. In another embodiment, the enzyme catalyst in the first mixture is a particulate solid. In another embodiment, the first reaction mixture is a solid tablet or powder.

As used herein, the term "perhydrolysis" is defined as the reaction of a selected substrate with peroxide to form a peroxycarboxylic acid. Typically, inorganic peroxide is reacted with the selected substrate in the presence of a catalyst to produce the peroxycarboxylic acid. As used herein, the term "chemical perhydrolysis" includes perhydrolysis reactions in which a substrate (a peroxycarboxylic acid precursor) is combined with a source of hydrogen peroxide wherein peroxycarboxylic acid is formed in the absence of an enzyme catalyst.

As used herein, the terms "perhydrolase specific activity" or "perhydrolase activity" refer to the catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 μmol of peroxycarboxylic acid product per minute at a specified temperature.

As used herein, the terms "enzyme catalyst" and "perhydrolase catalyst" refer to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (e.g., by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. As described herein, all of the present enzymes having perhydrolysis activity are structurally members of the carbohydrate family esterase family 7 (CE-7 family) of enzymes (see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.). The CE-7 family of enzymes has been demonstrated to be particularly effective for producing peroxycarboxylic acids from a variety of carboxylic acid ester substrates when combined with a source of peroxygen (See PCT publication No. WO2007/070609 and U.S. Patent Application Publication Nos. 2008/0176299, 2008/176783, and 2009/0005590 to DiCosimo et al.; each herein incorporated by reference in their entireties). The CE-7 enzyme family includes cephalosporin C deacetylases (CAHs; E.C. 3.1.1.41) and acetyl xylan esterases (AXEs; E.C. 3.1.1.72). Members of the CE-7 enzyme family share a conserved signature motif (Vincent et al., *J. Mol. Biol.*, 330: 593-606 (2003)).

As used herein, the terms "signature motif", "CE-7 signature motif", and "diagnostic motif" refer to conserved structures shared among a family of enzymes having a defined activity. The signature motif can be used to define and/or identify the family of structurally related enzymes having similar enzymatic activity for a defined family of substrates. The signature motif can be a single contiguous amino acid sequence or a collection of discontiguous, conserved motifs that together form the signature motif. Typically, the conserved motif(s) is represented by an amino acid sequence. The present variant enzymes having perhydrolysis activity ("perhydrolases") belong to the family of CE-7 carbohydrate esterases (i.e., all of the present variants retain the CE-7 signature motif).

As used herein, "structurally classified as a CE-7 enzyme", "structurally classified as a carbohydrate esterase family 7 enzyme", "structurally classified as a CE-7 carbohydrate esterase", and "CE-7 perhydrolase" will be used to refer to enzymes having perhydrolysis activity that are structurally classified as a CE-7 carbohydrate esterase based on the presence of the CE-7 signature motif (Vincent et al., supra). The "signature motif" for CE-7 esterases comprises three conserved motifs (residue position numbering relative to reference sequence SEQ ID NO: 32):

a) Arg118-Gly119-Gln120;
b) Gly179-Xaa180-Ser181-Gln182-Gly183; and
c) His298-Glu299.

Typically, the Xaa at amino acid residue position 180 is glycine, alanine, proline, tryptophan, or threonine. Two of the three amino acid residues belonging to the catalytic triad are in bold. In one embodiment, the Xaa at amino acid residue position 180 is selected from the group consisting of glycine, alanine, proline, tryptophan, and threonine.

Further analysis of the conserved motifs within the CE-7 carbohydrate esterase family indicates the presence of an additional conserved motif (LXD at amino acid positions 267-269 of SEQ ID NO: 32) that may be used to further define a member of the CE-7 carbohydrate esterase family. In a further embodiment, the signature motif defined above includes a fourth conserved motif defined as:

Leu267-Xaa268-Asp269.

The Xaa at amino acid residue position 268 is typically isoleucine, valine, or methionine. The fourth motif includes the aspartic acid residue (bold) belonging to the catalytic triad (Ser181-Asp269-His298).

The conserved motifs found with CE-7 perhydrolases from several wild type *Thermotoga* species.

TABLE A

Conserved motifs found within the enzymes having perhydrolase activity.

| Perhydrolase Sequence | RGQ motif[a] (Residue #s) | GXSQG motif[a] (Residue #s) | LXD motif[b] (Residue #s) | HE motif[a] (Residue #s) |
|---|---|---|---|---|
| SEQ ID NO: 32 | 118-120 | 186-190 | 272-274 | 303-304 |
| SEQ ID NO: 36 | 118-120 | 186-190 | 272-274 | 303-304 |
| SEQ ID NO: 202 | 118-120 | 186-190 | 272-274 | 303-304 |
| SEQ ID NO: 203 | 118-120 | 186-190 | 272-274 | 303-304 |
| SEQ ID NO. 204 | 118-120 | 186-190 | 272-274 | 303-304 |
| SEQ ID NO. 205 | 119-121 | 187-191 | 273-275 | 304-305 |

[a] = Conserved motifs defined by Vincent et al., supra used to define the signature motif.
[b] = an additional motif that may be useful in further defining the signature motif defined by Vincent et al., supra.

As used herein, the terms "cephalosporin C deacetylase" and "cephalosporin C acetyl hydrolase" refer to an enzyme (E.C. 3.1.1.41) that catalyzes the deacetylation of cephalosporins such as cephalosporin C and 7-aminocephalosporanic acid (Mitsushima et al., (1995) *Appl. Env. Microbiol.* 61(6):2224-2229).

As used herein, "acetyl xylan esterases" refers to an enzyme (E.C. 3.1.1.72; AXEs) that catalyzes the deacetylation of acetylated xylans and other acetylated saccharides.

As used herein, the term "*Thermotoga neapolitana*" refers to a strain of *Thermotoga neapolitana* reported to have acetyl xylan esterase activity (GENBANK® AAB70869). The amino acid sequence of the enzyme having perhydrolase activity from *Thermotoga neapolitana* is provided as SEQ ID NO: 32.

As used herein, the term "*Thermotoga maritima*" refers to a bacterial cell reported to have acetyl xylan esterase activity (GENBANK®NP_227893.1). The amino acid sequence of the enzyme having perhydrolase activity from *Thermotoga maritima* is provided as SEQ ID NO: 36.

As used herein, the term "*Thermotoga lettingae*" refers to a bacterial cell reported to have acetyl xylan esterase activity (GENBANK®CP000812). The deduced amino acid sequence of the enzyme having perhydrolase activity from *Thermotoga lettingae* is provided as SEQ ID NO: 202.

As used herein, the term "*Thermotoga petrophila*" refers to a bacterial cell reported to have acetyl xylan esterase activity (GENBANK® CP000702). The deduced amino acid sequence of the enzyme having perhydrolase activity from *Thermotoga lettingae* is provided as SEQ ID NO: 203.

As used herein, the term "*Thermotoga sp. RQ2*" refers to a bacterial cell reported to have acetyl xylan esterase activity (GENBANK® CP000969). Two different acetyl xylan esterases have been identified from *Thermotoga* sp. RQ2 and are referred to herein as "RQ2(a)" (the deduced amino acid sequence provided as SEQ ID NO: 204) and "RQ2(b)" (the deduced amino acid sequence provided as SEQ ID NO: 205).

As used herein, an "isolated nucleic acid molecule" and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |

-continued

| Amino Acid | Three-Letter Abbreviation | One-Letter Abbreviation |
|---|---|---|
| Threonine | Thr | T |
| Tryptophan | Trp | W |
| Tyrosine | Tyr | Y |
| Valine | Val | V |
| Any amino acid or as defined herein | Xaa | X |

As used herein, "substantially similar" refers to nucleic acid molecules wherein changes in one or more nucleotide bases results in the addition, substitution, or deletion of one or more amino acids, but does not affect the functional properties (i.e., perhydrolytic activity) of the protein encoded by the DNA sequence. As used herein, "substantially similar" also refers to an enzyme having an amino acid sequence that is at least 40%, preferably at least 50%, more preferably at least 60%, more preferably at least 70%, even more preferably at least 80%, yet even more preferably at least 90%, and most preferably at least 95% identical to the sequences reported herein wherein the resulting enzyme retains the present functional properties (i.e., perhydrolytic activity). "Substantially similar" may also refer to an enzyme having perhydrolytic activity encoded by nucleic acid molecules that hybridizes under stringent conditions to the nucleic acid molecules reported herein. It is therefore understood that the invention encompasses more than the specific exemplary sequences.

For example, it is well known in the art that alterations in a gene which result in the production of a chemically equivalent amino acid at a given site, but do not affect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, and Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences are encompassed by the present invention. In one embodiment, substantially similar sequences are defined by their ability to hybridize, under stringent conditions (0.1×SSC, 0.1% SDS, 65° C. and washed with 2×SSC, 0.1% SDS followed by 0.1×SSC, 0.1% SDS, 65° C.) with the sequences exemplified herein.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of stringent hybridization conditions is 0.1×SSC, 0.1% SDS, 65° C. and washed with 2×SSC, 0.1% SDS followed by a final wash of 0.1×SSC, 0.1% SDS, 65° C. with the sequences exemplified herein.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6):276-277 (2000)). Multiple alignment of the sequences can be performed using the Clustal method (i.e. CLUSTALW; for example version 1.83) of alignment (Higgins and Sharp, CABIOS, 5:151-153 (1989); Higgins et al., *Nucleic Acids Res.* 22:4673-4680 (1994); and Chenna et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g. Gonnet250), protein END-GAP=−1, Protein GAPDIST=4, and KTUPLE=1. In one embodiment, a fast or slow alignment is used with the default settings where a slow alignment is preferred. Alternatively, the parameters using the CLUSTALW method (version 1.83) may be modified to also use KTUPLE=1, GAP PENALTY=10, GAP extension=1, matrix=BLOSUM (e.g. BLOSUM64), WINDOW=5, and TOP DIAGONALS SAVED=5.

In one aspect of the present invention, suitable isolated nucleic acid molecules (isolated polynucleotides of the present invention) encode a polypeptide having an amino acid sequence that is at least about 50%, preferably at least 60%, more preferably at least 70%, more preferably at least 80%, even more preferably at least 85%, even more preferably at least 90%, and most preferably at least 95% identical to the amino acid sequences reported herein. Suitable nucleic acid molecules of the present invention not only have the above homologies, but also typically encode a polypeptide having about 300 to about 340 amino acids, more preferably about 310 to about 330 amino acids, and most preferably about 325 amino acids.

As used herein, "codon degeneracy" refers to the nature of the genetic code permitting variation of the nucleotide sequence without affecting the amino acid sequence of an encoded polypeptide. Accordingly, the present invention relates to any nucleic acid molecule that encodes all or a substantial portion of the amino acid sequences encoding the present microbial polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, the term "codon optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As used herein, "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene at different stages of development, or in response to different environmental or physiological conditions. Promoters that cause a gene to be expressed at most times are commonly referred to as "constitutive promoters". It is further recognized that since in most cases the exact boundaries of regulatory sequences have not been completely defined, DNA fragments of different lengths may have identical promoter activity.

As used herein, the "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts (normally limited to eukaryotes) to the 3' end of the mRNA precursor.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., that the coding sequence is under the transcriptional control of the promoter. Coding sequences can be operably linked to regulatory sequences in sense or antisense orientation.

As used herein, the term "expression" refers to the transcription and stable accumulation of sense (mRNA) or antisense RNA derived from the nucleic acid molecule of the invention. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal (e.g. plasmid) genes. Host organisms containing the transformed nucleic acid molecules are referred to as "transgenic" or "recombinant" or "transformed" organisms.

As used herein, the terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), CLUSTALW (for example, version 1.83; Thompson et al., *Nucleic Acids Research,* 22(22):4673-4680 (1994), and the FASTA program incorporating the Smith-Waterman algorithm (W. R. Pearson, *Comput. Methods Genome Res., [Proc. Int. Symp.]* (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

As used herein, the term "biological contaminants" refers to one or more unwanted and/or pathogenic biological entities including, but not limited to, microorganisms, spores, viruses, prions, and mixtures thereof. Processes disclosed herein produce an efficacious concentration of at least one percarboxylic acid useful to reduce and/or eliminate the presence of the viable biological contaminants. In a preferred embodiment, the biological contaminant is a viable pathogenic microorganism.

As used herein, the term "disinfect" refers to the process of destruction of or prevention of the growth of biological contaminants. As used herein, the term "disinfectant" refers to an agent that disinfects by destroying, neutralizing, or inhibiting the growth of biological contaminants. Typically, disinfectants are used to treat inanimate objects or surfaces. As used herein, the term "disinfection" refers to the act or process of disinfecting. As used herein, the term "antiseptic" refers to a chemical agent that inhibits the growth of disease-carrying microorganisms. In one aspect, the biological contaminants are pathogenic microorganisms.

As used herein, the term "sanitary" means of or relating to the restoration or preservation of health, typically by removing, preventing or controlling an agent that may be injurious to health. As used herein, the term "sanitize" means to make sanitary. As used herein, the term "sanitize" refers to a sanitizing agent. As used herein the term "sanitization" refers to the act or process of sanitizing.

As used herein, the term "virucide" refers to an agent that inhibits or destroys viruses, and is synonymous with "viricide". An agent that exhibits the ability to inhibit or destroy viruses is described as having "virucidal" activity. Peracids can have virucidal activity. Typical alternative virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peracids can have biocidal activity. Typical alternative biocides known in the art, which may be suitable for use in the present invention include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $log_{10}$ reduction in viable microorganisms after treatment. In one aspect, the targeted reduction in viable microorganisms after treatment is at least a 3-log reduction, more preferably at least a 4-log reduction, and most preferably at least a 5-log reduction. In another aspect, the minimum biocidal concentration is at least a 6-log reduction in viable microbial cells.

As used herein, the terms "peroxygen source" and "source of peroxygen" refer to compounds capable of providing hydrogen peroxide at a concentration of about 1 mM or more when in an aqueous solution including, but not limited to hydrogen peroxide, hydrogen peroxide adducts (e.g., urea-hydrogen peroxide adduct (carbamide peroxide)), perborates, and percarbonates. As described herein, the concentration of the hydrogen peroxide provided by the peroxygen compound in the aqueous reaction formulation is initially at least 1 mM or more upon combining the reaction components. In one embodiment, the hydrogen peroxide concentration in the aqueous reaction formulation is at least 10 mM. In another embodiment, the hydrogen peroxide concentration in the aqueous reaction formulation is at least 100 mM. In another embodiment, the hydrogen peroxide concentration in the aqueous reaction formulation is at least 200 mM. In another embodiment, the hydrogen peroxide concentration in the aqueous reaction formulation is 500 mM or more. In yet another embodiment, the hydrogen peroxide concentration in the aqueous reaction formulation is 1000 mM or more. The molar ratio of the hydrogen peroxide to enzyme substrate, e.g. triglyceride, ($H_2O_2$:substrate) in the aqueous reaction formulation may be from about 0.002 to 20, preferably about 0.1 to 10, and most preferably about 0.5 to 5.

Polypeptide Variants Having Perhydrolysis Activity and being Structurally Classified as CE-7 Enzymes An object of this invention is to provide perhydrolases with improved activity for production of an efficacious concentration of percarboxylic acid for disinfection (e.g., for inactivation of bacteria, viruses, and spores), relative to the wild-type enzymes from which they were derived. A second object of this invention is to provide perhydrolases with improved activity across the entire pH range of activity relative to the wild-type enzymes, where improvement in specific activity results in a decrease in the amount of enzyme required to produce an efficacious concentration of peroxycarboxylic acid (and a concomitant decrease in enzyme cost in a formulation). A third object of the present invention is to provide perhydrolases with an improved perhydrolysis/hydrolysis ratio (P/H ratio) relative to the wild-type enzymes.

The X-ray crystal structure for *T. maritima* CE-7 acetyl xylan esterase has been published (see the Research Collaboratory for Structural Bioinformatics (RCSB) protein databank). The amino acid sequence of *T. neapolitana* CE-7 perhydrolase has 91% identity to the *T. maritima* acetyl xylan esterase, allowing it to be mapped to the *T. maritima* X-ray crystal structure. In addition to the canonical catalytic triad (H303, S188, and D274), several residues are also within the active site of *T. neapolitana*, and substitutions at these sites were chosen to determine if the resulting variant enzymes had beneficial changes in the pKa of the active site, and in the overall $K_{cat}$ and $K_m$ for substrates, and for improvement in the perhydrolysis/hydrolysis ratio (P/H ratio) relative to the wild-type enzymes. Based on the observed perhydrolysis activity, a series of variant CE-7 enzymes having increased peracetic acid generation activity, with respect to the wild-type CE-7 enzymes, were created.

The process of improving perhydrolysis activity involves construction of an expression vector comprising the nucleotide sequence encoding a polypeptide that is structurally classified as a CE-7 enzyme, mutagenesis of the enzyme coding sequence, and finally isolation of variants with increased peracetic acid generation activity. Typically, the approach involves the creating and isolating variant enzymes which increase peracetic acid generation activity in the presence of acetate, triacetin, and hydrogen peroxide. Subsequent rounds of mutagenesis, if desired, allow for evolution of the enzyme-coding sequence.

Mutant enzyme libraries can be prepared using any wild-type (or substantially similar) nucleotide sequence encoding a polypeptide that is structurally classified as a CE-7 enzyme as the starting material for mutagenesis. Methods for mutating sequences are well established in the literature. For example, in vitro mutagenesis and selection, site-directed mutagenesis, error prone PCR (Melnikov et al., *Nucleic Acids Res.* 27(4):1056-62 (1999)), "gene shuffling" or other means can be employed to obtain mutations of enzyme sequences. This could permit production of a polypeptide having, for example, improved activity at an acidic pH for production of a percarboxylic acid for disinfection relative to the wild-type enzyme, improved activity across the entire pH range of activity relative to the wild-type enzymes, and/or improved P/H ratio relative to the wild-type enzyme.

If desired, the regions of an enzyme important for enzymatic activity can be determined through routine site-directed mutagenesis, expression of the resulting variant polypeptides, and determination of their activities. Mutants may include deletions, insertions and point mutations, or combinations thereof.

As discussed in the Examples below, a key cysteine residue has been identified in *Thermotoga* acetyl xylan esterases that, when altered to an alanine, valine, serine, or threonine, unexpectedly increases perhydrolysis activity of the variant polypeptide as compared to the wild-type acetyl xylan esterase lacking the specified amino acid substitution. Because of the high homology between acetyl xylan esterases across the *Thermotoga* genus, it is expected that a substitution of this cysteine with an alanine, valine, serine, or threonine in any *Thermotoga* genus will produce similar results as that described in the working examples. Thus, in some embodiments, the variant polypeptides and the polynucleotides that encode such polypeptides are derived from wild-type *Thermotoga* acetyl xylan esterases having perhydrolysis activity, where the *Thermotoga* acetyl xylan esterase comprises the C-terminal region as set forth in SEQ ID NO: 31, with the variant polypeptide having an alanine, valine, serine, or threonine residue in place of the cysteine residue at amino acid position 93 of SEQ ID NO: 31. The C-terminal region set forth in SEQ ID NO: 31 is highly conserved among *Thermotoga* acetyl xylan esterases (see FIG. 2 for alignment between six acetyl xylan esterases) and thus can serve as an identifier of acetyl xylan esterases that are amenable to mutation of the key cysteine residue disclosed herein.

Even though several residues in SEQ ID NO: 31 are noted as "any" residues, there are typical amino acids that appear at many of these residues. For example, typical amino acids at positions marked Xaa in SEQ ID NO: 31 are glycine at position 2, serine at position 13, lysine at position 18, lysine at position 20, leucine at position 23, cysteine at position 24, aspartic acid at position 25, phenylalanine at position 32, arginine at position 33, leucine at position 38, valine or threonine at position 39, threonine at position 41, histidine at position 42, alanine at position 45, threonine at position 48, asparagine at position 49, phenylalanine or tyrosine at position 50, leucine at position 51, threonine at position 53, arginine at position 55, glutamic acid at position 58, isoleucine at position 60, alanine or valine at position 75, isoleucine at position 79, glycine at position 86, arginine at position 90, isoleucine at position 91, histidine or tyrosine at position 104, praline at position 108, glutamic acid at position 110, arginine at position 112, isoleucine at position 113, tyrosine at position 116, arginine at position 118, glycine at position 123, glutamine at position 126, alanine at position 127, isoleucine at position 128, glutamine at position 130, valine or leucine at position 131, lysine at position 132, leucine at position 134, and arginine or lysine at position 136.

Addition and/or deletion of one or more amino acids in the *Thermotoga* acetyl xylan esterase C-terminal region are permitted so long as such addition(s) and/or deletion(s) does not affect the functional properties of the enzyme.

In more specific embodiments, the variant polypeptides disclosed herein have at least 95% amino acid sequence identity (or, in various embodiments, 96%, 97%, 98%, or 99% sequence identity), based, for example, on the CLUSTAL method of alignment with pairwise alignment default parameters of KTUPLE=1, GAP PENALTY=3, WINDOW=5 and DIAGONALS SAVED=5, when compared to (a) SEQ ID NOs: 5, 10, 15, 20, or 25, provided that a substitution to amino acid 277 of SEQ ID NOs: 5, 10, 15, 20, or 25 is selected from the group consisting of serine, threonine, valine, and alanine; or (b) SEQ ID NO:30, provided that a substitution to amino acid 278 of SEQ ID NO:30 is selected from the group consisting of serine, threonine, valine, and alanine.

Even more specifically, the variant polypeptide having improved perhydrolytic activity (perhydrolytic acitivity and/or an increase in the P/H ratio) comprises SEQ ID NOs: 5, 10, 15, 20, 25, or 30. In another embodiment, the variant polypeptide comprises an amino acid sequence selected from the group consisting of SEQ ID NOs: 5, 10, 15, 20, 25, and 30 wherein Xaa in each respective sequence is selected from the group consisting of alanine, serine, threonine, and valine. In a further embodiment, the variant polypeptide comprises an amino acid sequence selected from the group consisting of SEQ ID NOs: 5 and 10, wherein Xaa in each respective sequence is selected from the group consisting of alanine, serine, threonine, and valine.

Protein Engineering

The present CE-7 esterase variants were produced by mutagenesis. It is contemplated that the present nucleotides may be used to produce gene products having further enhanced or altered activity. Various methods are known for mutating a native gene sequence to produce a gene product with altered or enhanced activity including, but not limited to 1) random mutagenesis, 2) domain swapping (using zinc finger domains or restriction enzymes, 3) error-prone PCR (Melnikov at al., *Nucleic Acids Research* 27(4):1056-1062 (1999)); 4) site directed mutagenesis (Coombs at al., *Proteins* (1998), pp 259-311, 1 plate. Angeletti, Ruth Hogue, Ed., Academic: San Diego, Calif.); and 5) "gene shuffling" (U.S. Pat. Nos. 5,605,793; 5,811,238; 5,830,721; and 5,837,458, incorporated herein by reference).

The polymerase chain reaction (PCR) can be used to amplify a DNA fragment with the concomitant creation of numerous mutations by mis-incorporation of nucleotides. This can be achieved by modifying the PCR conditions such as altering the ratios of dNTPs or adding various amounts of manganese chloride in the reaction (Fromant et al., *Anal Biochem*, 224(1):347-53 (1995); Lin-Goerke et al., *Biotechniques*, 23(3):409-12 (1997)). The pool of mutated DNA fragments can then be cloned to yield a library of mutated plasmids that can then be screened following expression in a host such as *E. coli*.

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions having similarity and/or difference to the gene of interest. This pool of fragments will then be denatured and reannealed to create a mutated gene. The mutated gene is then screened for altered activity.

The instant sequences of the present invention may be mutated and screened for altered or enhanced activity by this method. The sequences should be double-stranded and can be of various lengths ranging from 50 bp to 10 kB. The sequences may be randomly digested into fragments ranging from about 10 bp to 1000 bp, using restriction endonuclease well known in the art (Sambrook, J. and Russell, supra). In addition to the instant microbial sequences, populations of fragments that are hybridizable to all or portions of the sequence may be added. Similarly, a population of fragments, which are not hybridizable to the instant sequence, may also be added. Typically these additional fragment populations are added in about a 10 to 20 fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double-stranded nucleic acid. Preferably the temperature is from about 80° C. to 100° C. The nucleic acid fragments may be reannealed by cooling. Preferably the temperature is from about 20° C. to 75° C. Renaturation may be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTPs (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from about 2 to 50 times, more preferably the sequence is repeated from 10 to 40 times. The resulting nucleic acid is a larger double-stranded polynucleotide ranging from about 50 bp to about 100 kB and may be screened for expression and altered activity by standard cloning and expression protocols (Sambrook, J. and Russell, supra).

Furthermore, a hybrid protein can be assembled by fusion of functional domains using gene shuffling (e.g., Nixon et al., *PNAS*, 94:1069-1073 (1997)). The functional domain of the instant gene may be combined with the functional domain of other genes to create novel enzymes with desired catalytic function. A hybrid enzyme may be constructed using PCR overlap extension methods and cloned into various expression vectors using the techniques well known to those skilled in art.

Suitable Reaction Conditions for the Enzyme-Catalyzed Preparation of Peroxycarboxylic Acids from Carboxylic Acid Esters and Hydrogen Peroxide In one aspect of the invention, a process is provided to produce an aqueous formulation comprising a peroxycarboxylic acid by reacting carboxylic acid esters and a source of peroxygen including, but not limited to, hydrogen peroxide, sodium perborate, and sodium percarbonate, in the presence of at least one of the present enzyme catalysts having perhydrolysis activity. In one embodiment, the present enzyme catalyst comprises at least one of the present enzyme variants having perhydrolytic activity, wherein said enzyme is structurally classified as a member of the CE-7 carbohydrate esterase family.

In another embodiment, the perhydrolase catalyst is a cephalosporin C deacetylase. In another embodiment, the perhydrolase catalyst is an acetyl xylan esterase.

In one embodiment, the perhydrolase catalyst comprises at least one of the present CE-7 variant polypeptides having perhydrolysis activity disclosed herein.

Suitable carboxylic acid ester substrates may include esters provided by the following formula:

$$[X]_m R_5$$

wherein X=an ester group of the formula $R_6C(O)O$
$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for R6=C2 to C7;
$R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;
m=1 to the number of carbon atoms in $R_5$; and
wherein said esters have solubility in water of at least 5 ppm at 25° C.

In other embodiments, suitable substrates may also include esters of the formula:

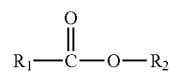

wherein $R_1$=C1 to C7 straight chain or branched chain alkyl optionally substituted with a hydroxyl or a C1 to C4 alkoxy group and $R_2$=C1 to C10 straight chain or branched chain alkyl, alkenyl, alkynyl, aryl, alkylaryl, alkylheteroaryl, heteroaryl, $(CH_2CH_2—O)_nH$ or $(CH_2CH(CH_3)—O)_nH$ and n=1 to In other embodiments, suitable carboxylic acid ester substrates may include glycerides of the formula:

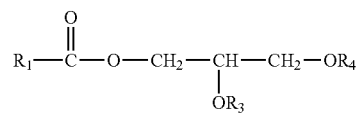

wherein $R_1$=C1 to C7 straight chain or branched chain alkyl optionally substituted with a hydroxyl or a C1 to C4 alkoxy group and $R_3$ and $R_4$ are individually H or $R_1C(O)$.

In other embodiments, $R_6$ is C1 to C7 linear hydrocarbyl moiety, optionally substituted with hydroxyl groups or C1 to C4 alkoxy groups, optionally comprising one or more ether linkages. In further preferred embodiments, $R_6$ is C2 to C7 linear hydrocarbyl moiety, optionally substituted with hydroxyl groups, and/or optionally comprising one or more ether linkages.

In other embodiments, suitable carboxylic acid ester substrates may also include acetylated saccharides selected from the group consisting of acetylated mono-, di-, and polysaccharides. In additional embodiments, the acetylated saccharides include acetylated mono-, di-, and polysaccharides. In further embodiments, the acetylated saccharides are selected from the group consisting of acetylated xylan; fragments of acetylated xylan; acetylated xylose (such as xylose tetraacetate); acetylated glucose (such as glucose pentaacetate); β-D-ribofuranose-1,2,3,5-tetraacetate; tri-O-acetyl-D-galactal; tri-O-acetyl-D-glucal; and acetylated cellulose. In further embodiments, the acetylated saccharide is selected from the group consisting of β-D-ribofuranose-1,2,3,5-tetraacetate; tri-O-acetyl-D-galactal; tri-O-acetyl-D-glucal; and acetylated cellulose. As such, acetylated carbohydrates may be suitable substrates for generating percarboxylic acids using the present methods and systems (i.e., in the presence of a peroxygen source).

In additional embodiments, the carboxylic acid ester substrate is selected from the group consisting of monoacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; propylene glycol diacetate; ethylene glycol diacetate; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol; 1,2-hexanediol; 2,5-hexanediol; 1,6-hexanediol; and mixtures thereof. In preferred embodiments of the present methods and systems, the substrate comprises triacetin.

The carboxylic acid ester is present in the reaction formulation at a concentration sufficient to produce the desired concentration of peroxycarboxylic acid upon enzyme-catalyzed perhydrolysis. The carboxylic acid ester need not be completely soluble in the reaction formulation, but has sufficient solubility to permit conversion of the ester by the perhydrolase catalyst to the corresponding peroxycarboxylic acid. The carboxylic acid ester may be present in the reaction formulation at a concentration of 0.05 wt % to 40 wt % of the reaction formulation, preferably at a concentration of 0.1 wt % to 20 wt % of the reaction formulation, and more preferably at a concentration of 0.5 wt % to 10 wt % of the reaction formulation.

The peroxygen source may include, but is not limited to, hydrogen peroxide, hydrogen peroxide adducts (e.g., urea-hydrogen peroxide adduct (carbamide peroxide)) perborate salts and percarbonate salts. The concentration of peroxygen compound in the reaction formulation may range from 0.0033 wt % to about 50 wt %, preferably from 0.033 wt % to about 40 wt %, more preferably from 0.33 wt % to about 30 wt %.

Many perhydrolase catalysts (whole cells, permeabilized whole cells, and partially purified whole cell extracts) have been reported to have catalase activity (EC 1.11.1.6). Catalases catalyze the conversion of hydrogen peroxide into oxygen and water. In one aspect, the perhydrolysis catalyst lacks catalase activity. In another aspect, a catalase inhibitor is added to the reaction formulation. Examples of catalase inhibitors include, but are not limited to, sodium azide and hydroxylamine sulfate. One of skill in the art can adjust the concentration of catalase inhibitor as needed. In one embodiment, the concentration of the catalase inhibitor ranges from about 0.1 mM to about 1 M; preferably about 1 about mM to about 50 mM; more preferably from about 1 mM to about 20 mM. In one aspect, sodium azide concentration typically ranges from about 20 mM to about 60 mM while hydroxylamine sulfate is concentration is typically about 0.5 mM to about 30 mM, preferably about 10 mM.

In another embodiment, the enzyme catalyst lacks significant catalase activity or is engineered to decrease or eliminate catalase activity. The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis. In a preferred embodiment, the gene(s) encoding the endogenous catalase activity are down-regulated or disrupted (i.e., knocked-out). As used herein, a "disrupted" gene is one where the activity and/or function of the protein encoded by the modified gene is no longer present. Means to disrupt a gene are well-known in the art and may include, but are not limited to insertions, deletions, or mutations to the gene so long as the activity and/or function of the corresponding protein is no longer present. In a further preferred embodiment, the production host is an *E. coli* production host comprising a disrupted catalase gene selected from the group consisting of katG and katE. In another embodiment, the production host is an *E. coli* strain comprising a down-regulation and/or disruption in both katG and a katE catalase genes. An *E. coli* strain comprising a double-knock-out of katG and katE is described herein as *E. coli* strain KLP18 (See Published U.S. Patent Application No. 2008/0176299).

The concentration of the catalyst in the aqueous reaction formulation depends on the specific catalytic activity of the catalyst, and is chosen to obtain the desired rate of reaction. The weight of catalyst in perhydrolysis reactions typically ranges from 0.0001 mg to 10 mg per mL of total reaction volume, preferably from 0.001 mg to 2.0 mg per mL. The catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, and mixtures thereof.

In one aspect, the concentration of peroxycarboxylic acid generated by the combination of chemical perhydrolysis and enzymatic perhydrolysis of the carboxylic acid ester is sufficient to provide an effective concentration of peroxycarboxylic acid for disinfection, bleaching, sanitization, deodoring or destaining at a desired pH. In another aspect, the present methods provide combinations of enzymes and enzyme substrates to produce the desired effective concentration of peroxycarboxylic acid, where, in the absence of added enzyme, there is a significantly lower concentration of peroxycarboxylic acid produced. Although there may in some cases be substantial chemical perhydrolysis of the enzyme substrate by direct chemical reaction of inorganic peroxide with the enzyme substrate, there may not be a sufficient concentration of peroxycarboxylic add generated to provide an effective concentration of peroxycarboxylic acid in the desired applications, and a significant increase in total peroxycarboxylic acid concentration is achieved by the addition of an appropriate perhydrolase catalyst to the reaction formulation.

The concentration of peroxycarboxylic acid generated (such as peracetic acid) by the perhydrolysis of at least one carboxylic acid ester is at least about 20 ppm, preferably at least 100 ppm, more preferably at least about 200 ppm peroxycarboxylic acid, more preferably at least 300 ppm, more preferably at least 500 ppm, more preferably at least 700 ppm, more preferably at least about 1000 ppm peroxycarboxylic acid, more preferably at least 2000 ppm, even more preferably at least 3000 ppm, and most preferably at least 4000 ppm peroxycarboxylic acid within 10 minutes, preferably within 5 minutes, and most preferably within 1 minute of initiating the perhydrolysis reaction (i.e., time measured from combining the reaction components to form the reaction formulation). The product formulation comprising the peroxycarboxylic acid may be optionally diluted with water, or a solution predominantly comprised of water, to produce a formulation with the desired lower concentration of peroxycarboxylic acid. In one aspect, the reaction time required to produce the desired concentration of peroxycarboxylic acid is not greater than about two hours, preferably not greater than about 30 minutes, more preferably not greater than about 10 minutes, and most preferably in about 5 minutes or less. A hard surface or inanimate object contaminated with a concentration of a biological contaminant(s) is contacted with the peroxycarboxylic acid formed in accordance with the processes described herein. In one embodiment, the hard surface or inanimate object is contacted with the peroxycarboxylic acid formed in accordance with the processes described within about 5 minutes to about 168 hours of combining said reaction components, or within about 5 minutes to about 48 hours, or within about 5 minutes to 2 hours of combining said reaction components, or any such time interval therein.

In another aspect, the peroxycarboxylic acid formed in accordance with the processes describe herein is used in a laundry care application wherein the peroxycarboxylic acid is contacted with a textile to provide a benefit, such as disinfecting, bleaching, destaining, deodorizing and/or a combination thereof. The peroxycarboxylic acid may be used in a variety of laundry care products including, but not limited to, textile pre-wash treatments, laundry detergents, stain removers, bleaching compositions, deodorizing compositions, and rinsing agents. In one embodiment, the present process to produce a peroxycarboxylic acid for a target surface is conducted in situ.

In the context of laundry care applications, the term "contacting an article of clothing or textile" means that the article of clothing or textile is exposed to a formulation disclosed herein. To this end, there are a number of formats the formulation may be used to treat articles of clothing or textiles including, but not limited to, liquid, solids, gel, paste, bars, tablets, spray, foam, powder, or granules and can be delivered via hand dosing, unit dosing, dosing from a substrate, spraying and automatic dosing from a laundry washing or drying machine. Granular compositions can also be in compact form; liquid compositions can also be in a concentrated form.

When the formulations disclosed herein are used in a laundry machine, the formulation can further contain components typical to laundry detergents. For example, typical components included, but are not limited to, surfactants, bleaching agents, bleach activators, additional enzymes, suds suppressors, dispersants, lime-soap dispersants, soil suspension and anti-redeposition agents, softening agents, corrosion inhibitors, tarnish inhibitors, germicides, pH adjusting agents, non-builder alkalinity sources, chelating agents, organic and/or inorganic fillers, solvents, hydrotropes, optical brighteners, dyes, and perfumes.

The formulations disclosed herein can also be used as detergent additive products in solid or liquid form. Such additive products are intended to supplement or boost the performance of conventional detergent compositions and can be added at any stage of the cleaning process.

In connection with the present systems and methods for laundry care where the peracid is generated for one or more of bleaching, stain removal, and odor reduction, the concentration of peracid generated (e.g., peracetic acid) by the perhydrolysis of at least one carboxylic acid ester may be at least about 2 ppm, preferably at least 20 ppm, preferably at least 100 ppm, and more preferably at least about 200 ppm peracid. In connection with the present systems and methods for laundry care where the peracid is generated for disinfection or sanitization, the concentration of peracid generated (e.g., peracetic acid) by the perhydrolysis of at least one carboxylic acid ester may be at least about 2 ppm, more preferably at least 20 ppm, more preferably at least 200 ppm, more preferably at least 500 ppm, more preferably at least 700 ppm, more preferably at least about 1000 ppm peracid, most preferably at least 2000 ppm peracid within 10 minutes, preferably within 5 minutes, and most preferably within 1 minute of initiating the perhydrolysis reaction. The product formulation comprising the peracid may be optionally diluted with water, or a solution predominantly comprised of water, to produce a formulation with the desired lower concentration of peracid. In one aspect of the present methods and systems, the reaction time required to produce the desired concentration of peracid is not greater than about two hours, preferably not greater than about 30 minutes, more preferably not greater than about 10 minutes, even more preferably not greater than about 5 minutes, and most preferably in about 1 minute or less.

The temperature of the reaction is chosen to control both the reaction rate and the stability of the enzyme catalyst activity. The temperature of the reaction may range from just above the freezing point of the reaction formulation (approximately 0° C.) to about 95° C., with a preferred range of reaction temperature of from about 5° C. to about 55° C.

The pH of the final reaction formulation containing peroxycarboxylic acid may range from about 2 to about 9, preferably from about 3 to about 8, more preferably from about 5 to about 8, even more preferably about 6 to about 8, and yet even more preferably about 6.5 to about 7.5. In another embodiment, the pH of the reaction formulation may be acidic (pH<7). The pH of the reaction, and of the final reaction formulation, may optionally be controlled by the addition of a suitable buffer, including, but not limited to phosphate, pyrophosphate, methylphosphonate, bicarbonate, acetate, or citrate, and combinations thereof. The concentration of buffer, when employed, is typically from 0.1 mM to 1.0 M, preferably from 1 mM to 300 mM, most preferably from 10 mM to 100 mM.

In another aspect, the enzymatic perhydrolysis reaction formulation may contain an organic solvent that acts as a dispersant to enhance the rate of dissolution of the carboxylic acid ester in the reaction formulation. Such solvents include, but are not limited to, propylene glycol methyl ether, acetone, cyclohexanone, diethylene glycol butyl ether, tripropylene glycol methyl ether, diethylene glycol methyl ether, propylene glycol butyl ether, dipropylene glycol methyl ether, cyclohexanol, benzyl alcohol, isopropanol, ethanol, propylene glycol, and mixtures thereof.

In another aspect, the enzymatic perhydrolysis product may contain additional components that provide desirable functionality. These additional components include, but are not limited to, buffers, detergent builders, thickening agents, emulsifiers, surfactants, wetting agents, corrosion inhibitors (such as benzotriazole), enzyme stabilizers, and peroxide stabilizers (e.g., metal ion chelating agents). Many of the additional components are well known in the detergent industry (see, for example, U.S. Pat. No. 5,932,532; hereby incorporated by reference). Examples of emulsifiers include, but are not limited to, polyvinyl alcohol or polyvinylpyrrolidone. Examples of thickening agents include, but are not limited to, LAPONITE® RD, corn starch, PVP, CARBOWAX®, CARBOPOL®, CABOSIL®, polysorbate 20, PVA, and lecithin. Examples of buffering systems include, but are not limited to sodium phosphate monobasic/sodium phosphate dibasic; sulfamic acid/triethanolamine; citric acid/triethanolamine; tartaric acid/triethanolamine; succinic acid/triethanolamine; and acetic acid/triethanolamine. Examples of surfactants include, but are not limited to a) non-ionic surfactants such as block copolymers of ethylene oxide or propylene oxide, ethoxylated or propoxylated linear and branched primary and secondary alcohols, and aliphatic phosphine oxides; b) cationic surfactants such as quaternary ammonium compounds, particularly quaternary ammonium compounds having a C8-C20 alkyl group bound to a nitrogen atom additionally bound to three C1-C2 alkyl groups; c) anionic surfactants such as alkane carboxylic acids (e.g., C8-C20 fatty acids), alkyl phosphonates, alkane sulfonates (e.g., sodium dodecylsulphate "SDS") or linear or branched alkyl benzene sulfonates, alkene sulfonates; and d) amphoteric and zwitterionic surfactants such as aminocarboxylic acids, aminodicarboxylic acids, alkybetaines, and mixtures thereof. Additional components may include fragrances, dyes, stabilizers of hydrogen peroxide (e.g., metal chelators such as 1-hydroxyethylidene-1,1-diphosphonic acid (DEQUEST® 2010, Solutia Inc., St. Louis, Mo. and ethylenediaminetetraacetic acid (EDTA)), TURPINAL® SL (CAS#2809-21-4), DEQUEST® 0520, DEQUEST® 0531, stabilizers of enzyme activity (e.g., polyethylene glycol (PEG)), and detergent builders.

In Situ Production of Peroxycarboxylic Acids using a Perhydrolase Catalyst

Cephalosporin C deacetylases (EC. 31.1.41; systematic name cephalosporin C acetylhydrolases; CAHs) are enzymes having the ability to hydrolyze the acetyl ester bond on cephalosporins such as cephalosporin C, 7-aminocephalosporanic acid, and 7-(thiophene-2-acetamido)cephalosporanic acid (Abbott, B. and Fukuda, D., *Appl. Microbiol.* 30(3):413-419 (1975)). CAHs belong to a larger family of structurally related enzymes referred to as the carbohydrate esterase family seven ("CE-7"; see Coutinho, P. M., Henrissat, B., supra). As used herein, the terms "CE-7", "CE-7 esterase", "CE-7 carbohydrate esterase", "CE-7 perhydrolase", and "CE-7 enzyme" will be used interchangeably to refer to an enzyme structurally classified as a member of the carbohydrate esterase family 7.

Members of the CE-7 enzyme family may be found in plants, fungi (e.g., *Cephalosporidium acremonium*), yeasts (e.g., *Rhodosporidium toruloides, Rhodotorula glutinis*), and bacteria such as *Thermoanaerobacterium* sp.; *Norcardia lactamdurans*, and various members of the genus *Bacillus* (Politino et al., *Appl. Environ. Microbiol.*, 63(12):4807-4811 (1997); Sakai et al., *J. Ferment. Bioeng.* 85:53-57 (1998); Lorenz, W. and Wiegel, J., *J. Bacteriol* 179:5436-5441 (1997); Cardoza et al., *Appl, Microbiol. Biotechnol.*, 54(3): 406-412 (2000); Mitsushima et al., (1995) *Appl. Env. Microbiol.* 61(6):2224-2229; Abbott, B. and Fukuda, D., *Appl. Microbiol.* 30(3):413-419 (1975); Vincent et al., supra, Takami et al., *NAR,* 28(21):4317-4331 (2000); Rey et al., *Genome Biol.*, 5(10): article 77 (2004); Degrassi et al., *Microbiology.*, 146:1585-1591 (2000); U.S. Pat. No. 6,645,233; U.S. Pat. No. 5,281,525; U.S. Pat. No. 5,338,676; and WO 99/03984. WO2007/070609 and U.S. Patent Application Publication Nos. 2008/0176299, 2008/176783, and 2009/0005590 to DiCosimo et al. disclose various enzymes structurally classified as CE-7 enzymes that have perhydrolysis activity suitable for producing efficacious concentrations of peroxycarboxylic acids from a variety of carboxylic acid ester substrates when combined with a source of peroxygen.

The CE-7 family includes both CAHs and acetyl xylan esterases (AXEs; E.C. 3.1.1.72). CE-7 family members share a common structural motif and typically exhibit ester hydrolysis activity for both acetylated xylooligosaccharides and cephalosporin C, suggesting that the CE-7 family represents a single class of proteins with a multifunctional deacetylase activity against a range of small substrates (Vincent et al., supra).

Vincent et al. analyzes the structural similarity among the members of this family and defines the signature motif characteristic of the CE-7 family. The signature motif is a combination of at least 3 highly conserved motifs as illustrated below. All sequence numbering is relative to the numbering of a reference sequence (in this case, the wild type *Thermotoga neapolitana* perhydrolase; SEQ ID NO: 32).

As per the amino acid residue numbering of reference sequence SEQ ID NO: 32, the CE-7 signature motif comprises 3 conserved motifs defined as:

a) Arg118-Gly119-Gln120;
b) Gly179-Xaa180-Ser181-Gln182-Gly183; and
c) His298-Glu299.

Typically, the Xaa at amino acid residue position 180 is glycine, alanine, proline, tryptophan, or threonine. Two of the three amino acid residues belonging to the catalytic triad are in bold. In one embodiment, the Xaa at amino acid residue position 180 is selected from the group consisting of glycine, alanine, proline, tryptophan, and threonine.

Further analysis of the conserved motifs within the CE-7 carbohydrate esterase family indicates the presence of an additional conserved motif (LXD at amino acid positions 267-269 of SEQ ID NO: 32) that may be to further define a perhydrolase belonging to the CE-7 carbohydrate esterase family (FIGS. 1 and 2). In a further embodiment, the signature motif defined above includes a fourth conserved motif defined as:

Leu267-Xaa268-Asp269.

The Xaa at amino acid residue position 268 is typically isoleucine, valine, or methionine. The fourth motif includes the aspartic acid residue (bold) that is the third member of the catalytic triad (Seri 81-Asp269-His298).

Any number of well-known global alignment algorithms (i.e., sequence analysis software) may be used to align two or more amino acid sequences (representing enzymes having perhydrolase activity) to determine the existence of the present signature motif (for example, CLUSTALW or Needleman and Wunsch (*J. Mol. Biol.*, 48:443-453 (1970)). The aligned sequence(s) is compared to the reference sequence (SEQ ID NO: 32). In one embodiment, a CLUSTAL alignment (CLUSTALW) using a reference amino acid sequence (as used herein the CAH sequence (SEQ ID NO: 32) from the *Thermotoga neapolitana*) is used to identify perhydrolases belonging to the CE-7 esterase family. The relative numbering of the conserved amino acid residues is based on the residue numbering of the reference amino acid sequence to account for small insertions or deletions (typically 5 to 6 amino acids or less) within the aligned sequence as illustrated in Table A.

TABLE A

Conserved motifs found within CE-7 enzymes having perhydrolase activity.

| Perhydrolase Sequence | RGQ motif[a] (Residue #s) | GXSQG motif[a] (Residue #s) | LXD motif[b] (Residue #s) | HE motif[a] (Residue #s) |
|---|---|---|---|---|
| SEQ ID NO: 32 | 118-120 | 186-190 | 272-274 | 303-304 |
| SEQ ID NO: 36 | 118-120 | 186-190 | 272-274 | 303-304 |
| SEQ ID NO: 202 | 118-120 | 186-190 | 272-274 | 303-304 |

TABLE A-continued

Conserved motifs found within CE-7 enzymes having perhydrolase activity.

| Perhydrolase Sequence | RGQ motif[a] (Residue #s) | GXSQG motif[a] (Residue #s) | LXD motif[b] (Residue #s) | HE motif[a] (Residue #s) |
|---|---|---|---|---|
| SEQ ID NO: 203 | 118-120 | 186-190 | 272-274 | 303-304 |
| SEQ ID NO. 204 | 118-120 | 186-190 | 272-274 | 303-304 |
| SEQ ID NO. 205 | 119-121 | 187-191 | 273-275 | 304-305 |

[a] = Conserved motifs defined by Vincent et al., supra, used to define the signature motif.
[b] = an additional motif that may be useful in further defining the signature motif defined by Vincent et al., supra.

Each of the present CE-7 variants having perhydrolytic activity was derived from one of the wild type perhydrolase sequences in Table A. Each of the present variants retain the CE-7 signature motif (i.e., changes introduced to the wild type sequence do not include changes to the conserved motifs provided in Table A.). More specifically, the present perhydrolases having improved activity have a substitution to amino acid residue 277 where the wild type cysteine is replaced with serine, threonine, valine or alanine (per the numbering of SEQ ID NOs: 32, 36, 202, 203, and 204). The same substitution occurs at amino acid reside 278 in SEQ ID NO: 205 (i.e., SEQ ID NO: 205 contains a single amino acid insertion that shifts the relative residue numbering by 1).

Each of the present variants comprises an improvement in perhydrolase specific activity [U/mg protein], enzyme volumetric activity [U/mL] in a reaction mixture, and/or an improvement in the ratio of perhydrolysis activity to hydrolysis activity (i.e, the "P/H ratio"). In one embodiment, the improvement in activity is measured as a fold increase in activity (perhydrolase specific activity [U/mg protein], perhydrolysis volumetric activity [U/mL] in a reaction mixture, and/or the P/H ratio) relative to the wild type sequence from which it was derived. In another embodiment, the fold improvement in enzyme activity (perhydrolysis specific activity, perhydrolysis volumetric activity, and/or an increase in the P/H ratio) for a variant CE-7 enzyme having at least 95% amino acid sequence identity to SEQ ID NO: 5 is relative to the activity measured for SEQ ID NO: 32; the fold improvement in activity for a variant CE-7 enzyme having at least 95% amino acid sequence identity to SEQ ID NO: 10 is relative to the activity measured for SEQ ID NO: 36; the fold improvement in activity for a variant CE-7 enzyme having at least 95% amino acid sequence identity to SEQ ID NO: 15 is relative to the activity measured for SEQ ID NO: 202; the fold improvement in activity for a variant CE-7 enzyme having at least 95% amino acid sequence identity to SEQ ID NO: 20 is relative to the activity measured for SEQ ID NO: 203; the fold improvement in activity for a variant CE-7 enzyme having at least 95% amino acid sequence identity to SEQ ID NO: 25 is relative to the activity measured for SEQ ID NO: 204; and the fold improvement in activity for a variant CE-7 enzyme having at least 95% amino acid sequence identity to SEQ ID NO: 30 is relative to the activity measured for SEQ ID NO: 205.

In one embodiment, the fold increase in perhydrolase specific activity for the present variants is at least 1.1, 1.2, 1.3, 1.4, 1.5, 1.6, 1.7, 1.8, 1.9, 2.0, 3.0, 4.0, 5.0, 6.0, 7.0, 8.0, 9.0, 10, 11, 12, or 13-fold when compared to the activity of the wild type sequence under substantially similar conditions.

In another embodiment, the fold increase in the P/H ratio for the present variants is at least 1.1, 1.2, 1.3, 1.4, 1.5, 1.6, 1.7, 1.8, 1.9, 2.0, 3.0, 4.0, 5.0, 6.0, 7.0, 8.0, 9.0 or 10-fold when compared to the P/H ratio of the wild type sequence under substantially similar conditions.

The present method produces industrially-useful, efficacious concentrations of peroxycarboxylic acids under aqueous reaction conditions using the perhydrolase activity of a variant enzyme belonging to the CE-7 family of carbohydrate esterases. In one embodiment, the present method produces efficacious concentrations of one or more peroxycarboxylic acids in situ.

HPLC Assay Method for Determining the Concentration of Peracid and Hydrogen Peroxide.

A variety of analytical methods can be used in the present method to analyze the reactants and products including, but not limited to titration, high performance liquid chromatography (HPLC), gas chromatography (GC), mass spectroscopy (MS), capillary electrophoresis (CE), the analytical procedure described by U. Karst et al., (*Anal. Chem.*, 69(17): 3623-3627 (1997)), and the 2,2'-azino-bis(3-ethylbenzothazoline)-6-sulfonate (ABTS) assay (S. Minning, et al., *Analytica Chimica Acta* 378:293-298 (1999) and WO 2004/058961 A1) as described in the present examples.

Determination of Minimum Biocidal Concentration of Peracids

The method described by J. Gabrielson, et al. (*J. Microbiol. Methods* 50: 63-73 (2002)) can be employed for determination of the Minimum Biocidal Concentration (MBC) of peracids, or of hydrogen peroxide and enzyme substrates. The assay method is based on XTT reduction inhibition, where XTT ((2,3-bis[2-methoxy-4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to viable plate counts, direct microscopic counts, dry weight, turbidity measurements, absorbance, and bioluminescence (see, for example Brock, Semour S., *Disinfection, Sterilization, and Preservation*, 5th edition, Lippincott Williams & Wilkins, Philadelphia, Pa., USA; 2001).

Uses of Enzymatically-Prepared Peroxycarboxylic Acid Compositions

The enzyme catalyst-generated peroxycarboxylic acid produced according to the present method can be used in a variety of hard surface/inanimate object applications for reduction of concentrations of biological contaminants, such as decontamination of medical instruments (e.g., endoscopes), textiles (e.g., garments, carpets), food preparation surfaces, food storage and food-packaging equipment, materials used for the packaging of food products, chicken hatcheries and grow-out facilities, animal enclosures, and spent process waters that have microbial and/or virucidal activity. The enzyme-generated peroxycarboxylic acids may be used in formulations designed to inactivate prions (e.g., certain proteases) to additionally provide biocidal activity. In a preferred aspect, the present peroxycarboxylic acid compositions are particularly useful as a disinfecting agent for non-autoclavable medical instruments and food packaging equipment. As the peroxycarboxylic acid-containing formulation may be prepared using GRAS or food-grade components (enzyme, enzyme substrate, hydrogen peroxide, and buffer), the enzyme-generated peracid may also be used for decontamination of animal carcasses, meat, fruits and vegetables, or for decontamination of prepared foods. The enzyme-generated peroxycarboxylic acid may be incorporated into a product whose final form is a powder, liquid, gel, film, solid or aerosol. The enzyme-generated peroxycarboxylic acid may be diluted to a concentration that still provides an efficacious decontamination.

The compositions comprising an efficacious concentration of peroxycarboxylic acid can be used to disinfect surfaces and/or objects contaminated (or suspected of being contaminated) with biological contaminants by contacting the surface or object with the products produced by the present processes. As used herein, "contacting" refers to placing a disinfecting composition comprising an effective concentration of peroxycarboxylic acid in contact with the surface or inanimate object suspected of contamination with a disease-causing entity for a period of time sufficient to clean and disinfect. Contacting includes spraying, treating, immersing, flushing, pouring on or in, mixing, combining, painting, coating, applying, affixing to and otherwise communicating a peroxycarboxylic acid solution or composition comprising an efficacious concentration of peroxycarboxylic acid, or a solution or composition that forms an efficacious concentration of peroxycarboxylic acid, with the surface or inanimate object suspected of being contaminated with a concentration of a biological contaminant. The disinfectant compositions may be combined with a cleaning composition to provide both cleaning and disinfection. Alternatively, a cleaning agent (e.g., a surfactant or detergent) may be incorporated into the formulation to provide both cleaning and disinfection in a single composition.

The compositions comprising an efficacious concentration of peroxycarboxylic acid can also contain at least one additional antimicrobial agent, combinations of prion-degrading proteases, a virucide, a sporicide, or a biocide. Combinations of these agents with the peroxycarboxylic acid produced by the claimed processes can provide for increased and/or synergistic effects when used to clean and disinfect surfaces and/or objects contaminated (or suspected of being contaminated) with biological contaminants, such as microorganisms, spores, viruses, fungi, and/or prions. Suitable antimicrobial agents include carboxylic esters (e.g., p-hydroxy alkyl benzoates and alkyl cinnamates); sulfonic acids (e.g., dodecylbenzene sulfonic acid); iodo-compounds or active halogen compounds (e.g., elemental halogens, halogen oxides (e.g., NaOCl, HOCl, HOBr, $ClO_2$), iodine, interhalides (e.g., iodine monochloride, iodine dichloride, iodine trichloride, iodine tetrachloride, bromine chloride, iodine monobromide, or iodine dibromide); polyhalides; hypochlorite salts; hypochlorous acid; hypobromite salts; hypobromous acid; chloro- and bromo-hydantoins; chlorine dioxide; and sodium chlorite); organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$-$C_6$ alkyl hydroxy benzoates), quaternary ammonium compounds (such as alkyldimethylbenzyl ammonium chloride, dialkyldimethyl ammonium chloride and mixtures thereof); and mixtures of such antimicrobial agents, in an amount sufficient to provide the desired degree of microbial protection. Effective amounts of antimicrobial agents include about 0.001 wt % to about 60 wt % antimicrobial agent, about 0.01 wt % to about 15 wt % antimicrobial agent, or about 0.08 wt % to about 2.5 wt % antimicrobial agent.

In one aspect, the peroxycarboxylic acids formed by the present process can be used to reduce the concentration of viable biological contaminants (such as a viable microbial population) when applied on and/or at a locus. As used herein, a "locus" comprises part or all of a target surface suitable for disinfecting or bleaching. Target surfaces include all surfaces that can potentially be contaminated with biological contaminants. Non-limiting examples include equipment surfaces found in the food or beverage industry (such as tanks, conveyors, floors, drains, coolers, freezers, equipment surfaces, walls, valves, belts, pipes, drains, joints, crevasses, combinations thereof, and the like); building surfaces (such as walls, floors and windows); non-food-industry related pipes and drains, including water treatment facilities, pools and spas, and fermentation tanks; hospital or veterinary surfaces (such as walls, floors, beds, equipment (such as endoscopes), clothing worn in hospital/veterinary or other healthcare settings, including clothing, scrubs, shoes, and other hospital or veterinary surfaces); restaurant surfaces; bathroom surfaces; toilets; clothes and shoes; surfaces of barns or stables for livestock, such as poultry, cattle, dairy cows, goats, horses and pigs; hatcheries for poultry or for shrimp; and pharmaceutical or biopharmaceutical surfaces (e.g., pharmaceutical or biopharmaceutical manufacturing equipment, pharmaceutical or biopharmaceutical ingredients, pharmaceutical or biopharmaceutical excipients). Additional hard surfaces also include food products, such as beef, poultry, pork, vegetables, fruits, seafood, combinations thereof, and the like. The locus can also include water absorbent materials such as infected linens or other textiles. The locus also includes harvested plants or plant products including seeds, corms, tubers, fruit, and vegetables, growing plants, and especially crop growing plants, including cereals, leaf vegetables and salad crops, root vegetables, legumes, berried fruits, citrus fruits and hard fruits.

Non-limiting examples of hard surface materials are metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth)acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon). Additional surfaces include brick, tile, ceramic, porcelain, wood, vinyl, linoleum, and carpet.

The peroxycarboxylic acids formed by the present process may be used to provide a benefit to an article of clothing or a textile including, but not limited to, disinfecting, sanitizing, bleaching, destaining, and deodorizing. The peroxycarboxylic acids formed by the present process may be used in any number of laundry care products including, but not limited to, textile pre-wash treatments, laundry detergents, stain removers, bleaching compositions, deodorizing compositions, and rinsing agents.

Recombinant Microbial Expression

The genes and gene products of the instant sequences may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The perhydrolase may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus*. In one embodiment, bacterial host strains include *Escherichia, Bacillus, Kluyveromyces,* and *Pseudomonas*. In a preferred embodiment, the bacterial host cell is *Escherichia coli*.

Large-scale microbial growth and functional gene expression may use a wide range of simple or complex carbohydrates, organic acids and alcohols or saturated hydrocarbons, such as methane or carbon dioxide in the case of photosynthetic or chemoautotrophic hosts, the form and amount of nitrogen, phosphorous, sulfur, oxygen, carbon or any trace micronutrient including small inorganic ions. The regulation of growth rate may be affected by the addition, or not, of specific regulatory molecules to the culture and which are not typically considered nutrient or energy sources.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell and/or native to the production host, although such control regions need not be so derived.

Initiation control regions or promoters, which are useful to drive expression of the present cephalosporin C deacetylase coding region in the desired host cell are numerous and familiar to those skilled in the art. Virtually any promoter capable of driving these genes is suitable for the present invention including but not limited to, CYC1 HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, araB, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred host cell. In one embodiment, the inclusion of a termination control region is optional. In another embodiment, the chimeric gene includes a termination control region derived the preferred host cell.

INDUSTRIAL PRODUCTION

A variety of culture methodologies may be applied to produce the present perhydrolase catalyst. For example, large-scale production of a specific gene product overexpressed from a recombinant microbial host may be produced by batch, fed-batch, and continuous culture methodologies. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem, Biotechnol.*, 36:227-234 (1992).

Commercial production of the desired perhydrolase catalyst may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Recovery of the desired perhydrolase catalysts from a batch fermentation, fed-batch fermentation, or continuous culture, may be accomplished by any of the methods that are known to those skilled in the art. For example, when the enzyme catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired enzyme catalyst. The cell extract may optionally be filtered through an appropriate filter aid such as celite or silica to remove cell debris prior to a heat-treatment step to precipitate undesired protein from the enzyme catalyst solution. The solution containing the desired enzyme catalyst may then be separated from the precipitated cell debris and protein by membrane filtration or centrifugation, and the resulting partially-purified enzyme catalyst solution concentrated by additional membrane filtration, then optionally mixed with an appropriate excipient (for example, maltodextrin, trehalose, sucrose, lactose, sorbitol, mannitol, phosphate buffer, citrate buffer, or mixtures thereof) and spray-dried to produce a solid powder comprising the desired enzyme catalyst.

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

General Methods

The following examples are provided to demonstrate preferred embodiments. It should be appreciated by those of skill in the art that the techniques disclosed in the examples which follow represent techniques discovered by the inventor to function well in the practice of the methods disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the presently disclosed methods.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma-Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "µL" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "µg" means microgram(s), "ng" means nanogram(s), "g" means gravity, "HPLC" means high performance liquid chromatography, "dd H$_2$O" means distilled and deionized water, "dcw" means dry cell weight, "ATCC" or "ATCC®" means the American Type Culture Collection (Manassas, Va.), "U" means unit(s) of perhydrolase activity, "rpm" means revolution(s) per minute, and "EDTA" means ethylenediaminetetraacetic acid.

Example 1

Cloning and Expression of Acetyl Xylan Esterase from *Thermotoga neapolitana*

A coding region encoding an acetyl xylan esterase from *Thermotoga neapolitana* (GENBANK® accession #AAB70869, SEQ ID NO:32) was synthesized using codons optimized for expression in *E. coli* (DNA 2.0, Menlo Park, Calif.). The coding region was subsequently amplified by PCR (0.5 min at 94° C., 0.5 min at 55° C., 1 min at 70° C., 30 cycles) using primers identified as SEQ ID NO:33 and SEQ ID NO:34. The resulting nucleic acid product (SEQ ID NO: 35) was subcloned into pTrcHis2-TOPO® (Invitrogen, Carlsbad, Calif.) to generate the plasmid identified as pSW196. The plasmid pSW196 was used to transform *E. coli* KLP18 to generate the strain identified as KLP18/pSW196 (See Published U.S. Patent Application No. 2008/0176299 to DiCosimo et al., incorporated herein by reference in its entirety). KLP18/pSW196 was gown in LB media at 37° C. with shaking up to OD$_{600nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 2

Fermentation of *E. coli* KLP18 Transformant Expressing *T. neapolitana* Acetyl Xylan Esterase A fermentor seed culture was prepared by charging a 2-L shake flask with 0.5 L seed medium containing yeast extract (Amberex 695, 5.0 g/L), K$_2$HPO$_4$ (10.0 g/L), KH$_2$PO$_4$(7.0 g/L), sodium citrate dihydrate (1.0 g/L), (NH$_4$)$_2$SO$_4$ (4.0 g/L), MgSO$_4$ heptahydrate (1.0 g/L) and ferric ammonium citrate (0.10 g/L). The pH of the medium was adjusted to 6.8, and the medium was sterilized in the flask. Post sterilization additions included glucose (50 wt %, 10.0 mL) and 1 mL ampicillin (25 mg/mL) stock solution. The seed medium was inoculated with a 1-mL culture of *E. coli* KLP18/pSW196 (Example 1) in 20% glycerol, and cultivated at 35° C. and 300 rpm. The seed culture was transferred at ca. 1-2 OD$_{550}$ to a 14-L fermentor (Braun Biotech, Allentown, Pa.) with 8 L of medium at 35° C. containing KH$_2$PO$_4$ (3.50 g/L), FeSO$_4$ heptahydrate (0.05 g/L), MgSO$_4$ heptahydrate (2.0 g/L), sodium citrate dihydrate (1.90 g/L), yeast extract (Amberex 695, 5.0 g/L), Biospumex153K antifoam (0.25 mL/L, Cognis Corporation, Monheim, Germany), NaCl (1.0 g/L), CaCl$_2$ dihydrate (10 g/L), and NIT trace elements solution (10 mL/L). The trace elements solution contained citric acid monohydrate (10 g/L), MnSO$_4$ hydrate (2 g/L), NaCl (2 g/L), FeSO$_4$ heptahydrate (0.5 g/L), ZnSO$_4$ heptahydrate (0.2 g/L), CuSO$_4$ pentahydrate (0.02 g/L) and NaMoO$_4$ dihydrate (0.02 g/L). Post sterilization additions included glucose solution (50% w/w, 80.0 g) and ampicillin (25 mg/mL) stock solution (16.00 mL). Glucose solution (50% w/w) was used for fed batch. Glucose feed was initiated when glucose concentration decreased to 0.5 g/L, starting at 0.31 g feed/min and increasing progressively each hour to 0.36, 0.42, 0.49, 0.57, 0.66, 0.77, 0.90, 1.04, 1.21, 1.41, and 1.63 g/min respectively; the rate remained constant afterwards. Glucose concentration in the medium was monitored, and if the concentration exceeded 0.1 g/L the feed rate was decreased or stopped temporarily. Induction was initiated between OD$_{550}$=56 and OD$_{550}$=80 with addition of 16 mL IPTG (0.5 M) for the various strains. The dissolved oxygen (DO) concentration was controlled at 25% of air saturation. The DO was controlled first by impeller agitation rate (400 to 1400 rpm) and later by aeration rate (2 to 10 slpm). The pH was controlled at 6.8. NH$_4$OH (29% w/w) and H$_2$SO$_4$ (20% w/v) were used for pH control. The head pressure was 0.5 bars. The cells were harvested by centrifugation 16 h post IPTG addition.

Example 3

Modeling of *Thermotoga neapolitana* Acetyl Xylan Esterase

Amino acid sequences of acetyl xylan esterases from *T. neapolitana* (SEQ ID NO: 32) and *Thermotoga maritima* MSB8 (SEQ ID NO: 36) were aligned using CLUSTALW (FIG. 1). The X-ray crystal structure of *T. maritima* acetyl xylan esterase (1VLQ) was obtained from the Research Collaboratory for Structural Bioinformatics (RCSB) protein databank (PDP) (See H. M. Berman, J. Westbrook, Z. Feng, G. Gilliland, T. N. Bhat, H. Weissig, I. N. Shindyalov, P. E. Bourne: The Protein Data Bank. *Nucleic Acids Research*, 28 pp. 235-242 (2000) and H. M. Berman, K. Henrick, H. Nakamura, Announcing the worldwide Protein Data Bank., *Nature Structural Biology* 10 (12), p. 980 (2003). All *T. maritima* amino acids that differ from the corresponding *T. neapolitana* amino acids were replaced with the *T. neapolitana* amino acid using Accelrys DISCOVERY STUDIO® 2.0 software (Protocols>Protein Modeling>Build mutants; Accelrys Software Inc., San Diego, Calif.). In addition, selenomethionines were replaced with methionine. The number of models chosen for the output was 3, the optimization level was set to "high" and Use DOPE method was set to "true". Structure overlays and visualizations were done using PyMol™ version 0.99 (DeLano Scientific LLC, Palo Alto, Calif.). Model quality was judged based on whether the catalytic triad (H303, S188, and D274) remained in the correct position and whether the overall structure was retained with respect to the original model.

Example 4

Identification of Amino Acid Residues in *Thermotoga neapolitana* Acetyl Xylan Esterase for Saturation Mutagenesis In addition to the canonical catalytic triad (H303, S188, and D274), several residues are also present within the acetyl xylan esterase active site based on the model. Substitution of one or more of these residues with an alternative amino acid might be expected to alter the functionality of the enzyme. However, the specific effects of such substitutions are unknown a priori. Residues F213 (Phe213), I276 (Ile276), C277 (Cys277) and N93 (Asn93) of SEQ ID NO: 32 were selected for site-saturation mutagenesis. Residue Y92 (Tyr92) was not selected because of the high level of conservation of this residue across the CE-7 family.

Example 5

Saturation Mutagenesis at Amino Acid Residue Positions F213, I276, C277 and N93 of *Thermotoga neapolitana* Acetyl Xylan Esterase To individually change each of the four selected residues (F213, I276, C277, N93) to each of the other possible 19 amino acids, primers pairs (Table 1) were designed based on the codon optimized sequence of *T. neapolitana* acetyl xylan esterase (SEQ ID NO:35 in the plasmid pSW196 (See Example 1 above and U.S. Patent Application Pub. No. 2008/0176299)).

TABLE 1

Oligonucleotides used to change amino acid residues 277, 276, 213 and 93 in *T. neapolitana*.

| C277 | forward 5' to 3' | | reverse 5' to 3' |
|---|---|---|---|
| TNEA_C277Gf (SEQ ID NO: 42) | ggacactattGGCccgccgtcta | TNEA_C277Gr (SEQ ID NO: 43) | TAGACGGCGGGCCAATAGTGTCC |
| TNEA_C277Af (SEQ ID NO: 44) | ggacactattGCGccgccgtcta | TNEA_C277Ar (SEQ ID NO: 45) | TAGACGGCGGCGCAATAGTGTCC |
| TNEA_C277Vf (SEQ ID NO: 46) | ggacactattGTGccgccgtcta | TNEA_C277Vr (SEQ ID NO: 47) | TAGACGGCGGCACAATAGTGTCC |
| TNEA_C277Lf (SEQ ID NO: 48) | ggacactattCTGccgccgtcta | TNEA_C277Lr (SEQ ID NO: 49) | TAGACGGCGGCAGAATAGTGTCC |
| TNEA_C277If (SEQ ID NO: 50) | ggacactattATTccgccgtcta | TNEA_C277Ir (SEQ ID NO: 51) | TAGACGGCGGAATAATAGTGTCC |
| TNEA_C277Pf (SEQ ID NO: 52) | ggacactattCCGccgccgtcta | TNEA_C277Pr (SEQ ID NO: 53) | TAGACGGCGGCGGAATAGTGTCC |
| TNEA_C277Ff (SEQ ID NO: 54) | ggacactattTTTccgccgtcta | TNEA_C277Fr (SEQ ID NO: 55) | TAGACGGCGGAAAAATAGTGTCC |
| TNEA_C277Yf (SEQ ID NO: 56) | ggacactattTATccgccgtcta | TNEA_C277Yr (SEQ ID NO: 57) | TAGACGGCGGATAAATAGTGTCC |
| TNEA_C277Wf (SEQ ID NO: 58) | ggacactattTGGccgccgtcta | TNEA_C277Wr (SEQ ID NO: 59) | TAGACGGCGGCCAAATAGTGTCC |
| TNEA_C277Sf (SEQ ID NO: 60) | ggacactattAGCccgccgtcta | TNEA_C277Sr (SEQ ID NO: 61) | TAGACGGCGGGCTAATAGTGTCC |
| TNEA_C277Tf (SEQ ID NO: 62) | ggacactattACCccgccgtcta | TNEA_C277Tr (SEQ ID NO: 63) | TAGACGGCGGGGTAATAGTGTCC |
| TNEA_C277Qf (SEQ ID NO: 64) | ggacactattCAGccgccgtcta | TNEA_C277Qr (SEQ ID NO: 65) | TAGACGGCGGCTGAATAGTGTCC |
| TNEA_C277Nf (SEQ ID NO: 66) | ggacactattAACccgccgtcta | TNEA_C277Nr (SEQ ID NO: 67) | TAGACGGCGGGTTAATAGTGTCC |
| TNEA_C277Df (SEQ ID NO: 68) | ggacactattGATccgccgtcta | TNEA_C277Dr (SEQ ID NO: 69) | TAGACGGCGGATCAATAGTGTCC |
| TNEA_C277Ef (SEQ ID NO: 70) | ggacactattGAAccgccgtcta | TNEA_C277Er (SEQ ID NO: 71) | TAGACGGCGGTTCAATAGTGTCC |
| TNEA_C277Rf (SEQ ID NO: 72) | ggacactattCGTccgccgtcta | TNEA_C277Rr (SEQ ID NO: 73) | TAGACGGCGGACGAATAGTGTCC |
| TNEA_C277Hf (SEQ ID NO: 74) | ggacactattCATccgccgtcta | TNEA_C277Hr (SEQ ID NO: 75) | TAGACGGCGGATGAATAGTGTCC |
| TNEA_C277Kf (SEQ ID NO: 76) | ggacactattAAAccgccgtcta | TNEA_C277Kr (SEQ ID NO: 77) | TAGACGGCGGTTTAATAGTGTCC |

TABLE 1-continued

Oligonucleotides used to change amino acid residues 277, 276, 213 and 93 in *T. neapolitana*.

| | | | |
|---|---|---|---|
| TNEA_C277Mf (SEQ ID NO: 78) | ggacactatt<u>ATG</u>ccgccgtcta | TNEA_C277Mr (SEQ ID NO: 79) | TAGACGGCGGCATAATAGTGTCC |
| I276 | forward 5' to 3' | | reverse 5' to 3' |
| TNEA_I276Gf (SEQ ID NO: 80) | gatggacactGGCgtgtccgccgt | TNEA_I276Gr (SEQ ID NO: 81) | ACGGCGGACAGCCAGTGTCCATC |
| TNEA_I276Af (SEQ ID NO: 82) | gatggacactGCGgtgtccgccgt | TNEA_I276Ar (SEQ ID NO: 83) | ACGGCGGACACGCAGTGTCCATC |
| TNEA_I276Vf (SEQ ID NO: 84) | gatggacactGTGgtgtccgccgt | TNEA_I276Vr (SEQ ID NO: 85) | ACGGCGGACACACAGTGTCCATC |
| TNEA_I276Lf (SEQ ID NO: 86) | gatggacactCTGgtgtccgccgt | TNEA_I276Lr (SEQ ID NO: 87) | ACGGCGGACACAGAGTGTCCATC |
| TNEA_I276Cf (SEQ ID NO: 88) | gatggacactTGCgtgtccgccgt | TNEA_I276Cr (SEQ ID NO: 89) | ACGGCGGACAGCAAGTGTCCATC |
| TNEA_I276Pf (SEQ ID NO: 90) | gatggacactCCGgtgtccgccgt | TNEA_I276Pr (SEQ ID NO: 91) | ACGGCGGACACGGAGTGTCCATC |
| TNEA_I276Ff (SEQ ID NO: 92) | gatggacactTTTgtgtccgccgt | TNEA_I276Fr (SEQ ID NO: 93) | ACGGCGGACAAAAAGTGTCCATC |
| TNEA_I276Yf (SEQ ID NO: 94) | gatggacactTATgtgtccgccgt | TNEA_I276Yr (SEQ ID NO: 95) | ACGGCGGACAATAAGTGTCCATC |
| TNEA_I276Wf (SEQ ID NO: 96) | gatggacactTGGgtgtccgccgt | TNEA_I276Wr (SEQ ID NO: 97) | ACGGCGGACACCAAGTGTCCATC |
| TNEA_I276Sf (SEQ ID NO: 98) | gatggacactAGCgtgtccgccgt | TNEA_I276Sr (SEQ ID NO: 99) | ACGGCGGACAGCTAGTGTCCATC |
| TNEA_I276Tf (SEQ ID NO: 100) | gatggacactACCgtgtccgccgt | TNEA_I276Tr (SEQ ID NO: 101) | ACGGCGGACAGGTAGTGTCCATC |
| TNEA_I276Qf (SEQ ID NO: 102) | gatggacactCAGgtgtccgccgt | TNEA_I276Qr (SEQ ID NO: 103) | ACGGCGGACACTGAGTGTCCATC |
| TNEA_I276Nf (SEQ ID NO: 104) | gatggacactAACgtgtccgccgt | TNEA_I276Nr (SEQ ID NO: 105) | ACGGCGGACAGTTAGTGTCCATC |
| TNEA_I276Df (SEQ ID NO: 106) | gatggacactGATgtgtccgccgt | TNEA_I276Dr (SEQ ID NO: 107) | ACGGCGGACAATCAGTGTCCATC |
| TNEA_I276Ef (SEQ ID NO: 108) | gatggacactGAAgtgtccgccgt | TNEA_I276Er (SEQ ID NO: 109) | ACGGCGGACATTCAGTGTCCATC |
| TNEA_I276Rf (SEQ ID NO: 110) | gatggacactCGTgtgtccgccgt | TNEA_I276Rr (SEQ ID NO: 111) | ACGGCGGACAACGAGTGTCCATC |
| TNEA_I276Hf (SEQ ID NO: 112) | gatggacactCATgtgtccgccgt | TNEA_I276Hr (SEQ ID NO: 113) | ACGGCGGACAATGAGTGTCCATC |
| TNEA_I276Kf (SEQ ID NO: 114) | gatggacactAAAgtgtccgccgt | TNEA_I276Kr (SEQ ID NO: 115) | ACGGCGGACATTTAGTGTCCATC |
| TNEA_I276Mf (SEQ ID NO: 116) | gatggacact<u>ATG</u>gtgtccgccgt | TNEA_I276Mr (SEQ ID NO: 117) | ACGGCGGACACATAGTGTCCATC |
| F213 | forward 5' to 3' | | reverse 5' to 3' |
| TNEA_F213Gf (SEQ ID NO: 118) | cgatgttccgGGCctgtgccact | TNEA_F213Gr (SEQ ID NO: 119) | AGTGGCACAG<u>GCC</u>CGGAACATCG |
| TNEA_F213Af (SEQ ID NO: 120) | cgatgttccgGCGctgtgccact | TNEA_F213Ar (SEQ ID NO: 121) | AGTGGCACAG<u>CGC</u>CGGAACATCG |
| TNEA_F213Vf (SEQ ID NO: 122) | cgatgttccgGTGctgtgccact | TNEA_F213Vr (SEQ ID NO: 123) | AGTGGCACAG<u>CAC</u>CGGAACATCG |
| TNEA_F213Lf (SEQ ID NO: 124) | cgatgttccgCTGctgtgccact | TNEA_F213Lr (SEQ ID NO: 125) | AGTGGCACAG<u>CAG</u>CGGAACATCG |

TABLE 1-continued

Oligonucleotides used to change amino acid residues 277, 276, 213 and 93 in *T. neapolitana*.

| | | | |
|---|---|---|---|
| TNEA_F213If (SEQ ID NO: 126) | cgatgttccgATTctgtgccact | TNEA_F213Ir (SEQ ID NO: 127) | AGTGGCACAGAATCGGAACATCG |
| TNEA_F213Pf (SEQ ID NO: 128) | cgatgttccgCCGctgtgccact | TNEA_F213Pr (SEQ ID NO: 129) | AGTGGCACAGCGGCGGAACATCG |
| TNEA_F213Cf (SEQ ID NO: 130) | cgatgttccgTGCctgtgccact | TNEA_F213Cr (SEQ ID NO: 131) | AGTGGCACAGGCACGGAACATCG |
| TNEA_F213Yf (SEQ ID NO: 132) | cgatgttccgTATctgtgccact | TNEA_F213Yr (SEQ ID NO: 133) | AGTGGCACAGATACGGAACATCG |
| TNEA_F213Wf (SEQ ID NO: 134) | cgatgttccgTGGctgtgccact | TNEA_F213Wr (SEQ ID NO: 135) | AGTGGCACAGCCACGGAACATCG |
| TNEA_F213Sf (SEQ ID NO: 136) | cgatgttccgAGCctgtgccact | TNEA_F213Sr (SEQ ID NO: 137) | AGTGGCACAGGCTCGGAACATCG |
| TNEA_F213Tf (SEQ ID NO: 138) | cgatgttccgACCctgtgccact | TNEA_F213Tr (SEQ ID NO: 139) | AGTGGCACAGGGTCGGAACATCG |
| TNEA_F213Qf (SEQ ID NO: 140) | cgatgttccgCAGctgtgccact | TNEA_F213Qr (SEQ ID NO: 141) | AGTGGCACAGCTGCGGAACATCG |
| TNEA_F213Nf (SEQ ID NO: 142) | cgatgttccgAACctgtgccact | TNEA_F213Nr (SEQ ID NO: 143) | AGTGGCACAGGTTCGGAACATCG |
| TNEA_F213Df (SEQ ID NO: 144) | cgatgttccgGATctgtgccact | TNEA_F213Dr (SEQ ID NO: 145) | AGTGGCACAGATCCGGAACATCG |
| TNEA_F213Ef (SEQ ID NO: 146) | cgatgttccgGAActgtgccact | TNEA_F213Er (SEQ ID NO: 147) | AGTGGCACAGTTCCGGAACATCG |
| TNEA_F213Rf (SEQ ID NO: 148) | cgatgttccgCGTctgtgccact | TNEA_F213Rr (SEQ ID NO: 149) | AGTGGCACAGACGCGGAACATCG |
| TNEA_F213Hf (SEQ ID NO: 150) | cgatgttccgCATctgtgccact | TNEA_F213Hr (SEQ ID NO: 151) | AGTGGCACAGATGCGGAACATCG |
| TNEA_F213Kf (SEQ ID NO: 152) | cgatgttccgAAActgtgccact | TNEA_F213Kr (SEQ ID NO: 153) | AGTGGCACAGTTTCGGAACATCG |
| TNEA_F213Mf (SEQ ID NO: 154) | cgatgttccgATGctgtgccact | TNEA_F213Mr (SEQ ID NO: 155) | AGTGGCACAGCATCGGAACATCG |
| N093 | forward 5' to 3' | | reverse 5' to 3' |
| TNEA_N093Gf (SEQ ID NO: 156) | cattggttacGGCggtggccgtg | TNEA_N093Gr (SEQ ID NO: 157) | CACGGCCACCGCCGTAACCAATG |
| TNEA_N093Af (SEQ ID NO: 158) | cattggttacGCGggtggccgtg | TNEA_N093Ar (SEQ ID NO: 159) | CACGGCCACCGCGGTAACCAATG |
| TNEA_N093Vf (SEQ ID NO: 160) | cattggttacGTGggtggccgtg | TNEA_N093Vr (SEQ ID NO: 161) | CACGGCCACCGTGGTAACCAATG |
| TNEA_N093Lf (SEQ ID NO: 162) | cattggttacCTGggtggccgtg | TNEA_N093Lr (SEQ ID NO: 163) | CACGGCCACCCTGGTAACCAATG |
| TNEA_N093If (SEQ ID NO: 164) | cattggttacATTggtggccgtg | TNEA_N093Ir (SEQ ID NO: 165) | CACGGCCACCATTGTAACCAATG |
| TNEA_N093Pf (SEQ 1D NO: 166) | cattggttacCCGggtggccgtg | TNEA_N093Pr (SEQ ID NO: 167) | CACGGCCACCCCGGTAACCAATG |
| TNEA_N093Cf (SEQ ID NO: 168) | cattggttacTGCggtggccgtg | TNEA_N093Cr (SEQ ID NO: 169) | CACGGCCACCTGCGTAACCAATG |
| TNEA_N093Yf (SEQ ID NO: 170) | cattggttacTATggtggccgtg | TNEA_N093Yr (SEQ ID NO: 171) | CACGGCCACCTATGTAACCAATG |
| TNEA_N093Wf (SEQ ID NO: 172) | cattggttacTGGggtggccgtg | TNEA_N093Wr (SEQ ID NO: 173) | CACGGCCACCTGGGTAACCAATG |
| TNEA_N093Sf (SEQ ID NO: 174) | cattggttacAGCggtggccgtg | TNEA_N093Sr (SEQ ID NO: 175) | CACGGCCACCAGCGTAACCAATG |

TABLE 1-continued

Oligonucleotides used to change amino acid residues 277, 276, 213 and 93 in *T. neapolitana*.

| | | | |
|---|---|---|---|
| TNEA_N093Tf (SEQ ID NO: 176) | cattggttacACCggtggccgtg | TNEA_N093Tr (SEQ ID NO: 177) | CACGGCCACCACCGTAACCAATG |
| TNEA_N093Qf (SEQ ID NO: 178) | cattggttacCAGggtggccgtg | TNEA_N093Qr (SEQ ID NO: 179) | CACGGCCACCCAGGTAACCAATG |
| TNEA_N093Ff (SEQ ID NO: 180) | cattggttacTTTggtggccgtg | TNEA_N093Fr (SEQ ID NO: 181) | CACGGCCACCTTTGTAACCAATG |
| TNEA_N093Df (SEQ ID NO: 182) | cattggttacGATggtggccgtg | TNEA_N093Dr (SEQ ID NO: 183) | CACGGCCACCGATGTAACCAATG |
| TNEA_N093Ef (SEQ ID NO: 184) | cattggttacGAAggtggccgtg | TNEA_N093Er (SEQ ID NO: 185) | CACGGCCACCGAAGTAACCAATG |
| TNEA_N093Rf (SEQ ID NO: 186) | cattggttacCGTggtggccgtg | TNEA_N093Rr (SEQ ID NO: 187) | CACGGCCACCCGTGTAACCAATG |
| TNEA_N093Hf (SEQ ID NO: 188) | cattggttacCATggtggccgtg | TNEA_N093Hr (SEQ ID NO: 189) | CACGGCCACCCATGTAACCAATG |
| TNEA_N093kf (SEQ ID NO: 190) | cattggttacAAAggtggccgtg | TNEA_N093Kr (SEQ ID NO: 191) | CACGGCCACCAAAGTAACCAATG |
| TNEA_N093Mf (SEQ ID NO: 192) | cattggttacATGggtggccgtg | TNEA_N093Mr (SEQ ID NO: 193) | CACGGCCACCATGGTAACCAATG |

The mutations were made using QUIKCHANGE® (Stratagene, La Jolla, Calif.) kit according to the manufacturer's instructions. Amplified plasmids were treated with 1 U of DpnI at 37° C. for 1 hour. Treated plasmids were used to transform chemically competent *E. coli* XL1-Blue (Stratagene) (residues 213, 276 and 277) or chemically competent *E. coli* TOP10F' (Invitrogen, Carlsbad, Calif.) (residue 93). Transformants were plated on LB-agar supplemented with 0.1 mg ampicillin/mL and grown overnight at 37° C. Up to five individual colonies were picked and the plasmid DNA sequenced to confirm the expected mutations.

Example 6

Perhydrolase Activity Assay of *Thermotoga neapolitana* Acetyl Xylan Esterase Mutants Individual colonies of mutants were picked into 96-well plates containing 0.1 mL LB with 0.1 mg ampicillin/mL, and grown overnight at 37° C. without shaking. The overnight culture (0.003 mL) was transferred to an "Induction plate" (96 deep-well) containing 0.3 mL LB, 0.5 mM IPTG and 0.1 mg ampicillin/mL. Induction plates were grown overnight at 37° C. with shaking. 0.01 mL of Induction culture was transferred to "Lysis plate" (96-well) containing 0.09 mL of 56 mg/mL CELYTIC™ Express (Sigma-Aldrich, St. Louis, Mo.). Plates were slightly agitated first, before incubating at 25° C. for 30 minutes. Approximately 0.01 mL of Lysis culture was transferred to "Assay plate" (96-well) containing 0.09 mL "Assay solution pH 5.0" (100 mM triacetin, 100 mM hydrogen peroxide, 50 mM acetic acid pH 5.0). Approximately 0.01 mL of Lysis culture was also transferred to "Assay plate pH 7.5" (96-well) containing 0.09 mL "Assay solution pH 7.5" (100 mM triacetin, 100 mM hydrogen peroxide, 50 mM sodium phosphate pH 7.5). Plates were gently agitated for 30 seconds before incubating at ambient temperature for 10 minutes. The assay was quenched by addition of 0.1 mL of "Stop buffer" (100 mM ortho-phenylenediamine (OPD), 500 mM $NaH_2PO_4$ pH 2.0). Plates were gently agitated for 30 seconds before incubating at 25° C. for 30 minutes. The absorbance was read at 458 nm without a lid using a SPECTRAMAX® Plus[384] (Molecular Devices, Sunnyvale, Calif.). Analysis of the results indicated four mutants that demonstrated significantly greater perhydrolase activity compared to the native enzyme (Tables 2 and 3). All four are changes of the cysteine at residue 277 (C277A, C277V, C277S, and C277T; see SEQ ID NO: 5) increased perhydrolase activity.

TABLE 2

Perhydrolase activity (U/mL) at pH 5.0 of *T. neapolitana* acetyl xylan esterase variants.

| Mutant | U/mL | Mutant | U/mL | Mutant | U/mL | Mutant | U/mL |
|---|---|---|---|---|---|---|---|
| F213S | 0.17 | I276W | 0.18 | C277N | 0.17 | N093R | 0.11 |
| F213N | 0.18 | I276R | 0.18 | C277I | 0.17 | N093I | 0.10 |
| F213G | 0.17 | I276L | 0.18 | C277S | 0.43 | N093Q | 0.10 |
| F213C | 0.21 | I276K | 0.18 | C277A | 0.51 | N093K | 0.11 |
| F213V | 0.17 | I276M | 0.18 | C277Q | 0.17 | N093M | 0.10 |
| F213M | 0.17 | I276V | 0.26 | C277L | 0.17 | N093C | 0.12 |
| F213T | 0.17 | I276S | 0.17 | C277K | 0.17 | N093D | 0.10 |
| F213Y | 0.23 | I276N | 0.18 | C277V | 0.35 | N093S | 0.12 |
| F213I | 0.18 | I276C | 0.29 | C277E | 0.17 | N093G | 0.11 |
| F213Q | 0.17 | I276Q | 0.17 | C277P | 0.17 | N093V | 0.10 |
| F213H | 0.22 | I276F | 0.27 | C277D | 0.17 | N093L | 0.13 |
| F213R | 0.20 | I276H | 0.18 | C277M | 0.17 | N09E | 0.10 |
| F213W | 0.17 | I276D | 0.17 | C277F | 0.17 | N093F | 0.10 |
| F213P | 0.17 | I276E | 0.18 | C277T | 0.33 | N09A | 0.11 |
| F213D | 0.17 | I276G | 0.17 | C277Y | 0.17 | N093H | 0.11 |
| F213K | 0.17 | I276Y | 0.23 | C277H | 0.17 | N093W | 0.10 |
| F213L | 0.18 | I276T | 0.29 | C277W | N/A | N093P | 0.10 |
| F213E | N/A | I276A | N/A | C277R | N/A | N093Y | 0.10 |
| F213A | N/A | I276P | N/A | C277G | N/A | N093T | N/A |
| | | | | | | native | 0.16 |

TABLE 3

Perhydrolase activity at pH 7.5 of *T. neapolitana* acetyl xylan esterase variants.

| Mutant | U/mL | Mutant | U/mL | Mutant | U/mL | Mutant | U/mL |
|---|---|---|---|---|---|---|---|
| F213S | 1.80 | I276W | 2.00 | C277N | 3.50 | N093R | 0.13 |
| F213N | 1.90 | I276R | 1.90 | C277I | 3.60 | N093I | 0.10 |
| F213G | 1.70 | I276L | 2.00 | C277S | 9.30 | N093Q | 0.11 |
| F213C | 3.00 | I276K | 1.90 | C277A | 7.50 | N093K | 0.13 |
| F213V | 1.70 | I276M | 1.90 | C277Q | 3.50 | N093M | 0.12 |
| F213M | 1.90 | I276V | 3.40 | C277L | 3.60 | N093C | 0.15 |
| F213T | 1.80 | I276S | 1.90 | C277K | 3.50 | N093D | 0.10 |
| F213Y | 2.60 | I276N | 2.10 | C277V | 6.10 | N093S | 0.23 |
| F213I | 1.80 | I276C | 3.40 | C277E | 3.50 | N093G | 0.18 |
| F213Q | 1.80 | I276Q | 2.00 | C277P | 3.60 | N093V | 0.10 |
| F213H | 2.30 | I276F | 2.70 | C277D | 3.70 | N093L | 0.22 |
| F213R | 2.20 | I276H | 2.10 | C277M | 3.60 | N09E | 0.12 |
| F213W | 1.80 | I276D | 1.90 | C277F | 3.60 | N093F | 0.10 |
| F213P | 3.50 | I276E | 1.90 | C277T | 9.60 | N09A | 0.13 |
| F213D | 3.60 | I276G | 3.60 | C277Y | 3.60 | N093H | 0.18 |
| F213K | 3.60 | I276Y | 4.40 | C277H | 3.60 | N093W | 0.16 |
| F213L | 5.00 | I276T | 3.00 | C277W | N/A | N093P | 0.12 |
| F213E | N/A | I276A | N/A | C277R | N/A | N093Y | 0.15 |
| F213A | N/A | I276P | N/A | C277G | N/A | N093T | N/A |
|  |  |  |  |  |  | native | 0.23 |

Example 7

Expression of *Thermotoga neapolitana* Acetyl Xylan Esterase Variants in *E. coli* KLP18

Plasmids with confirmed acetyl xylan esterase mutations were used to transform *E. coli* KLP18 (Example 1). Transformants were plated onto LB-ampicillin (100 μg/mL) plates and incubated overnight at 37° C. Cells were harvested from a plate using 2.5 mL LB media supplemented with 20% (v/v) glycerol, and 1.0 mL aliquots of the resulting cell suspension frozen at −80° C. One mL of the thawed cell suspension was transferred to a 1-L APPLIKON® Bioreactor (Applikon® Biotechnology, Foster City, Calif.) with 0.7 L medium containing $KH_2PO_4$ (5.0 g/L), $FeSO_4$ heptahydrate (0.05 g/L), $MgSO_4$ heptahydrate (1.0 g/L), sodium citrate dihydrate (1.90 g/L), yeast extract (Amberex 695, 5.0 g/L), Biospumex153K antifoam (0.25 mL/L, Cognis Corporation), NaCl (1.0 g/L), $CaCl_2$ dihydrate (0.1 g/L), and NIT trace elements solution (10 mL/L). The trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post sterilization additions included glucose solution (50% w/w, 6.5 g) and ampicillin (25 mg/mL) stock solution (2.8 mL). Glucose solution (50% w/w) was also used for fed batch. Glucose feed was initiated 40 min after glucose concentration decreased below 0.5 g/L, starting at 0.03 g feed/min and increasing progressively each hour to 0.04, 0.04, 0.05, 0.06, 0.07, 0.08, 0.09, 0.12, and 0.14 g/min respectively; the rate remaining constant afterwards. Glucose concentration in the medium was monitored, and if the concentration exceeded 0.1 g/L the feed rate was decreased or stopped temporarily. Induction was initiated at $OD_{550}$=50 with addition of 0.8 mL IPTG (0.05 M). The dissolved oxygen (DO) concentration was controlled at 25% of air saturation, first by agitation (400-1000 rpm), and following by aeration (0.5-2 slpm). The temperature was controlled at 37° C., and the pH was controlled at 6.8; $NH_4OH$ (29% w/w) and $H_2SO_4$ (20% w/v) were used for pH control. The cells were harvested by centrifugation (5,000×g for 15 minutes) at 20 h post IPTG addition.

Example 8

Preparation of Cell Lysates Containing Semi-Purified *T. neapolitana* Acetyl Xylan Esterase or *T. neapolitana* Variant Acetyl Xylan Esterases A cell culture of *E. coli* KLP18/pSW196 (*Thermotoga neapolitana* wild-type perhydrolase) was grown as described in Example 2. The resulting cell paste was resuspended (20% w/v) in 50 mM phosphate buffer pH 7.0 supplemented with 1.0 mM DTT. Resuspended cells were passed through a French pressure cell twice to ensure >95% cell lysis. Lysed cells were centrifuged for 30 minutes at 12,000×g, and the supernatant was heated at 75° C. for 20 minutes, followed by quenching in an ice bath for 2 minutes. Precipitated protein was removed by centrifugation for 10 minutes at 11,000×g. SDS-PAGE indicated that the CE-7 enzyme comprised approximately 85-90% of the total protein in the heat-treated extract supernatant.

Cell cultures of *E. coli* KLP18/pSW196/C277S (*Thermotoga neapolitana* C277S variant perhydrolase), *E. coli* KLP18/pSW196/C277V (*Thermotoga neapolitana* C277V variant perhydrolase), *E. coli* KLP18/pSW196/C277A (*Thermotoga neapolitana* C277A variant perhydrolase), and *E. coli* KLP18/pSW196/C277T (*Thermotoga neapolitana* C277T variant perhydrolase) were each grown as described in Example 7. The resulting cell pastes were resuspended (20% w/v) in 50 mM phosphate buffer pH 7.0 supplemented with 1.0 mM DTT. Resuspended cells were passed through a French pressure cell twice to ensure >95% cell lysis. Lysed cells were centrifuged for 30 minutes at 12,000×g, and the supernatant was heated at 75° C. for 20 minutes, followed by quenching in an ice bath for 2 minutes. Precipitated protein was removed by centrifugation for 10 minutes at 11,000×g. SDS-PAGE indicated that the CE-7 enzyme comprised approximately 85-90% of the total protein in the heat-treated extract supernatant.

Example 9

Specific Activity and Perhydrolysis/Hydrolysis Ratio of *T. neapolitana* Acetyl Xylan Wild-Type Esterase and C277 Esterase Variants Reactions (40 mL total volume) were run at 25° C. in phosphate buffer (50 mM, pH 7.2) containing triacetin (100 mM), hydrogen peroxide (100 mM) and one of the following acetyl xylan esterase mutants: *T. neapolitana* C277S variant perhydrolase (0.010 mg/mL of heat-treated extract total protein from *E. coli* KLP18/pSW196/C277S), *T. neapolitana* C277T variant perhydrolase (0.010 mg/mL of heat-treated extract total protein from *E. coli* KLP18/pSW196/C277T), *T. neapolitana* C277A variant perhydrolase (0.0125 mg/mL of heat-treated extract total protein from *E. coli* KLP18/pSW196/C277A), and *T. neapolitana* C277V variant perhydrolase (0.0125 mg/mL of heat-treated extract total protein from *E. coli* KLP18/pSW196/C277V) (prepared as described in Example 8). Reactions were stirred for only the first 30 seconds of reaction to initially mix the reactants and enzyme.

A reaction was also run under identical conditions to that described immediately above using 0.050 mg/mL of heat-treated extract total protein isolated from *E. coli* KLP18/pSW196 (expressing *Thermotoga neapolitana* wild-type acetyl xylan esterase (Example 1)), where the heat-treated extract supernatant was prepared according to the procedure of Example 8.

Two samples from each of the reaction mixtures described above were simultaneously withdrawn after the first minute of each reaction, and every two minutes thereafter for fifteen minutes, where one of the two samples was analyzed for peracetic acid, and the second sample was analyzed for total acetic acid produced from both enzymatic hydrolysis of triacetin and from subsequent conversion of peracetic add in sample to acetic acid by reaction with methyl-p-tolyl sulfide (MTS, see below).

Measurement of the rate of peracetic acid production in the reaction mixture was performed using a modification of the method described by Karst et al., supra. A sample (0.040 mL) of the reaction mixture was removed at a predetermined time and immediately mixed with 0.960 mL of 5 mM phosphoric acid in water to terminate the reaction by adjusting the pH of the diluted sample to less than pH 4. The resulting solution was filtered using an ULTRAFREE® MC-filter unit (30,000 Normal Molecular Weight Limit (NMWL), Millipore Corp., Billerica, Mass.; cat #UFC3LKT 00) by centrifugation for 2 min at 12,000 rpm. An aliquot (0.100 mL) of the resulting filtrate was transferred to a 1.5-mL screw cap HPLC vial (Agilent Technologies, Palo Alto, Calif.; #5182-0715) containing 0.300 mL of deionized water, then 0.100 mL of 20 mM MTS (methyl-p-tolyl sulfide) in acetonitrile was added, the vial capped, and the contents briefly mixed prior to a 10 min incubation at ca. 25° C. in the absence of light. To the vial was then added 0.400 mL of acetonitrile and 0.100 mL of a solution of triphenylphosphine (TPP, 40 mM) in acetonitrile, the vial re-capped, and the resulting solution mixed and incubated at ca. 25° C. for 30 min in the absence of light. To the vial was then added 0.100 mL of 10 mM N,N-diethyl-m-toluamide (DEET; HPLC external standard) and the resulting solution analyzed by HPLC for MTSO (methyl-p-tolyl sulfoxide), the stoichiometric oxidation product produced by reaction of MTS with peracetic acid. A control reaction was run in the absence of added extract protein or triacetin to determine the rate of oxidation of MTS in the assay mixture by hydrogen peroxide, for correction of the rate of peracetic acid production for background MTS oxidation. HPLC method: Supelco Discovery C8 column (10-cm×4.0-mm, 5 μm) (catalog #569422-U) with Supelco Supelguard Discovery C8 precolumn (Sigma-Aldrich; catalog #59590-U); 10 microliter injection volume; gradient method with $CH_3CN$ (Sigma-Aldrich; catalog #270717) and deionized water at 1.0 mL/min and ambient temperature (Table 4).

TABLE 4

HPLC Gradient for analysis of peracetic acid.

| Time (min:sec) | (% $CH_3CN$) |
|---|---|
| 0:00 | 40 |
| 3:00 | 40 |
| 3:10 | 100 |
| 4:00 | 100 |
| 4:10 | 40 |
| 7:00 (stop) | 40 |

For determination of the rate of perhydrolase-catalyzed acetic acid production in the reaction, a sample (0.900 mL) of the reaction mixture was removed at a predetermined time and immediately added to a 1.5 mL-microcentrifuge tube containing 0.040 mL of 0.75 M $H_3PO_4$, and the resulting solution briefly mixed to terminate the reaction at pH 3.0-4.0. To the tube was then added 0.020 mL of a solution of 10 mg/mL of *Aspergillus niger* catalase (Sigma-Aldrich; C3515) in 50 mM phosphate buffer pH (7.2), and the resulting solution mixed and allowed to react for 15 minutes at ambient temperature to disproportionate unreacted hydrogen peroxide to water and oxygen. To the tube was then added 0.040 mL of 0.75 M $H_3PO_4$ and the resulting solution mixed and filtered using an ULTRAFREE® MC-filter unit (30,000 Normal Molecular Weight Limit (NMWL), Millipore Corp., cat #UFC3LKT 00) by centrifugation for 2 min at 12,000 rpm. An aliquot (0.100 mL) of the resulting filtrate was mixed with 0.150 mL of 20 mM MTS (methyl-p-tolyl sulfide) in acetonitrile, and the resulting solution was incubated for 10 min at ca. 25° C. in the absence of light. The concentration of acetic acid in the sample produced by both enzymatic hydrolysis of triacetin and conversion of peracetic acid to acetic acid by reaction with MTS was determined using a gas chromatograph (GC) equipped with a flame ionization detector (FID) and a DB-FFAP column (length, 15 m; ID, 0.530 mm; film thickness, 1.00 μm); a fresh injection port liner was employed for each rate determination (total of eight sample analyses) to avoid build up of phosphoric acid in the injection port liner over time.

The *Thermotoga neapolitana* acetyl xylan esterase variants had a significantly-higher specific activity for perhydrolysis of triacetin than the wild-type esterase (Table 5). The perhydrolysis/hydrolysis ratios for the *T. neapolitana* acetyl xylan esterase variants were determined by dividing the rate of PAA production (perhydrolysis rate) by the rate of hydrolysis of triacetin to acetic acid (hydrolysis rate) (calculated from the rate of total acetic acid production in the assay method from both PAA and acetic acid, and corrected for the rate of peracetic acid production); the P/H ratio of the *T. neapolitana* acetyl xylan esterase variants were ca. equal to or greater than the P/H ratio for the *T. neapolitana* wild-type acetyl xylan esterase (Table 5).

TABLE 5

| *Thermotoga neapolitana* perhydrolase | enzyme concen. (μg/mL) | perhydrolysis rate (mM/min) | hydrolysis rate (mM/min) | P/H ratio | specific activity (U/mg protein) |
|---|---|---|---|---|---|
| wild type | 50 | 3.61 | 1.22 | 3.0 | 72 |
| C277S | 10 | 4.40 | 1.61 | 2.7 | 440 |
| C277T | 10 | 4.24 | 0.81 | 5.2 | 424 |
| C277A | 12.5 | 4.14 | 1.43 | 2.9 | 331 |
| C277V | 12.5 | 3.70 | 0.88 | 4.2 | 296 |

Example 10

Cloning and Expression of Acetyl Xylan Esterase from *Thermotoga maritima*

A gene encoding acetyl xylan esterase from *T. maritima* as reported in GENBANK® (accession #NP_227893.1) was synthesized (DNA 2.0, Menlo Park Calif.). The gene was subsequently amplified by PCR (0.5 min at 94° C., 0.5 min at 55° C., 1 min at 70° C., 30 cycles) using primers identified as SEQ ID NO: 206 and SEQ ID NO: 207. The resulting nucleic acid product (SEQ ID NO: 208) was cut with restriction enzymes PstI and XbaI and subcloned between the PstI and XbaI sites in pUC19 to generate the plasmid identified as pSW207. A gene encoding an acetyl xylan esterase from *T. maritima* MSB8 as reported in GENBANK® (Accession no. NP_227893.1; SEQ ID NO: 36) was synthesized using codons optimized for expression in *E. coli* (DNA 2.0, Menlo Park Calif.). The gene was subsequently amplified by PCR (0.5 min at 94° C., 0.5 min at 55° C., 1 min at 70° C., 30 cycles) using primers identified as SEQ ID NO:38 and SEQ ID NO:39. The resulting nucleic acid product (SEQ ID NO: 37) was cut with restriction enzymes EcoRI and PstI and subcloned between the EcoRI and PstI sites in pTrc99A (GENBANK® Accession no. M22744) to generate the plasmid identified as pSW228 (containing the codon-optimized *T. maritima* coding sequence SEQ ID NO: 41). The plasmids pSW207 and pSW228 were used to transform *E. coli* KLP18 (U.S. Patent Application Pub. No. 2008/0176299) to generate the strain identified as KLP18/pSW207 and KLP18/pSW228, respectively. KLP18/pSW207 and KLP18/pSW228 were gown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 11

Construction of *Thermotoga maritima* Acetyl Xylan Esterase Variants at Residue C277

The C277 (Cys277) position of *T. maritima* acetyl xylan esterase was changed to each of Val, Ala, Ser and Thr using oligonucleotide primer pairs (Table 6) that were designed based on the codon optimized sequence of *T. maritima* acetyl xylan esterase (SEQ ID NO:41) in the plasmid pSW228. The mutations were made using QUIKCHANGE® (Stratagene) according to the manufacturer's instructions. Amplified plasmids were treated with 1 U of DpnI at 37° C. for 1 hour. Treated plasmids were used to transform chemically competent *E. coli* XL1-Blue (Stratagene). Transformants were plated on LB-agar supplemented with 0.1 mg ampicillin/mL and grown overnight at 37° C. Up to five individual colonies were picked and the plasmid DNA sequenced to confirm the expected mutations.

Example 12

Expression of *Thermotoga maritima* Acetyl Xylan Esterase Variants in *E. coli* KLP18

Plasmids with confirmed acetyl xylan esterase mutations were used to transform *E. coli* KLP18 (Example 1). Transformants were grown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the acetyl xylan esterase at 20-40% of total soluble protein.

Example 13

Preparation of Cell Lysates Containing Semi-Purified *T. Maritime* Acetyl Xylan Esterase Mutants Cell cultures (prepared as described in Example 12) were grown using a fermentation protocol similar to that described in Example 7 at a 1-L scale (Applikon). Cells were harvested by centrifugation at 5,000×g for 15 minutes then resuspended (20% w/v) in 50 mM phosphate buffer pH 7.0 supplemented with 1.0 mM DTT. Resuspended cells were passed through a French pressure cell twice to ensure >95% cell lysis. Lysed cells were centrifuged for 30 minutes at 12,000×g, and the supernatant was heated at 75° C. for 20 minutes, followed by quenching in an ice bath for 2 minutes. Precipitated protein was removed by centrifugation for 10 minutes at 11,000×g. SDS-PAGE indicated that the CE-7 enzyme comprised approximately 85-90% of the total protein in the preparation.

Example 14

Specific Activity and Perhydrolysis/Hydrolysis Ratio of *T. maritima* Acetyl Xylan Wild-Type Esterase and C277 Esterase Variants Reactions (40 mL total volume) were run at 25° C. in phosphate buffer (50 mM, pH 7.2) containing triacetin (100 mM), hydrogen peroxide (100 mM) and one of the following acetyl xylan esterase variants: *T. maritima* C277S variant perhydrolase (0.010 mg/mL of heat-treated extract total protein from *E. coli* KLP18/pSW228/C277S), *T. maritima* C277T variantperhydrolase (0.010 mg/mL of heat-treated extract total protein from *E. coli* KLP18/pSW228/C277T), *T. maritima* C277A variant perhydrolase (0.0125 mg/mL of heat-treated extract total protein from *E. coli* KLP18/pSW228/C277A), and *T. maritima* C277V variant perhydrolase (0.0125 mg/mL of heat-treated extract total protein from *E. coli* KLP18/pSW228/C277V) (prepared as described in Example 13). Reactions were stirred for only the first 30 seconds of reaction to initially mix the reactants and enzyme.

A reaction was also run under identical conditions to that described immediately above using 0.050 mg/mL of heat-treated extract total protein isolated from *E. coli* KLP18/pSW228 (expressing *Thermotoga maritima* wild-type acetyl xylan esterase (Example 10)), where the heat-treated extract supernatant was prepared according to the procedure of Example 13.

Two samples from each of the reaction mixtures described above were simultaneously withdrawn after the first minute

TABLE 6

Oligonucleotides used to change residue 277 in T. maritima.

| | forward 5' to 3' | | reverse 5' to 3' |
|---|---|---|---|
| Tma_C277Vf (SEQ ID NO: 194) | ggacaacatcGTGcctccttcta | Tma_C277Vr (SEQ ID NO: 195) | TAGAAGGAGG<u>CAC</u>GATGTTGTCC |
| Tma_C277Af (SEQ ID NO: 196) | ggacaacatcGCGcctccttcta | Tma_C277Ar (SEQ ID NO: 197) | TAGAAGGAGG<u>CGC</u>GATGTTGTCC |
| Tma_C277Sf (SEQ ID NO: 198) | ggacaacatcTCAcctccttcta | Tma_C277Sr (SEQ ID NO: 199) | TAGAAGGAGG<u>TGA</u>GATGTTGTCC |
| Tma_C277Tf (SEQ ID NO: 200) | ggacaacatcACCcctccttcta | Tma_C277Tr (SEQ ID NO: 201) | TAGAAGGAGG<u>GGT</u>GATGTTGTCC | of each reaction, and every two minutes thereafter for fifteen minutes, where one of the two samples was analyzed for peracetic acid using a modification of the method described by Karst et al., supra, and the second sample was analyzed for total acetic acid produced from both enzymatic hydrolysis of triacetin and from subsequent conversion of peracetic acid in sample to acetic acid by reaction with methyl-p-tolyl sulfide (MTS) (see Example 9).

The *Thermotoga maritima* acetyl xylan esterase mutants had a significantly-higher specific activity for perhydrolysis of triacetin than the wild-type esterase (Table 7). The perhydrolysis/hydrolysis ratios for the *T. maritima* acetyl xylan esterase variants were determined by dividing the rate of PAA production (perhydrolysis rate) by the rate of hydrolysis of triacetin to acetic acid (hydrolysis rate) (calculated from the rate of total acetic acid production in the assay method from both PAA and acetic acid, and corrected for the rate of peracetic acid production); the P/H ratio of the *T. maritima* acetyl xylan esterase variants were ca. equal to or greater than the P/H ratio for the *T. neapolitana* wild-type acetyl xylan esterase (Table 7).

TABLE 7

| *Thermotoga maritima* perhydrolase | enzyme concen. (μg/mL) | perhydrolysis rate (mM/min) | hydrolysis rate (mM/min) | P/H ratio | specific activity (U/mg protein) |
|---|---|---|---|---|---|
| wild type | 50 | 3.06 | 0.47 | 6.5 | 61 |
| C277S | 10 | 7.77 | 0.48 | 16 | 777 |
| C277T | 10 | 6.93 | 1.05 | 6.6 | 693 |
| C277A | 10 | 4.27 | 0.088 | 48 | 427 |
| C277V | 10 | 4.25 | 0.062 | 68 | 425 |

Example 15

Peracetic Acid Production Using Perhydrolases

Reactions (100 mL total volume) containing triacetin (2 mM), hydrogen peroxide (10 mM) and from 0.1 μg/mL to 2.0 μg/mL heat-treated cell extract protein (prepared as described above, where the heat-treatment was performed at 85° C. for 20 min) were run in 10 mM sodium bicarbonate buffer (initial pH 8.1) at 20° C. Determination of the concentration of peracetic acid in the reaction mixtures was performed according to the method described by Karst et al., supra. The peracetic acid concentrations produced in 1 min, 5 min, 20 min, 40 min and 60 min are listed in Table 8.

TABLE 8

Dependence of peracetic acid (PAA) concentration on perhydrolase concentration in reactions containing triacetin (2 mM) and hydrogen peroxide (10 mM) in sodium bicarbonate buffer (10 mM, initial pH 8.1) at 20° C., using heat-treated extract protein from *E. coli* KLP18/pSW228 (*Thermotoga maritima* wild-type perhydrolase) or *E. coli* KLP18/pSW228/C277S (*Thermotoga maritima* C277S variant perhydrolase) (duplicate reactions).

| *Thermotoga maritima* perhydrolase | triacetin (mM) | enzyme concen. (μg/mL) | PAA, 1 min (ppm) | PAA, 5 min (ppm) | PAA, 20 min (ppm) | PAA, 40 min (ppm) | PAA, 60 min (ppm) |
|---|---|---|---|---|---|---|---|
| no enzyme | 2 | 0 | 0 | 0 | 1 | 1 | 3 |
| wild type | 2 | 0.2 | 0 | 2 | 7 | 13 | 19 |
| wild type | 2 | 0.2 | 0 | 1 | 5 | 11 | 15 |
| wild type | 2 | 0.5 | 0 | 2 | 12 | 19 | 25 |
| wild type | 2 | 0.5 | 0 | 2 | 12 | 21 | 26 |
| wild type | 2 | 1.0 | 0 | 5 | 20 | 29 | 31 |
| wild type | 2 | 1.0 | 0 | 5 | 19 | 30 | 31 |
| wild type | 2 | 2.0 | 1 | 11 | 24 | 24 | 20 |
| wild type | 2 | 2.0 | 1 | 11 | 29 | 29 | 21 |
| C277S | 2 | 0.2 | 0 | 4 | 18 | 18 | 18 |
| C277S | 2 | 0.2 | 0 | 4 | 18 | 17 | 18 |
| C277S | 2 | 0.5 | 1 | 12 | 39 | 54 | 64 |
| C277S | 2 | 0.5 | 1 | 10 | 34 | 52 | 64 |
| C277S | 2 | 1.0 | 18 | 26 | 59 | 69 | 63 |
| C277S | 2 | 1.0 | 18 | 25 | 60 | 70 | 64 |
| C277S | 2 | 2.0 | 9 | 38 | 66 | 60 | 48 |
| C277S | 2 | 2.0 | 9 | 34 | 69 | 61 | 49 |

Example 16

Peracetic Acid Production Using Perhydrolases

Reactions (100 mL total volume) containing triacetin (20 mM), hydrogen peroxide (10 mM) and from 0.1 μg/mL to 2.0 μg/mL heat-treated cell extract protein (prepared as described above, where the heat-treatment was performed at 85° C. for 20 min) were run in 10 mM sodium bicarbonate buffer (initial pH 8.1) at 20° C. Determination of the concentration of peracetic acid in the reaction mixtures was performed according to the method described by Karst et al., supra. The peracetic acid concentrations produced in 1 min, 5 min, 20 min, 40 min and 60 min are listed in Table 9.

TABLE 9

Dependence of peracetic acid (PAA) concentration on perhydrolase concentration in reactions containing triacetin (20 mM) and hydrogen peroxide (10 mM) in sodium bicarbonate buffer (10 mM, initial pH 8.1) at 20° C., using heat-treated extract protein from *E. coli* KLP18/pSW228 (*Thermotoga maritima* wild-type perhydrolase) or *E. coli* KLP18/pSW228/C277S (*Thermotoga maritima* C277S variant perhydrolase) (duplicate reactions).

| *Thermotoga maritima* perhydrolase | triacetin (mM) | enzyme concen. (µg/mL) | PAA, 1 min (ppm) | PAA, 5 min (ppm) | PAA, 20 min (ppm) | PAA, 40 min (ppm) | PAA, 60 min (ppm) |
|---|---|---|---|---|---|---|---|
| no enzyme | 20 | 0 | 2 | 3 | 3 | 7 | 9 |
| wild-type | 20 | 0.2 | 3 | 10 | 15 | 27 | 35 |
| wild-type | 20 | 0.2 | 4 | 9 | 19 | 32 | 41 |
| wild-type | 20 | 0.5 | 3 | 9 | 21 | 39 | 52 |
| wild-type | 20 | 0.5 | 3 | 8 | 22 | 39 | 54 |
| wild-type | 20 | 1.0 | 4 | 13 | 35 | 62 | 82 |
| wild-type | 20 | 1.0 | 4 | 12 | 37 | 67 | |
| wild-type | 20 | 2.0 | 9 | 20 | 52 | 91 | 122 |
| wild-type | 20 | 2.0 | 10 | 20 | 52 | 87 | 114 |
| C277S | 20 | 0.2 | 7 | 16 | 67 | 109 | 148 |
| C277S | 20 | 0.2 | 9 | 24 | 67 | 112 | 144 |
| C277S | 20 | 0.5 | 16 | 43 | 140 | 202 | 260 |
| C277S | 20 | 0.5 | 17 | 48 | 148 | 228 | 272 |
| C277S | 20 | 1.0 | 24 | 75 | 230 | 289 | 353 |
| C277S | 20 | 1.0 | 26 | 97 | 232 | 297 | 372 |
| C277S | 20 | 2.0 | 32 | 130 | 318 | 402 | 443 |
| C277S | 20 | 2.0 | 37 | 135 | 323 | 401 | 430 |

Example 17

Peracetic Acid Production Using Perhydrolases

Reactions (40 mL total volume) were run at 25° C. in phosphate buffer (50 mM, pH 7.2) containing triacetin (100 mM), hydrogen peroxide (100 mM) and from 10 µg/mL to 50 µg/mL of heat-treated *T. neapolitana* or *T. maritima* wild-type or C277 variant perhydrolases (as heat-treated cell extract protein prepared as described above, where the heat-treatment was performed at 75° C. for 20 min). Reactions were stirred for only the first 30 seconds of reaction to initially mix the reactants and enzyme. Determination of the concentration of peracetic acid in the reaction mixtures was performed according to the method described by Karst et al., supra. The peracetic acid concentrations produced in 1 min, 5 min, and 30 min are listed in Table 10.

Example 18

Peracetic Acid Production Using Perhydrolases

Reactions (10 mL total volume) were run at 25° C. in sodium bicarbonate buffer (1 mM, initial pH 6.0) containing triacetin (100 mM or 150 mM), hydrogen peroxide (100 mM, 250 mM or 420 mM) and heat-treated *T. neapolitana* or *T. maritima* wild-type, C277S or C277T vacant perhydrolases (as heat-treated cell extract protein prepared as described above, where the heat-treatment was performed at 75° C. for 20 min; concentrations as listed in Table 11). Reactions run using 420 mM hydrogen peroxide additionally contained 500 ppm TURPINAL® SL. Reactions were stirred for only the first 30 seconds of reaction to initially mix the reactants and enzyme. Determination of the concentration of peracetic acid in the reaction mixtures was performed according to the method described by Karst et al., supra. The peracetic acid concentrations produced in 1 min, 5 min, and 30 min are listed in Table 11.

TABLE 10

Peracetic acid (PAA) production in reactions containing triacetin (100 mM) and hydrogen peroxide (100 mM) in phosphate buffer (50 mM, pH 7.2) at 25° C., using heat-treated *T. neapolitana* or *T. maritima* wild-type or C277 mutant perhydrolases.

| perhydrolase | triacetin (mM) | $H_2O_2$ (mM) | enzyme concen. (µg/mL) | PAA, 1 min (ppm) | PAA, 5 min (ppm) | PAA, 30 min (ppm) |
|---|---|---|---|---|---|---|
| no enzyme | 100 | 100 | 0 | 63 | 54 | 80 |
| *T. maritima* wild-type | 100 | 100 | 50 | 529 | 1790 | 3785 |
| *T. maritima* C277S | 100 | 100 | 10 | 979 | 3241 | 4635 |
| *T. maritima* C277T | 100 | 100 | 10 | 933 | 2882 | 3527 |
| *T. maritima* C277A | 100 | 100 | 10 | 442 | 2018 | 2485 |
| *T. maritima* C277V | 100 | 100 | 10 | 577 | 1931 | 2278 |
| *T. neapolitana* wild-type | 100 | 100 | 50 | 514 | 1837 | 3850 |
| *T. neapolitana* C277S | 100 | 100 | 10 | 606 | 2237 | 4609 |
| *T. neapolitana* C277T | 100 | 100 | 10 | 634 | 2198 | 3918 |
| *T. neapolitana* C277A | 100 | 100 | 12.5 | 516 | 2041 | 3735 |
| *T. neapolitana* C277V | 100 | 100 | 12.5 | 451 | 1813 | 2758 |

TABLE 11

Peracetic acid (PAA) production in reactions containing triacetin and hydrogen peroxide in bicarbonate buffer (1 mM at pH 6.0 or 100 mM at pH 8.1) or in deionized water (pH 5.0) at 25° C. using heat-treated *T. maritima* wild-type, C277S or C277T variant perhydrolases.

| Thermotoga maritima perhydrolase | triacetin (mM) | $H_2O_2$ (mM) | $NaHCO_3$ buffer (mM) | enzyme concen. (μg/mL) | PAA, 1 min (ppm) | PAA, 5 min (ppm) | PAA, 30 min (ppm) |
|---|---|---|---|---|---|---|---|
| no enzyme | 100 | 100 | 1.0 | 0 | 28 | 78 | 141 |
| wild-type | 100 | 100 | 1.0 | 75 | 434 | 494 | 608 |
| wild-type | 100 | 100 | 1.0 | 100 | 449 | 667 | 643 |
| C277S | 100 | 100 | 1.0 | 15 | 989 | 1554 | 1476 |
| C277S | 100 | 100 | 1.0 | 20 | 1301 | 2139 | 2131 |
| C277T | 100 | 100 | 1.0 | 15 | 1062 | 1513 | 1393 |
| C277T | 100 | 100 | 1.0 | 20 | 996 | 1430 | 1516 |
| no enzyme | 100 | 250 | 0 | 0 | 13 | 71 | 71 |
| wild-type | 100 | 250 | 0 | 75 | 512 | 535 | 533 |
| wild-type | 100 | 250 | 0 | 100 | 576 | 668 | 654 |
| C277S | 100 | 250 | 0 | 15 | 653 | 671 | 675 |
| C277S | 100 | 250 | 0 | 20 | 943 | 927 | 903 |
| C277T | 100 | 250 | 0 | 15 | 717 | 711 | 765 |
| C277T | 100 | 250 | 0 | 20 | 730 | 755 | 743 |
| no enzyme | 150 | 420 | 100 | 0 | 417 | 810 | 848 |
| wild-type | 150 | 420 | 100 | 500 | 6303 | 8627 | 9237 |
| C277S | 150 | 420 | 100 | 100 | 7822 | 10349 | 10197 |

Example 19

Perhydrolysis of Propylene Glycol Diacetate or Ethylene Glycol Diacetate Using *T. maritima* and *T. neapolitana* Wild-Type and Variant Perhydrolases Cell extracts of transformants expressing *Thermotoga neapolitana* wild-type perhydrolase (KLP18/pSW196), *Thermotoga neapolitana* C277S variant perhydrolase (KLP18/pSW196/C277S), *Thermotoga neapolitana* C277T variant perhydrolase (KLP18/pSW196/C277T), *Thermotoga maritima* wild-type perhydrolase (KLP18/pSW228), *Thermotoga maritima* C277S variant perhydrolase (KLP18/pSW228/C277S), and *Thermotoga maritima* C277T variant perhydrolase (KLP18/pSW228/C277T) were each prepared by passing a suspension of cell paste (20 wt % wet cell weight) in 0.05 M potassium phosphate buffer (pH 7.0) containing dithiothreitol (1 mM) twice through a French press having a working pressure of 16,000 psi (~110 MPa). The lysed cells were centrifuged for 30 minutes at 12,000×g, producing a clarified cell extract that was assayed for total soluble protein (Bradford assay). The supernatant was heated at 75° C. for 20 minutes, followed by quenching in an ice bath for 2 minutes. Precipitated protein was removed by centrifugation for 10 minutes at 11,000×g. SDS-PAGE of the resulting heat-treated extract protein supernatant indicated that the CE-7 enzyme comprised approximately 85-90% of the total protein in the preparation. The heat-treated extract protein supernatant was frozen in dry ice and stored at −80° C. until use.

A first set of reactions (10 mL total volume) were run at 20° C. in 10 mM sodium bicarbonate buffer (initial pH 8.1) containing propylene glycol diacetate (PGDA) or ethylene glycol diacetate (EGDA) (100 mM), hydrogen peroxide (100 mM) and 25 μg/mL of heat-treated extract protein from one of *E. coli* KLP18/pSW196 (*Thermotoga neapolitana* wild-type perhydrolase), *E. coli* KLP18/pSW196/C277S (*Thermotoga neapolitana* C277S variant perhydrolase), *E. coli* KLP18/pSW196/C277T (*Thermotoga neapolitana* C277T variant perhydrolase), *E. coli* KLP18/pSW228 (*Thermotoga maritima* wild-type perhydrolase), *E. coli* KLP18/pSW228/C277S (*Thermotoga maritima* C277S variant perhydrolase), and *E. coli* KLP18/pSW228/C277T (*Thermotoga maritima* C277T variant perhydrolase) (prepared as described above). A control reaction for each reaction condition was run to determine the concentration of peracetic acid produced by chemical perhydrolysis of triacetin by hydrogen peroxide in the absence of added extract protein. The reactions were sampled at 1, 5, and 30 minutes and the samples analyzed for peracetic acid using the Karst derivatization protocol (Karst et al., supra) and HPLC analytical method (supra). The peracetic acid concentrations produced in 1 min, 5 min and 30 min are listed in Table 12.

TABLE 12

Peracetic acid (PAA) concentration produced utilizing *T. maritima* and *T. neapolitana* wild-type and variant perhydrolases in reactions at 20° C. in sodium bicarbonate buffer (10 mM, initial pH 8.1) containing propylene glycol diacetate (PGDA) (100 mM) or ethylene glycol diacetate (EGDA) (100 mM), hydrogen peroxide (100 mM) and 25 μg/mL of heat-treated extract protein.

| perhydrolase | substrate | substrate conc. (mM) | $H_2O_2$ (mM) | PAA, 1 min (ppm) | PAA, 5 min (ppm) | PAA, 30 min (ppm) |
|---|---|---|---|---|---|---|
| no enzyme (control) | PGDA | 100 | 100 | 0 | 15 | 165 |
| *T. maritima* WT | PGDA | 100 | 100 | 534 | 1104 | 1695 |
| *T. maritima* C277S | PGDA | 100 | 100 | 647 | 1320 | 1864 |
| *T. maritima* C277T | PGDA | 100 | 100 | 656 | 1174 | 1418 |
| *T. neapolitana* WT | PGDA | 100 | 100 | 513 | 1052 | 1946 |

TABLE 12-continued

Peracetic acid (PAA) concentration produced utilizing T. maritima and T. neapolitana wild-type and variant perhydrolases in reactions at 20° C. in sodium bicarbonate buffer (10 mM, initial pH 8.1) containing propylene glycol diacetate (PGDA) (100 mM) or ethylene glycol diacetate (EGDA) (100 mM), hydrogen peroxide (100 mM) and 25 µg/mL of heat-treated extract protein.

| perhydrolase | substrate | substrate conc. (mM) | $H_2O_2$ (mM) | PAA, 1 min (ppm) | PAA, 5 min (ppm) | PAA, 30 min (ppm) |
|---|---|---|---|---|---|---|
| T. neapolitana C277S | PGDA | 100 | 100 | 875 | 1327 | 1707 |
| T. neapolitana C277T | PGDA | 100 | 100 | 724 | 1325 | 1864 |
| no enzyme (control) | EGDA | 100 | 100 | 0 | 70 | 229 |
| T. maritima WT | EGDA | 100 | 100 | 765 | 1182 | 1595 |
| T. maritima C277S | EGDA | 100 | 100 | 725 | 1240 | 1724 |
| T. maritima C277T | EGDA | 100 | 100 | 802 | 1218 | 1734 |
| T. neapolitana WT | EGDA | 100 | 100 | 603 | 1132 | 1643 |
| T. neapolitana C277S | EGDA | 100 | 100 | 680 | 1305 | 1698 |
| T. neapolitana C277T | EGDA | 100 | 100 | 688 | 1164 | 1261 |

A second set of reactions (10 mL total volume) were run at 20° C. in 10 mM sodium bicarbonate buffer (initial pH 8A) containing propylene glycol diacetate (PGDA) or ethylene glycol diacetate (EGDA) (2 mM), hydrogen peroxide (10 mM) and 10 µg/mL of heat-treated extract protein from one of E. coli KLP18/pSW196 (*Thermotoga neapolitana* wild-type perhydrolase), E. coli KLP18/pSW196/C277S (*Thermotoga neapolitana* C277S variant perhydrolase), E. coli KLP18/pSW196/C277T (*Thermotoga neapolitana* C277T variant perhydrolase), E. coli KLP18/pSW228 (*Thermotoga maritima* wild-type perhydrolase), E. coli KLP18/pSW228/C277S (*Thermotoga maritima* C277S variant perhydrolase), and E. coli KLP18/pSW228/C277T (*Thermotoga maritima* C277T variant perhydrolase) (prepared as described above). A control reaction for each reaction condition was run to determine the concentration of peracetic acid produced by chemical perhydrolysis of triacetin by hydrogen peroxide in the absence of added extract protein. The reactions were sampled at 5 minutes and the samples analyzed for peracetic acid using the Karst derivatization protocol (Karst et al., supra) and HPLC analytical method (supra). The peracetic acid concentrations produced in 5 min are listed in Table 13.

TABLE 13

Peracetic acid (PAA) concentration produced utilizing T. maritima and T. neapolitana wild-type and variant perhydrolases in reactions at 20° C. in sodium bicarbonate buffer (10 mM, initial pH 8.1) containing propylene glycol diacetate (PGDA) (2 mM) or ethylene glycol diacetate (EGDA) (2 mM), hydrogen peroxide (10 mM) and 10 µg/mL of heat-treated extract protein.

| perhydrolase | substrate | substrate conc. (mM) | $H_2O_2$ (mM) | PAA, 5 min (ppm) |
|---|---|---|---|---|
| no enzyme (control) | PGDA | 2 | 10 | 3.6 |
| T. maritima WT | PGDA | 2 | 10 | 5.0 |
| T. maritima C277S | PGDA | 2 | 10 | 7.2 |
| T. maritima C277T | PGDA | 2 | 10 | 7.9 |
| T. neapolitana WT | PGDA | 2 | 10 | 5.7 |
| T. neapolitana C277S | PGDA | 2 | 10 | 7.9 |
| T. neapolitana C277T | PGDA | 2 | 10 | 3.9 |
| no enzyme (control) | EGDA | 2 | 10 | 3.3 |
| T. maritima WT | EGDA | 2 | 10 | 9.9 |
| T. maritima C277S | EGDA | 2 | 10 | 13.6 |
| T. maritima C277T | EGDA | 2 | 10 | 22.9 |
| T. neapolitana WT | EGDA | 2 | 10 | 6.6 |
| T. neapolitana C277S | EGDA | 2 | 10 | 18.4 |
| T. neapolitana C277T | EGDA | 2 | 10 | 20.2 |

What is claimed is:

1. An isolated polypeptide having perhydrolysis activity and being structurally classified as a carbohydrate esterase family 7 enzyme, said polypeptide having at least 95% amino acid sequence identity to SEQ ID NO: 5, provided that a substitution to amino acid 277 of SEQ ID NO: 5 is selected from the group consisting of serine, threonine, valine, and alanine, wherein said polypeptide has improved activity for production of an efficacious concentration of percarboxylic acid for disinfection relative to wild-type *Thermotoga neapolitana* acetyl xylan esterase of SEQ ID NO:32; improved activity across the entire pH range of activity relative to wild-type *Thermotoga neapolitana* acetyl xylan esterase of SEQ ID NO:32; improved perhydrolysis/hydrolysis ratio relative to wild-type *Thermotoga neapolitana* acetyl xylan esterase of SEQ ID NO:32; or a combination thereof.

2. The isolated polypeptide of claim 1, wherein the polypeptide comprises the amino acid sequence of SEQ ID NO: 5.

3. A process for producing a peroxycarboxylic acid from a carboxylic acid ester comprising (a) providing a set of reaction components, said components comprising:
  (1) a carboxylic acid ester selected from the group consisting of:
    (i) one or more esters having the structure $[X]_m R_5$ wherein
    X is an ester group of the formula $R_6C(O)O$;
    $R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;
    $R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;

m is 1 to the number of carbon atoms in $R_5$, said one or more esters having solubility in water of at least 5 ppm at 25° C.;

(ii) one or more glycerides having the structure

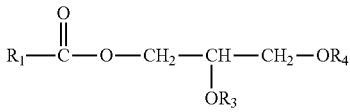

wherein $R_1$ is a C1 to C7 straight chain or branched chain alkyl optionally substituted with an hydroxyl or a C1 to C4 alkoxy group and $R_3$ and $R_4$ are individually H or $R_1C(O)$;

(iii) one or more esters of the formula

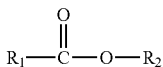

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10;

(iv) one or more acetylated monosaccharides, acetylated disaccharides, or acetylated polysaccharides; and (v) any combination of (i) through (iv);

(2) a source of peroxygen; and (3) the polypeptide of claim 1; and (b) combining said reaction components under suitable aqueous reaction conditions whereby a peroxycarboxylic acid is produced.

4. A process to disinfect or sanitize a hard surface or inanimate object using an enzymatically-produced peroxycarboxylic acid composition, said process comprising:

(a) providing a set of reaction components, said components comprising:

(1) a carboxylic acid ester selected from the group consisting of:

(i) one or more esters having the structure $[X]_mR_5$ wherein

X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;

m is 1 to the number of carbon atoms in $R_5$, said one or more esters having solubility in water of at least 5 ppm at 25° C.;

(ii) one or more glycerides having the structure

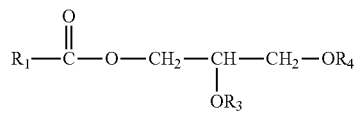

wherein $R_1$ is a C1 to C7 straight chain or branched chain alkyl optionally substituted with an hydroxyl or a C1 to C4 alkoxy group and $R_3$ and $R_4$ are individually H or $R_1C(O)$;

(iii) one or more esters of the formula

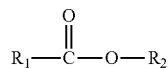

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10;

(iv) one or more acetylated monosaccharides, acetylated disaccharides, or acetylated polysaccharides; and (v) any combination of (i) through (iv);

(2) a source of peroxygen; and (3) the polypeptide of claim 1;

(b) combining said reaction components under suitable aqueous reaction conditions whereby a peroxycarboxylic acid product is formed;

(c) optionally diluting said peroxycarboxylic acid product; and (d) contacting said hard surface or inanimate object with the peroxycarboxylic acid produced in step (b) or step (c) whereby said surface or said inanimate object is disinfected or sanitized.

5. A process for treating an article of clothing or a textile for bleaching, stain removal, odor reduction, sanitization or disinfection using an enzymatically-produced peroxycarboxylic acid composition, said process comprising:

(a) providing a set of reaction components, said components comprising:

(1) a carboxylic acid ester selected from the group consisting of:

(i) one or more esters having the structure $[X]_mR_5$ wherein

X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;

m is 1 to the number of carbon atoms in $R_5$,
said one or more esters having solubility in water of
at least 5 ppm at 25° C.;
(ii) one or more glycerides having the structure

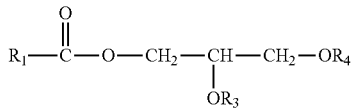

wherein $R_1$ is a C1 to C7 straight chain or branched chain alkyl optionally substituted with an hydroxyl or a C1 to C4 alkoxy group and $R_3$ and $R_4$ are individually H or $R_1C(O)$;
(iii) one or more esters of the formula

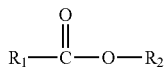

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10;
(iv) one or more acetylated monosaccharides, acetylated disaccharides, or acetylated polysaccharides; and
(v) any combination of (i) through (iv);
(2) a source of peroxygen; and
(3) the polypeptide of claim 1;
(b) combining said reaction components under suitable aqueous reaction conditions whereby a peroxycarboxylic acid product is formed;
(c) optionally diluting said peroxycarboxylic acid product; and
(d) contacting said article of clothing or textile with the peroxycarboxylic acid produced in step (b) or step (c);
wherein said article of clothing or textile is destained, deodorized, disinfected, bleached, or a combination thereof.

6. A peroxycarboxylic acid generating system comprising:
(a) a substrate selected from the group consisting of:
(i) one or more esters having the structure $$[X]_mR_5$$

wherein
X is an ester group of the formula $R_6C(O)O$;
$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;
$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;
m is 1 to the number of carbon atoms in $R_5$,
said one or more esters having solubility in water of at least 5 ppm at 25° C.;

(ii) one or more glycerides having the structure

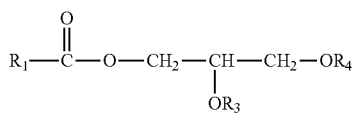

wherein $R_1$ is a C1 to C7 straight chain or branched chain alkyl optionally substituted with an hydroxyl or a C1 to C4 alkoxy group and $R_3$ and $R_4$ are individually H or $R_1C(O)$;
(iii) one or more esters of the formula

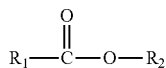

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10;
(iv) one or more acetylated monosaccharides, acetylated disaccharides, or acetylated polysaccharides; and
(v) any combination of (i) through (iv);
(b) a source of peroxygen; and
(c) the polypeptide of claim 1.

7. A formulation comprising:
(a) a first mixture comprising an enzyme catalyst comprising the polypeptide of claim 1 and a carboxylic acid ester selected from the group consisting of monoacetin, diacetin, triacetin and mixtures thereof; said first mixture optionally comprising an inorganic or organic buffer, a corrosion inhibitor, a wetting agent or a combination thereof; and
(b) a second mixture comprising a source of peroxygen and water, said second mixture optionally further comprising a hydrogen peroxide stabilizer.

8. A formulation comprising:
(a) a first mixture comprising a enzyme catalyst comprising the polypeptide of claim 1 and an acetylated saccharide selected from the group consisting of acetylated monosaccharides, acetylated disaccharides, acetylated polysaccharides, and combinations thereof, said first mixture optionally further comprising an inorganic or organic buffer, a corrosion inhibitor, a wetting agent, or a combination thereof; and
(b) a second mixture comprising a source of peroxygen and water, said second mixture optionally comprising a hydrogen peroxide stabilizer.

9. A process to provide a benefit to an article of clothing or textile using an enzymatically-produced peroxycarboxylic acid composition, said process comprising:
(a) providing a set of reaction components, said components comprising:
(1) a carboxylic acid ester selected from the group consisting of:
(i) one or more esters having the structure $$[X]_mR_5$$

wherein
X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;

m is 1 to the number of carbon atoms in $R_5$, said one or more esters having solubility in water of at least 5 ppm at 25° C.;

(ii) one or more glycerides having the structure

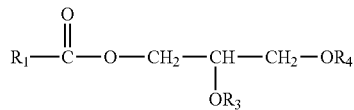

wherein $R_1$ is a C1 to C7 straight chain or branched chain alkyl optionally substituted with an hydroxyl or a C1 to C4 alkoxy group and $R_3$ and $R_4$ are individually H or $R_1C(O)$;

(iii) one or more esters of the formula

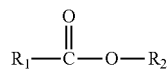

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10;

(iv) one or more acetylated monosaccharides, acetylated disaccharides, or acetylated polysaccharides; and (v) any combination of (i) through (iv);

(2) a source of peroxygen; and (3) the polypeptide of claim 1;

(b) combining said reaction components under suitable aqueous reaction conditions whereby a peroxycarboxylic acid product is formed;

(c) optionally diluting said peroxycarboxylic acid product; and (d) contacting said article of clothing or textile with the peroxycarboxylic acid produced in step (b) or step (c) whereby said article of clothing or textile receives a benefit selected from the group consisting of bleaching, destaining, deodorizing, disinfecting, sanitizing, and a combination thereof.

* * * * *

SEQUENCE LISTING

```
<160> NUMBER OF SEQ ID NOS: 208

<210> SEQ ID NO 1
<211> LENGTH: 978
<212> TYPE: DNA
<213> ORGANISM: Thermotoga neapolitana
<220> FEATURE:
<221> NAME/KEY: misc_feature
<222> LOCATION: (831)..(831)
<223> OTHER INFORMATION: n is a, g, c, or t.

<400> SEQUENCE: 1
atggccttct tcgatatgcc ccttgaggaa ctgaaaaagt accggcctga aaggtacgag      60
gagaaagatt tcgatgagtt ctggagggaa acacttaaag aaagcgaagg attccctctg     120
gatcccgtct ttgaaaaggt ggactttcat ctcaaaacgg ttgaaacgta cgatgttact     180
ttctctggat acaggggggca gagaataaag ggctggcttc ttgttccgaa gttggcggaa     240
```

```
gaaaagcttc catgcgtcgt gcagtacata ggttacaatg gtggaagggg ttttccacac    300
gactggctgt tctggccgtc aatgggttac atctgttttg tcatggacac caggggggcag    360 ggaagcggct ggatgaaggg agacacaccg gattaccctg aggtccagt cgatccacag    420 taccccggat tcatgacgag gggcattctg gatccgggaa cctattacta caggcgagtc    480
ttcgtggatg cggtcagggc ggtggaagca gccatttcct tcccgagagt ggattccagg    540
aaggtggtgg tggccggagg cagtcagggt gggggaatcg cccttgcggt gagtgccctg    600
tcgaacaggg tgaaggctct gctctgcgat gtgccgtttc tgtgccactt cagaagggcc    660
gtgcaacttg tcgacacaca cccatacgtg gagatcacca acttcctcaa aacccacagg    720
gacaaagagg agattgtttt cagaacactt tcctacttcg atggtgtgaa ctttgcagca    780
agggcaaagg tgcccgccct gttttccgtt gggctcatgg acaccatcgy ncctccctcg    840
acggtcttcg ccgcttacaa ccactacgcc ggtccaaagg agatcagaat ctatccgtac    900
aacaaccacg aaggtggagg ttcttttccag gcaattgagc aggtgaaatt cttgaagaga    960
ctatttgagg aaggctag                                                  978

<210> SEQ ID NO 2
<211> LENGTH: 978
<212> TYPE: DNA
<213> ORGANISM: Thermotoga neapolitana
<220> FEATURE:
<221> NAME/KEY: misc_feature
<222> LOCATION: (831)..(831)
<223> OTHER INFORMATION: n is a, g, c, or t.

<400> SEQUENCE: 2
atggccttct tcgatatgcc ccttgaggaa ctgaaaaagt accggcctga aaggtacgag     60
gagaaagatt tcgatgagtt ctggagggaa acacttaaag aaagcgaagg attccctctg    120
gatcccgtct ttgaaaaggt ggactttcat ctcaaaacgg ttgaaacgta cgatgttact    180
ttctctggat acagggggca gagaataaag ggctggcttc ttgttccgaa gttggcggaa    240
gaaaagcttc catgcgtcgt gcagtacata ggttacaatg gtggaagggg ttttccacac    300
gactggctgt tctggccgtc aatgggttac atctgttttg tcatggacac caggggggcag    360 ggaagcggct ggatgaaggg agacacaccg gattaccctg aggtccagt cgatccacag    420 taccccggat tcatgacgag gggcattctg gatccgggaa cctattacta caggcgagtc    480
ttcgtggatg cggtcagggc ggtggaagca gccatttcct tcccgagagt ggattccagg    540
aaggtggtgg tggccggagg cagtcagggt gggggaatcg cccttgcggt gagtgccctg    600
tcgaacaggg tgaaggctct gctctgcgat gtgccgtttc tgtgccactt cagaagggcc    660
gtgcaacttg tcgacacaca cccatacgtg gagatcacca acttcctcaa aacccacagg    720
gacaaagagg agattgtttt cagaacactt tcctacttcg atggtgtgaa ctttgcagca    780
agggcaaagg tgcccgccct gttttccgtt gggctcatgg acaccatctc ncctccctcg    840
acggtcttcg ccgcttacaa ccactacgcc ggtccaaagg agatcagaat ctatccgtac    900
aacaaccacg aaggtggagg ttcttttccag gcaattgagc aggtgaaatt cttgaagaga    960
ctatttgagg aaggctag                                                  978

<210> SEQ ID NO 3
<211> LENGTH: 978
<212> TYPE: DNA
<213> ORGANISM: Thermotoga neapolitana

<400> SEQUENCE: 3
```

```
atggccttct cgatatgcc ccttgaggaa ctgaaaaagt accggcctga aaggtacgag      60
gagaaagatt tcgatgagtt ctggagggaa acacttaaag aaagcgaagg attccctctg    120
gatcccgtct ttgaaaaggt ggactttcat ctcaaaacgg ttgaaacgta cgatgttact    180
ttctctggat acagggggca gagaataaag ggctggcttc ttgttccgaa gttggcggaa    240
gaaaagcttc catgcgtcgt gcagtacata ggttacaatg gtggaagggg ttttccacac    300
gactggctgt tctggccgtc aatgggttac atctgttttg tcatggacac caggggcag    360 ggaagcggct ggatgaaggg agacacaccg gattaccctg aggtccagt cgatccacag    420 taccccggat tcatgacgag gggcattctg gatccgggaa cctattacta caggcgagtc    480
ttcgtggatg cggtcagggc ggtggaagca gccatttcct tcccgagagt ggattccagg    540
aaggtggtgg tggccggagg cagtcagggt gggggaatcg cccttgcggt gagtgccctg    600
tcgaacaggg tgaaggctct gctctgcgat gtgccgtttc tgtgccactt cagaagggcc    660
gtgcaacttg tcgacacaca cccatacgtg gagatcacca cttcctcaa aacccacagg    720 gacaaagagg agattgtttt cagaacactt tcctacttcg atggtgtgaa ctttgcagca    780
agggcaaagg tgcccgccct gttttccgtt gggctcatgg acaccatcag ycctccctcg    840
acggtcttcg ccgcttacaa ccactacgcc ggtccaaagg agatcagaat ctatccgtac    900
aacaaccacg aaggtggagg ttctttccag gcaattgagc aggtgaaatt cttgaagaga    960
ctatttgagg aaggctag                                                 978
```

<210> SEQ ID NO 4  
<211> LENGTH: 978  
<212> TYPE: DNA  
<213> ORGANISM: Thermotoga neapolitana  
<220> FEATURE:  
<221> NAME/KEY: misc_feature  
<222> LOCATION: (831)..(831)  
<223> OTHER INFORMATION: n is a, g, c, or t.

<400> SEQUENCE: 4

```
atggccttct cgatatgcc ccttgaggaa ctgaaaaagt accggcctga aaggtacgag      60
gagaaagatt tcgatgagtt ctggagggaa acacttaaag aaagcgaagg attccctctg    120
gatcccgtct ttgaaaaggt ggactttcat ctcaaaacgg ttgaaacgta cgatgttact    180
ttctctggat acagggggca gagaataaag ggctggcttc ttgttccgaa gttggcggaa    240
gaaaagcttc catgcgtcgt gcagtacata ggttacaatg gtggaagggg ttttccacac    300
gactggctgt tctggccgtc aatgggttac atctgttttg tcatggacac caggggcag    360 ggaagcggct ggatgaaggg agacacaccg gattaccctg aggtccagt cgatccacag    420 taccccggat tcatgacgag gggcattctg gatccgggaa cctattacta caggcgagtc    480
ttcgtggatg cggtcagggc ggtggaagca gccatttcct tcccgagagt ggattccagg    540
aaggtggtgg tggccggagg cagtcagggt gggggaatcg cccttgcggt gagtgccctg    600
tcgaacaggg tgaaggctct gctctgcgat gtgccgtttc tgtgccactt cagaagggcc    660
gtgcaacttg tcgacacaca cccatacgtg gagatcacca cttcctcaa aacccacagg    720 gacaaagagg agattgtttt cagaacactt tcctacttcg atggtgtgaa ctttgcagca    780
agggcaaagg tgcccgccct gttttccgtt gggctcatgg acaccatcac ncctccctcg    840
acggtcttcg ccgcttacaa ccactacgcc ggtccaaagg agatcagaat ctatccgtac    900
aacaaccacg aaggtggagg ttctttccag gcaattgagc aggtgaaatt cttgaagaga    960
ctatttgagg aaggctag                                                 978
```

```
<210> SEQ ID NO 5
<211> LENGTH: 325
<212> TYPE: PRT
<213> ORGANISM: Thermotoga neapolitana
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 5

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Ser Gln Gly Gly Gly
            180                 185                 190

Ile Ala Leu Ala Val Ser Ala Leu Ser Asn Arg Val Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Xaa Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
                325

<210> SEQ ID NO 6
<211> LENGTH: 978
<212> TYPE: DNA
```

<213> ORGANISM: Thermotoga maritima
<220> FEATURE:
<221> NAME/KEY: misc_feature
<222> LOCATION: (831)..(831)
<223> OTHER INFORMATION: n is a, g, c, or t.

<400> SEQUENCE: 6

```
atggccttct tcgatttacc actcgaagaa ctgaagaaat atcgtccaga gcggtacgaa    60
gagaaagact tcgatgagtt ctgggaagag acactcgcag agagcgaaaa gttcccctta   120
gaccccgtct tcgagaggat ggagtctcac ctcaaaacag tcgaagcgta cgatgtcacc   180
ttctccggat acaggggaca gaggatcaaa gggtggctcc ttgttccaaa actggaagaa   240
gaaaaacttc cctgcgttgt gcagtacata ggatacaacg gtggaagagg attccctcac   300
gactggctgt tctggccttc tatgggttac atatgtttcg tcatggatac tcgaggtcag   360
ggaagcggct ggctgaaagg agacacaccg gattaccctg agggtcccgt tgaccctcag   420
tatccaggat tcatgacaag aggaatactg gatcccagaa cttactacta cagacgagtc   480
ttcacggacg ctgtcagagc cgttgaagct gctgcttctt ttcctcaggt agatcaagaa   540
agaatcgtga tagctggagg cagtcagggt ggcggaatag cccttgcggt gagcgctctc   600
tcaaagaaag caaaggctct tctgtgcgat gtgccgtttc tgtgtcactt cagaagagca   660
gtacagcttg tggatacgca tccatacgcg gagatcacga actttctaaa gacccacaga   720
gacaaggaag aaatcgtgtt caggactctt tcctatttcg atggagtgaa cttcgcagcc   780
agagcgaaga tccctgcgct gttttctgtg ggtctcatgg acaacattgy ncctccttca   840
acggttttcg ctgcctacaa ttactacgct ggaccgaagg aaatcagaat ctatccgtac   900
aacaaccacg agggaggagg ctcttttccaa gcggttgaac aggtgaaatt cttgaaaaaa   960
ctatttgaga aaggctaa                                                  978
```

<210> SEQ ID NO 7
<211> LENGTH: 978
<212> TYPE: DNA
<213> ORGANISM: Thermotoga maritima
<220> FEATURE:
<221> NAME/KEY: misc_feature
<222> LOCATION: (831)..(831)
<223> OTHER INFORMATION: n is a, g, c, or t.

<400> SEQUENCE: 7

```
atggccttct tcgatttacc actcgaagaa ctgaagaaat atcgtccaga gcggtacgaa    60
gagaaagact tcgatgagtt ctgggaagag acactcgcag agagcgaaaa gttcccctta   120
gaccccgtct tcgagaggat ggagtctcac ctcaaaacag tcgaagcgta cgatgtcacc   180
ttctccggat acaggggaca gaggatcaaa gggtggctcc ttgttccaaa actggaagaa   240
gaaaaacttc cctgcgttgt gcagtacata ggatacaacg gtggaagagg attccctcac   300
gactggctgt tctggccttc tatgggttac atatgtttcg tcatggatac tcgaggtcag   360
ggaagcggct ggctgaaagg agacacaccg gattaccctg agggtcccgt tgaccctcag   420
tatccaggat tcatgacaag aggaatactg gatcccagaa cttactacta cagacgagtc   480
ttcacggacg ctgtcagagc cgttgaagct gctgcttctt ttcctcaggt agatcaagaa   540
agaatcgtga tagctggagg cagtcagggt ggcggaatag cccttgcggt gagcgctctc   600
tcaaagaaag caaaggctct tctgtgcgat gtgccgtttc tgtgtcactt cagaagagca   660
gtacagcttg tggatacgca tccatacgcg gagatcacga actttctaaa gacccacaga   720
gacaaggaag aaatcgtgtt caggactctt tcctatttcg atggagtgaa cttcgcagcc   780
```

| agagcgaaga tccctgcgct gttttctgtg ggtctcatgg acaacatttc ncctccttca | 840 |
| acggttttcg ctgcctacaa ttactacgct ggaccgaagg aaatcagaat ctatccgtac | 900 |
| aacaaccacg agggaggagg ctctttccaa gcggttgaac aggtgaaatt cttgaaaaaa | 960 |
| ctatttgaga aaggctaa | 978 |

<210> SEQ ID NO 8
<211> LENGTH: 978
<212> TYPE: DNA
<213> ORGANISM: Thermotoga maritima

<400> SEQUENCE: 8

| atggccttct tcgatttacc actcgaagaa ctgaagaaat atcgtccaga gcggtacgaa | 60 |
| gagaaagact tcgatgagtt ctgggaagag acactcgcag agagcgaaaa gttcccctta | 120 |
| gaccccgtct tcgagaggat ggagtctcac ctcaaaacag tcgaagcgta cgatgtcacc | 180 |
| ttctccggat acaggggaca gaggatcaaa ggtggctcc ttgttccaaa actggaagaa | 240 |
| gaaaaacttc cctgcgttgt gcagtacata ggatacaacg gtggaagagg attccctcac | 300 |
| gactggctgt tctggccttc tatgggttac atatgtttcg tcatggatac tcgaggtcag | 360 |
| ggaagcggct ggctgaaagg agacacaccg gattaccctg agggtcccgt tgaccctcag | 420 |
| tatccaggat tcatgacaag aggaatactg gatcccagaa cttactacta cagacgagtc | 480 |
| ttcacggacg ctgtcagagc cgttgaagct gctgcttctt ttcctcaggt agatcaagaa | 540 |
| agaatcgtga tagctggagg cagtcagggt ggcggaatag cccttgcggt gagcgctctc | 600 |
| tcaaagaaag caaaggctct tctgtgcgat gtgccgtttc tgtgtcactt cagaagagca | 660 |
| gtacagcttg tggatacgca tccatacgcg gagatcacga actttctaaa gacccacaga | 720 |
| gacaaggaag aaatcgtgtt caggactctt tcctatttcg atggagtgaa cttcgcagcc | 780 |
| agagcgaaga tccctgcgct gttttctgtg ggtctcatgg acaacattag ycctccttca | 840 |
| acggttttcg ctgcctacaa ttactacgct ggaccgaagg aaatcagaat ctatccgtac | 900 |
| aacaaccacg agggaggagg ctctttccaa gcggttgaac aggtgaaatt cttgaaaaaa | 960 |
| ctatttgaga aaggctaa | 978 |

<210> SEQ ID NO 9
<211> LENGTH: 978
<212> TYPE: DNA
<213> ORGANISM: Thermotoga maritima
<220> FEATURE:
<221> NAME/KEY: misc_feature
<222> LOCATION: (831)..(831)
<223> OTHER INFORMATION: n is a, g, c, or t.

<400> SEQUENCE: 9

| atggccttct tcgatttacc actcgaagaa ctgaagaaat atcgtccaga gcggtacgaa | 60 |
| gagaaagact tcgatgagtt ctgggaagag acactcgcag agagcgaaaa gttcccctta | 120 |
| gaccccgtct tcgagaggat ggagtctcac ctcaaaacag tcgaagcgta cgatgtcacc | 180 |
| ttctccggat acaggggaca gaggatcaaa ggtggctcc ttgttccaaa actggaagaa | 240 |
| gaaaaacttc cctgcgttgt gcagtacata ggatacaacg gtggaagagg attccctcac | 300 |
| gactggctgt tctggccttc tatgggttac atatgtttcg tcatggatac tcgaggtcag | 360 |
| ggaagcggct ggctgaaagg agacacaccg gattaccctg agggtcccgt tgaccctcag | 420 |
| tatccaggat tcatgacaag aggaatactg gatcccagaa cttactacta cagacgagtc | 480 |
| ttcacggacg ctgtcagagc cgttgaagct gctgcttctt ttcctcaggt agatcaagaa | 540 |

-continued

```
agaatcgtga tagctggagg cagtcagggt ggcggaatag cccttgcggt gagcgctctc    600
tcaaagaaag caaaggctct tctgtgcgat gtgccgtttc tgtgtcactt cagaagagca    660
gtacagcttg tggatacgca tccatacgcg gagatcacga actttctaaa gacccacaga    720
gacaaggaag aaatcgtgtt caggactctt tcctatttcg atggagtgaa cttcgcagcc    780
agagcgaaga tccctgcgct gttttctgtg gtctcatgg acaacattac ncctccttca     840
acggttttcg ctgcctacaa ttactacgct ggaccgaagg aaatcagaat ctatccgtac    900
aacaaccacg agggaggagg ctctttccaa gcggttgaac aggtgaaatt cttgaaaaaa    960
ctatttgaga aaggctaa                                                  978
```

<210> SEQ ID NO 10
<211> LENGTH: 325
<212> TYPE: PRT
<213> ORGANISM: Thermotoga maritima
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 10

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn Tyr
```

```
                275                 280                 285
Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 11
<211> LENGTH: 981
<212> TYPE: DNA
<213> ORGANISM: Thermotoga lettingae
<220> FEATURE:
<221> NAME/KEY: misc_feature
<222> LOCATION: (831)..(831)
<223> OTHER INFORMATION: n is a, g, c, or t.

<400> SEQUENCE: 11
atggtctatt ttgatatgcc attggaagat ttgagaaaat atctgccaca gaggtacgaa      60
gaaaaggatt tcgatgattt ctggaaacaa acaatccatg aaacaagggg atattttcaa     120
gaaccaattc tcaaaaaagt ggattttttat ttgcagaatt ttgagacttt tgatgtgact    180
ttctctggtt acagaggtca gaagataaaa ggatggttga ttttgccaaa attcagaaat    240
gggaaattac cctgcgtagt tgaatttgtt ggttatggag gaggaagagg atttccatat    300
gactggctgc tttggagtgc ggcaggatac gcacatttca taatggacac gagaggacaa    360
ggtagcaact ggatgaaggg tgatacacca gattatgaag ataatccttc agatccacaa    420
tatccaggct ttctgacaaa aggagtactg aacccggaaa cttattatta caggagagtt    480
tttatggatg catttatggc tgttgaaact atcagccaac ttgaacaaat agattcacaa    540
accataatat tatcaggtgc aagccagggt ggtggaatag ctttggctgt gagtgcattg    600
tcttcaaagg tcatggctct actttgtgat gttccctttc tgtgtcatta caaaagagca    660
gttcagataa cagattcaat gccctatgca gaaattacga gatattgcaa aactcacatt    720
gacaaaatcc aaacagtatt cagaacccctc tcttattttg acggcgtcaa ttttgcagct    780
cgtgcaaaat gccctgcttt gttttcggtg ggactcatgg acgacattgy nccaccttca    840
acagttttgg ccgcttacaa ttattacgct ggtgagaaag atattagaat ttacccatac    900
aacaaccatg aaggcggtgg ttccttccat acactggaaa aattgaaatt tgtgaaaaaa    960
acaatttcta tgagagagtg a                                               981

<210> SEQ ID NO 12
<211> LENGTH: 981
<212> TYPE: DNA
<213> ORGANISM: Thermotoga lettingae
<220> FEATURE:
<221> NAME/KEY: misc_feature
<222> LOCATION: (831)..(831)
<223> OTHER INFORMATION: n is a, g, c, or t.

<400> SEQUENCE: 12
atggtctatt ttgatatgcc attggaagat ttgagaaaat atctgccaca gaggtacgaa      60
gaaaaggatt tcgatgattt ctggaaacaa acaatccatg aaacaagggg atattttcaa     120
gaaccaattc tcaaaaaagt ggattttttat ttgcagaatt ttgagacttt tgatgtgact    180
ttctctggtt acagaggtca gaagataaaa ggatggttga ttttgccaaa attcagaaat    240
gggaaattac cctgcgtagt tgaatttgtt ggttatggag gaggaagagg atttccatat    300
gactggctgc tttggagtgc ggcaggatac gcacatttca taatggacac gagaggacaa    360
```

```
ggtagcaact ggatgaaggg tgatacacca gattatgaag ataatccttc agatccacaa    420
tatccaggct ttctgacaaa aggagtactg aacccggaaa cttattatta caggagagtt    480
tttatggatg catttatggc tgttgaaact atcagccaac ttgaacaaat agattcacaa    540
accataatat tatcaggtgc aagccagggt ggtggaatag ctttggctgt gagtgcattg    600
tcttcaaagg tcatggctct actttgtgat gttcccttc tgtgtcatta caaaagagca     660
gttcagataa cagattcaat gccctatgca gaaattacga gatattgcaa aactcacatt    720
gacaaaatcc aaacagtatt cagaaccctc tcttattttg acggcgtcaa ttttgcagct    780
cgtgcaaaat gccctgcttt gttttcggtg ggactcatgg acgacatttc nccaccttca    840 acagttttg ccgcttacaa ttattacgct ggtgagaaag atattagaat ttacccatac      900
aacaaccatg aaggcggtgg ttccttccat acactggaaa aattgaaatt tgtgaaaaaa    960
acaatttcta tgagagagtg a                                               981
```

<210> SEQ ID NO 13
<211> LENGTH: 981
<212> TYPE: DNA
<213> ORGANISM: Thermotoga lettingae

<400> SEQUENCE: 13

```
atggtctatt ttgatatgcc attggaagat ttgagaaaat atctgccaca gaggtacgaa     60
gaaaaggatt tcgatgattt ctggaaacaa acaatccatg aaacaagggg atattttcaa    120
gaaccaattc tcaaaaaagt ggattttat ttgcagaatg ttgagacttt tgatgtgact     180
ttctctggtt acagaggtca aagataaaa ggatggttga ttttgccaaa attcagaaat      240
gggaaattac cctgcgtagt tgaatttgtt ggttatggag gaggaagagg atttccatat    300
gactggctgc tttggagtgc ggcaggatac gcacatttca taatggacac gagaggacaa    360
ggtagcaact ggatgaaggg tgatacacca gattatgaag ataatccttc agatccacaa    420
tatccaggct ttctgacaaa aggagtactg aacccggaaa cttattatta caggagagtt    480
tttatggatg catttatggc tgttgaaact atcagccaac ttgaacaaat agattcacaa    540
accataatat tatcaggtgc aagccagggt ggtggaatag ctttggctgt gagtgcattg    600
tcttcaaagg tcatggctct actttgtgat gttcccttc tgtgtcatta caaaagagca     660
gttcagataa cagattcaat gccctatgca gaaattacga gatattgcaa aactcacatt    720
gacaaaatcc aaacagtatt cagaaccctc tcttattttg acggcgtcaa ttttgcagct    780
cgtgcaaaat gccctgcttt gttttcggtg ggactcatgg acgacattag yccaccttca    840 acagttttg ccgcttacaa ttattacgct ggtgagaaag atattagaat ttacccatac      900
aacaaccatg aaggcggtgg ttccttccat acactggaaa aattgaaatt tgtgaaaaaa    960
acaatttcta tgagagagtg a                                               981
```

<210> SEQ ID NO 14
<211> LENGTH: 981
<212> TYPE: DNA
<213> ORGANISM: Thermotoga lettingae
<220> FEATURE:
<221> NAME/KEY: misc_feature
<222> LOCATION: (831)..(831)
<223> OTHER INFORMATION: n is a, g, c, or t.

<400> SEQUENCE: 14

```
atggtctatt ttgatatgcc attggaagat ttgagaaaat atctgccaca gaggtacgaa     60
gaaaaggatt tcgatgattt ctggaaacaa acaatccatg aaacaagggg atattttcaa    120
```

```
gaaccaattc tcaaaaaagt ggatttttat ttgcagaatg ttgagacttt tgatgtgact      180
ttctctggtt acagaggtca gaagataaaa ggatggttga ttttgccaaa attcagaaat      240
gggaaattac cctgcgtagt tgaatttgtt ggttatggag gaggaagagg atttccatat      300
gactggctgc tttggagtgc ggcaggatac gcacatttca taatggacac gagaggacaa      360
ggtagcaact ggatgaaggg tgatacacca gattatgaag ataatccttc agatccacaa      420
tatccaggct ttctgacaaa aggagtactg aacccggaaa cttattatta caggagagtt      480
tttatggatg catttatggc tgttgaaact atcagccaac ttgaacaaat agattcacaa      540
accataatat tatcaggtgc aagccagggt ggtggaatag cctttggctgt gagtgcattg     600 tcttcaaagg tcatggctct actttgtgat gttcccttc tgtgtcatta caaaagagca      660
gttcagataa cagattcaat gccctatgca gaaattacga gatattgcaa aactcacatt      720
gacaaaatcc aaacagtatt cagaacccct cttattttg acggcgtcaa ttttgcagct       780
cgtgcaaaat gccctgcttt gttttcggtg ggactcatgg acgacattac nccaccttca     840 acagttttg ccgcttacaa ttattacgct ggtgagaaag atattagaat ttacccatac       900
aacaaccatg aaggcggtgg ttccttccat acactggaaa aattgaaatt tgtgaaaaaa     960
acaatttcta tgagagagtg a                                              981
```

<210> SEQ ID NO 15
<211> LENGTH: 326
<212> TYPE: PRT
<213> ORGANISM: Thermotoga lettingae
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 15

```
Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Gly Arg
                85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
```

```
                        195                 200                 205
Cys Asp Val Pro Phe Leu Cys His Tyr Lys Arg Ala Val Gln Ile Thr
        210                 215                 220
Asp Ser Met Pro Tyr Ala Glu Ile Thr Arg Tyr Cys Lys Thr His Ile
225                 230                 235                 240
Asp Lys Ile Gln Thr Val Phe Arg Thr Leu Ser Tyr Phe Asp Gly Val
                245                 250                 255
Asn Phe Ala Ala Arg Ala Lys Cys Pro Ala Leu Phe Ser Val Gly Leu
            260                 265                 270
Met Asp Asp Ile Xaa Pro Pro Ser Thr Val Phe Ala Ala Tyr Asn Tyr
        275                 280                 285
Tyr Ala Gly Glu Lys Asp Ile Arg Ile Tyr Pro Tyr Asn Asn His Glu
    290                 295                 300
Gly Gly Gly Ser Phe His Thr Leu Glu Lys Leu Lys Phe Val Lys Lys
305                 310                 315                 320
Thr Ile Ser Met Arg Glu
                325

<210> SEQ ID NO 16
<211> LENGTH: 978
<212> TYPE: DNA
<213> ORGANISM: Thermotoga petrophilia
<220> FEATURE:
<221> NAME/KEY: misc_feature
<222> LOCATION: (831)..(831)
<223> OTHER INFORMATION: n is a, g, c, or t.

<400> SEQUENCE: 16
atggcattct tcgacctgcc gctggaggaa ctgaaaaagt atcgcccgga gcgttacgaa      60
gaaaaggatt tcgatgagtt ctgggaaggc accctggccg agaacgaaaa attccctctg     120
gatccggtct tcaacgtat ggaaagccat ctgaaaaccg tagaggctta cgacgtgacc      180
ttcagcggtt acatgggcca gcgtatcaaa ggctggctgc tggtcccgaa actggaggag     240
gagaaactgc cgtgcgttgt tcagtacatc ggctacaacg gcggtcgcgg tttcccgcac     300
gattggctgt tctggccgtc tatgggttac atctgctttg ttatggacac ccgtggccag     360
ggtagcggtt ggatgaaggg tgacaccccg gactatccgg aggacccggt agacccgcag     420
tacccaggct ttatgacccg cggcattctg acccgcgca cttactacta ccgtcgcgtt      480
tttaccgatg ctgttcgcgc agtggaggca gccgcgtcct ttccacgcgt agaccacgaa     540
cgtatcgtaa tcgcaggcgg ctcccagggt ggcggcatcg cgctggcggt ttccgcactg     600
agcaaaaagg ccaaagcgct gctgtgcgat gtgccgttcc tgtgtcactt ccgtcgtgcg     660
gttcagctgg tagataccca cccgtacgct gagatcacca ctttctgaa gacgcatcgt      720
gataaagagg aaatcgtatt tcgtacgctg tcctatttcg atggtgtgaa ctttgcggta     780
cgtgcaaaga tcccggccct gttctctgtt ggtctgatgg acaacattgy nccgccgagc     840
actgtctttg cagcgtacaa ccactatgcg ggcccaaaag aaattcgcat ctacccatac     900
aacaaccacg aaggcggcgg ttccttccag gcaatcgaac aggtcaaatt cctgaaacgt     960
ctgttcgaga aaggttaa                                                  978

<210> SEQ ID NO 17
<211> LENGTH: 978
<212> TYPE: DNA
<213> ORGANISM: Thermotoga petrophilia
<220> FEATURE:
<221> NAME/KEY: misc_feature
<222> LOCATION: (831)..(831)
```

<223> OTHER INFORMATION: n is a, g, c, or t.

<400> SEQUENCE: 17

```
atggcattct tcgacctgcc gctggaggaa ctgaaaaagt atcgcccgga gcgttacgaa      60
gaaaaggatt tcgatgagtt ctgggaaggc accctggccg agaacgaaaa attccctctg     120
gatccggtct tcgaacgtat ggaaagccat ctgaaaaccg tagaggctta cgacgtgacc     180
ttcagcggtt acatgggcca gcgtatcaaa ggctggctgc tggtcccgaa actggaggag     240
gagaaactgc cgtgcgttgt tcagtacatc ggctacaacg gcggtcgcgg tttcccgcac     300
gattggctgt tctggccgtc tatgggttac atctgctttg ttatggacac ccgtggccag     360
ggtagcggtt ggatgaaggg tgacaccccg gactatccgg aggacccggt agacccgcag     420
tacccaggct ttatgacccg cggcattctg gacccgcgca cttactacta ccgtcgcgtt     480
tttaccgatg ctgttcgcgc agtggaggca gccgcgtcct ttccacgcgt agaccacgaa     540
cgtatcgtaa tcgcaggcgg ctcccagggt ggcggcatcg cgctggcggt ttccgcactg     600
agcaaaaagg ccaaagcgct gctgtgcgat gtgccgttcc tgtgtcactt ccgtcgtgcg     660
gttcagctgg tagatacccca cccgtacgct gagatcacca actttctgaa gacgcatcgt     720
gataaagagg aaatcgtatt tcgtacgctg tcctatttcg atggtgtgaa ctttgcggta     780
cgtgcaaaga tccggccct gttctctgtt ggtctgatgg acaacatttc nccgccgagc     840
actgtctttg cagcgtacaa ccactatgcg ggcccaaaag aaattcgcat ctacccatac     900
aacaaccacg aaggcggcgg ttccttccag gcaatcgaac aggtcaaatt cctgaaacgt     960
ctgttcgaga aaggttaa                                                   978
```

<210> SEQ ID NO 18
<211> LENGTH: 978
<212> TYPE: DNA
<213> ORGANISM: Thermotoga petrophilia

<400> SEQUENCE: 18

```
atggcattct tcgacctgcc gctggaggaa ctgaaaaagt atcgcccgga gcgttacgaa      60
gaaaaggatt tcgatgagtt ctgggaaggc accctggccg agaacgaaaa attccctctg     120
gatccggtct tcgaacgtat ggaaagccat ctgaaaaccg tagaggctta cgacgtgacc     180
ttcagcggtt acatgggcca gcgtatcaaa ggctggctgc tggtcccgaa actggaggag     240
gagaaactgc cgtgcgttgt tcagtacatc ggctacaacg gcggtcgcgg tttcccgcac     300
gattggctgt tctggccgtc tatgggttac atctgctttg ttatggacac ccgtggccag     360
ggtagcggtt ggatgaaggg tgacaccccg gactatccgg aggacccggt agacccgcag     420
tacccaggct ttatgacccg cggcattctg gacccgcgca cttactacta ccgtcgcgtt     480
tttaccgatg ctgttcgcgc agtggaggca gccgcgtcct ttccacgcgt agaccacgaa     540
cgtatcgtaa tcgcaggcgg ctcccagggt ggcggcatcg cgctggcggt ttccgcactg     600
agcaaaaagg ccaaagcgct gctgtgcgat gtgccgttcc tgtgtcactt ccgtcgtgcg     660
gttcagctgg tagatacccca cccgtacgct gagatcacca actttctgaa gacgcatcgt     720
gataaagagg aaatcgtatt tcgtacgctg tcctatttcg atggtgtgaa ctttgcggta     780
cgtgcaaaga tccggccct gttctctgtt ggtctgatgg acaacattag yccgccgagc     840
actgtctttg cagcgtacaa ccactatgcg ggcccaaaag aaattcgcat ctacccatac     900
aacaaccacg aaggcggcgg ttccttccag gcaatcgaac aggtcaaatt cctgaaacgt     960
ctgttcgaga aaggttaa                                                   978
```

<210> SEQ ID NO 19
<211> LENGTH: 978
<212> TYPE: DNA
<213> ORGANISM: Thermotoga petrophilia
<220> FEATURE:
<221> NAME/KEY: misc_feature
<222> LOCATION: (831)..(831)
<223> OTHER INFORMATION: n is a, g, c, or t.

<400> SEQUENCE: 19

```
atggcattct tcgacctgcc gctggaggaa ctgaaaaagt atcgcccgga gcgttacgaa      60
gaaaaggatt tcgatgagtt ctgggaaggc accctggccg agaacgaaaa attccctctg     120
gatccggtct tcgaacgtat ggaaagccat ctgaaaaccg tagaggctta cgacgtgacc     180
ttcagcggtt acatgggcca gcgtatcaaa ggctggctgc tggtcccgaa actggaggag     240
gagaaactgc cgtgcgttgt tcagtacatc ggctacaacg gcggtcgcgg tttcccgcac     300
gattggctgt tctggccgtc tatgggttac atctgctttg ttatggacac ccgtggccag     360
ggtagcggtt ggatgaaggg tgacaccccg gactatccgg aggacccggt agaccccgcag   420
tacccaggct ttatgacccg cggcattctg acccgcgcca cttactacta ccgtcgcgtt     480
tttaccgatg ctgttcgcgc agtggaggca gccgcgtcct ttccacgcgt agaccacgaa     540
cgtatcgtaa tcgcaggcgg ctcccagggt ggcggcatcg cgctggcggt tccgcactg     600
agcaaaaagg ccaaagcgct gctgtgcgat gtgccgttcc tgtgtcactt ccgtcgtgcg     660
gttcagctgg tagatacccca cccgtacgct gagatcacca actttctgaa gacgcatcgt     720
gataaagagg aaatcgtatt tcgtacgctg tcctatttcg atggtgtgaa cttgcggta     780
cgtgcaaaga tcccggccct gttctctgtt ggtctgatgg acaacattac nccgccgagc     840
actgtctttg cagcgtacaa ccactatgcg ggcccaaaag aaattcgcat ctacccatac     900
aacaaccacg aaggcggcgg ttccttccag gcaatcgaac aggtcaaatt cctgaaacgt     960
ctgttcgaga aaggttaa                                                    978
```

<210> SEQ ID NO 20
<211> LENGTH: 325
<212> TYPE: PRT
<213> ORGANISM: Thermotoga petrophilia
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 20

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
```

```
            115                 120                 125
Thr Pro Asp Tyr Pro Glu Asp Pro Val Asp Pro Gln Tyr Pro Gly Phe
        130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
                180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
        210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
        290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 21
<211> LENGTH: 978
<212> TYPE: DNA
<213> ORGANISM: Thermotoga sp. RQ2a
<220> FEATURE:
<221> NAME/KEY: misc_feature
<222> LOCATION: (831)..(831)
<223> OTHER INFORMATION: n is a, g, c, or t.

<400> SEQUENCE: 21
atggcctttt tcgatttacc actcgaagaa ctgaagaaat accgtccgga gcggtacgaa    60
gagaaagact tcgatgagtt ctggaaagaa cactcgcag agagcgaaaa gtttcccctg    120
gaccccgtct tcgagaggat ggagtctcac ctcaaaacgg tcgaagtgta cgatgtcacc    180
ttctccggat acagaggaca gaggatcaag gggtggctcc ttgttccaaa attggaagaa    240
gaaaaacttc cctgcgttgt gcagtacata ggatacaacg tggaagagg attccctcac     300 gactggctgt tctggccttc tatgggttac atatgtttcg tcatggatac tcgaggacag    360
ggaagcggct ggctgaaagg agatacaccg gattaccctg aggatcccgt tgaccctcag    420
tatccaggat tcatgacaag aggaatactg gatcccagaa cttactacta cagacgagtc    480
ttcacggacg ctgtcagagc cgttgaagcc gctgcttctt tccctcgggt agatcacgaa    540
agaatcgtga tagctggagg cagtcagggt ggcggaatag cccttgcggt gagcgctctc    600
tcaaagaaag caaaggctct tctgtgcgat gtgccgtttc tgtgtcactt cagaagggca    660
gtgcagcttg tggatacgca tccatacgcg gagatcacga actttctaaa gactcacagg    720
gacaaggaag aaatcgtgtt caggactctt tcctatttcg atggagtgaa cttcgcagtc    780
agagcgaaga tccctgcgct gttttctgtg gtctcatgg acaacattgy ncctccttca    840
```

```
acgttttg  ctgcctacaa  tcactacgct  gggccgaagg  aaatcagaat  ctatccgtac    900
aacaaccacg  agggaggagg  ctctttccag  gcaattgaac  aggtgaaatt  cttgaagaga    960
ctatttgaga  aaggctag                                                     978
```

<210> SEQ ID NO 22
<211> LENGTH: 978
<212> TYPE: DNA
<213> ORGANISM: Thermotoga sp. RQ2a
<220> FEATURE:
<221> NAME/KEY: misc_feature
<222> LOCATION: (831)..(831)
<223> OTHER INFORMATION: n is a, g, c, or t.

<400> SEQUENCE: 22

```
atggccttt  tcgatttacc  actcgaagaa  ctgaagaaat  accgtccgga  gcggtacgaa     60
gagaaagact  tcgatgagtt  ctggaaagaa  acactcgcag  agagcgaaaa  gtttcccctg    120
gaccccgtct  tcgagaggat  ggagtctcac  ctcaaaacgg  tcgaagtgta  cgatgtcacc    180
ttctccggat  acagaggaca  gaggatcaag  gggtggctcc  ttgttccaaa  attggaagaa    240
gaaaaacttc  cctgcgttgt  gcagtacata  ggatacaacg  gtggaagagg  attccctcac    300
gactggctgt  tctggccttc  tatgggttac  atatgtttcg  tcatggatac  tcgaggacag    360
ggaagcggct  ggctgaaagg  agatacaccg  gattaccctg  aggatcccgt  tgaccctcag    420
tatccaggat  tcatgacaag  aggaatactg  gatcccagaa  cttactacta  cagacgagtc    480
ttcacggacg  ctgtcagagc  cgttgaagcc  gctgcttctt  ttcctcgggt  agatcacgaa    540
agaatcgtga  tagctggagg  cagtcagggt  ggcggaatag  cccttgcggt  gagcgctctc    600
tcaaagaaag  caaggctct  tctgtgcgat  gtgccgtttc  tgtgtcactt  cagaagggca    660
gtgcagcttg  tggatacgca  tccatacgcg  gagatcacga  actttctaaa  gactcacagg    720
gacaaggaag  aaatcgtgtt  caggactctt  tcctatttcg  atggagtgaa  cttcgcagtc    780
agagcgaaga  tccctgcgct  gttttctgtg  ggtctcatgg  acaacatttc  ncctccttca    840 acgttttg  ctgcctacaa  tcactacgct  gggccgaagg  aaatcagaat  ctatccgtac     900
aacaaccacg  agggaggagg  ctctttccag  gcaattgaac  aggtgaaatt  cttgaagaga    960
ctatttgaga  aaggctag                                                     978
```

<210> SEQ ID NO 23
<211> LENGTH: 978
<212> TYPE: DNA
<213> ORGANISM: Thermotoga sp. RQ2a

<400> SEQUENCE: 23

```
atggccttt  tcgatttacc  actcgaagaa  ctgaagaaat  accgtccgga  gcggtacgaa     60
gagaaagact  tcgatgagtt  ctggaaagaa  acactcgcag  agagcgaaaa  gtttcccctg    120
gaccccgtct  tcgagaggat  ggagtctcac  ctcaaaacgg  tcgaagtgta  cgatgtcacc    180
ttctccggat  acagaggaca  gaggatcaag  gggtggctcc  ttgttccaaa  attggaagaa    240
gaaaaacttc  cctgcgttgt  gcagtacata  ggatacaacg  gtggaagagg  attccctcac    300
gactggctgt  tctggccttc  tatgggttac  atatgtttcg  tcatggatac  tcgaggacag    360
ggaagcggct  ggctgaaagg  agatacaccg  gattaccctg  aggatcccgt  tgaccctcag    420
tatccaggat  tcatgacaag  aggaatactg  gatcccagaa  cttactacta  cagacgagtc    480
ttcacggacg  ctgtcagagc  cgttgaagcc  gctgcttctt  ttcctcgggt  agatcacgaa    540
agaatcgtga  tagctggagg  cagtcagggt  ggcggaatag  cccttgcggt  gagcgctctc    600
```

```
tcaaagaaag caaaggctct tctgtgcgat gtgccgtttc tgtgtcactt cagaagggca     660
gtgcagcttg tggatacgca tccatacgcg gagatcacga actttctaaa gactcacagg     720
gacaaggaag aaatcgtgtt caggactctt tcctatttcg atggagtgaa cttcgcagtc     780
agagcgaaga tccctgcgct gttttctgtg gtctcatgg acaacattag ycctccttca     840 acggttttg ctgcctacaa tcactacgct gggccgaagg aaatcagaat ctatccgtac      900
aacaaccacg agggaggagg ctctttccag gcaattgaac aggtgaaatt cttgaagaga     960
ctatttgaga aaggctag                                                   978
```

<210> SEQ ID NO 24
<211> LENGTH: 978
<212> TYPE: DNA
<213> ORGANISM: Thermotoga sp. RQ2a
<220> FEATURE:
<221> NAME/KEY: misc_feature
<222> LOCATION: (831)..(831)
<223> OTHER INFORMATION: n is a, g, c, or t.

<400> SEQUENCE: 24

```
atggccttt tcgatttacc actcgaagaa ctgaagaaat accgtccgga gcggtacgaa       60
gagaaagact tcgatgagtt ctggaaagaa acactcgcag agagcgaaaa gtttccctg      120 gaccccgtct tcgagaggat ggagtctcac ctcaaaacgg tcgaagtgta cgatgtcacc    180
ttctccggat acagaggaca gaggatcaag gggtggctcc ttgttccaaa attggaagaa     240
gaaaaacttc cctgcgttgt gcagtacata ggatacaacg gtggaagagg attccctcac   300
gactggctgt tctggccttc tatgggttac atatgtttcg tcatggatac tcgaggacag    360
ggaagcggct ggctgaaagg agatacaccg gattaccctg aggatcccgt tgaccctcag   420
tatccaggat tcatgacaag aggaatactg gatcccagaa cttactacta cagacgagtc   480 ttcacgacg ctgtcagagc cgttgaagcc gctgcttctt tccctcgggt agatcacgaa    540
agaatcgtga tagctggagg cagtcagggt ggcggaatag cccttgcggt gagcgctctc    600
tcaaagaaag caaaggctct tctgtgcgat gtgccgtttc tgtgtcactt cagaagggca    660
gtgcagcttg tggatacgca tccatacgcg gagatcacga actttctaaa gactcacagg     720
gacaaggaag aaatcgtgtt caggactctt tcctatttcg atggagtgaa cttcgcagtc     780
agagcgaaga tccctgcgct gttttctgtg gtctcatgg acaacattac ncctccttca     840 acggttttg ctgcctacaa tcactacgct gggccgaagg aaatcagaat ctatccgtac      900
aacaaccacg agggaggagg ctctttccag gcaattgaac aggtgaaatt cttgaagaga     960
ctatttgaga aaggctag                                                   978
```

<210> SEQ ID NO 25
<211> LENGTH: 325
<212> TYPE: PRT
<213> ORGANISM: Thermotoga sp. RQ2a
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 25

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
```

```
                 35                  40                  45
Ser His Leu Lys Thr Val Glu Val Tyr Asp Val Thr Phe Ser Gly Tyr
 50                  55                  60

Arg Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Leu Lys Gly Asp
                115                 120                 125

Thr Pro Asp Tyr Pro Glu Asp Pro Val Asp Pro Gln Tyr Pro Gly Phe
130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly
                180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
                210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
                260                 265                 270

Met Asp Asn Ile Xaa Pro Pro Ser Thr Val Phe Ala Ala Tyr Asn His
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 26
<211> LENGTH: 990
<212> TYPE: DNA
<213> ORGANISM: Thermotoga sp. RQ2b
<220> FEATURE:
<221> NAME/KEY: misc_feature
<222> LOCATION: (834)..(834)
<223> OTHER INFORMATION: n is a, g, c, or t.

<400> SEQUENCE: 26
atggcgctat ttgatatgcc tctggaaaag ttaagatcat accttcccga tagatacgag      60
gaggaagatt tgatctgtt ctggaaagag actcttgagg agtcaagaaa attcccactg     120
gatcctattt tgaaagagt agattatctg ctggagaacg tggaagtata cgatgtcacc     180
ttctccggtt acaggggtca agaataaag gcgtggttga ttctaccggt tgttaagaag     240
gaagaaaggc ttccctgcat cgttgaattc ataggttaca ggggaggaag aggttttccc    300
ttcgattggc tcttctggag cagtgcgggg tatgcccatt cgtgatgga cactcgcggc    360
```

```
cagggaacca gtagagtaaa gggtgatact cctgactact gtgatgaacc cataaatcct    420
caattccccg gattcatgac gcggggaata ctggatccca ggacttacta ttacagaaga    480
gtttttaccg atgctgtaag agcagtggaa accgcttcga gtttcccggg aatagatccc    540
gaaaggatag ccgtcgtggg aacaagccag ggtgggggaa ttgcattggc ggtggcggcg    600
ctttccgaaa ttccaaaggc tcttgtatcg aatgttccgt ttctgtgtca tttcagaaga    660
gcggttcaga taacagataa cgctccttac agtgagatag tgaattattt gaaagtccac    720
agagacaaag aggaaattgt gttcagaacg ctttcgtact tgatggagt gaactttgct    780 gcgagggcaa aaataccagc acttttctct gttgctctca tggacaaaac cgynccacct    840
tctacagttt ttgctgctta caaccattac gctggtccaa aagaaatcaa agtgtatcca    900
ttcaacgaac atgaaggtgg agaatctttc cagagaatgg aggaacttcg ctttatgaaa    960
aggattctaa aagggggaatt caaagcatga                                    990
```

<210> SEQ ID NO 27
<211> LENGTH: 990
<212> TYPE: DNA
<213> ORGANISM: Thermotoga sp. RQ2b
<220> FEATURE:
<221> NAME/KEY: misc_feature
<222> LOCATION: (834)..(834)
<223> OTHER INFORMATION: n is a, g, c, or t.

<400> SEQUENCE: 27

```
atggcgctat ttgatatgcc tctggaaaag ttaagatcat accttcccga tagatacgag     60
gaggaagatt ttgatctgtt ctggaaagag actcttgagg agtcaagaaa attcccactg    120
gatcctattt ttgaaagagt agattatctg ctggagaacg tggaagtata cgatgtcacc    180
ttctccggtt acagggggtca aagaataaag gcgtggttga ttctaccggt tgttaagaag    240
gaagaaaggc ttccctgcat cgttgaattc ataggttaca ggggaggaag aggttttccc    300
ttcgattggc tcttctggag cagtgcgggg tatgcccatt tcgtgatgga cactcgcggc    360
cagggaacca gtagagtaaa gggtgatact cctgactact gtgatgaacc cataaatcct    420
caattccccg gattcatgac gcggggaata ctggatccca ggacttacta ttacagaaga    480
gtttttaccg atgctgtaag agcagtggaa accgcttcga gtttcccggg aatagatccc    540
gaaaggatag ccgtcgtggg aacaagccag ggtgggggaa ttgcattggc ggtggcggcg    600
ctttccgaaa ttccaaaggc tcttgtatcg aatgttccgt ttctgtgtca tttcagaaga    660
gcggttcaga taacagataa cgctccttac agtgagatag tgaattattt gaaagtccac    720
agagacaaag aggaaattgt gttcagaacg ctttcgtact tgatggagt gaactttgct    780 gcgagggcaa aaataccagc acttttctct gttgctctca tggacaaaac ctcnccacct    840
tctacagttt ttgctgctta caaccattac gctggtccaa aagaaatcaa agtgtatcca    900
ttcaacgaac atgaaggtgg agaatctttc cagagaatgg aggaacttcg ctttatgaaa    960
aggattctaa aagggggaatt caaagcatga                                    990
```

<210> SEQ ID NO 28
<211> LENGTH: 990
<212> TYPE: DNA
<213> ORGANISM: Thermotoga sp. RQ2b

<400> SEQUENCE: 28

```
atggcgctat ttgatatgcc tctggaaaag ttaagatcat accttcccga tagatacgag     60
gaggaagatt ttgatctgtt ctggaaagag actcttgagg agtcaagaaa attcccactg    120
```

```
gatcctatt   ttgaaagagt  agattatctg  ctggagaacg  tggaagtata  cgatgtcacc     180
ttctccggtt  acaggggtca  aagaataaag  gcgtggttga  ttctaccggt  tgttaagaag     240
gaagaaaggc  ttccctgcat  cgttgaattc  ataggttaca  ggggaggaag  aggttttccc     300
ttcgattggc  tcttctggag  cagtgcgggg  tatgcccatt  tcgtgatgga  cactcgcggc     360
cagggaacca  gtagagtaaa  gggtgatact  cctgactact  gtgatgaacc  cataaatcct     420
caattccccg  gattcatgac  gcggggaata  ctggatccca  ggacttacta  ttacagaaga     480 gttttaccg   atgctgtaag  agcagtggaa  accgcttcga  gtttcccggg  aatagatccc     540
gaaaggatag  ccgtcgtggg  aacaagccag  ggtgggggaa  ttgcattggc  ggtggcggcg     600
ctttccgaaa  ttccaaaggc  tcttgtatcg  aatgttccgt  ttctgtgtca  tttcagaaga     660
gcggttcaga  taacagataa  cgctccttac  agtgagatag  tgaattattt  gaaagtccac     720
agagacaaag  aggaaattgt  gttcagaacg  ctttcgtact  tgatggagt   gaactttgct     780 gcgagggcaa  aaataccagc  acttttctct  gttgctctca  tggacaaaac  cagyccacct    840
tctacagttt  ttgctgctta  caaccattac  gctggtccaa  agaaatcaa   agtgtatcca     900 ttcaacgaac  atgaaggtgg  agaatctttc  cagagaatgg  aggaacttcg  ctttatgaaa     960
aggattctaa  aagggaattc  aaagcatga                                          990
```

<210> SEQ ID NO 29
<211> LENGTH: 990
<212> TYPE: DNA
<213> ORGANISM: Thermotoga sp. RQ2b
<220> FEATURE:
<221> NAME/KEY: misc_feature
<222> LOCATION: (834)..(834)
<223> OTHER INFORMATION: n is a, g, c, or t.

<400> SEQUENCE: 29

```
atggcgctat  ttgatatgcc  tctggaaaag  ttaagatcat  accttcccga  tagatacgag      60
gaggaagatt  ttgatctgtt  ctggaaagag  actcttgagg  agtcaagaaa  attcccactg     120 gatcctatt   ttgaaagagt  agattatctg  ctggagaacg  tggaagtata  cgatgtcacc     180
ttctccggtt  acaggggtca  aagaataaag  gcgtggttga  ttctaccggt  tgttaagaag     240
gaagaaaggc  ttccctgcat  cgttgaattc  ataggttaca  ggggaggaag  aggttttccc     300
ttcgattggc  tcttctggag  cagtgcgggg  tatgcccatt  tcgtgatgga  cactcgcggc     360
cagggaacca  gtagagtaaa  gggtgatact  cctgactact  gtgatgaacc  cataaatcct     420
caattccccg  gattcatgac  gcggggaata  ctggatccca  ggacttacta  ttacagaaga     480 gttttaccg   atgctgtaag  agcagtggaa  accgcttcga  gtttcccggg  aatagatccc     540
gaaaggatag  ccgtcgtggg  aacaagccag  ggtgggggaa  ttgcattggc  ggtggcggcg     600
ctttccgaaa  ttccaaaggc  tcttgtatcg  aatgttccgt  ttctgtgtca  tttcagaaga     660
gcggttcaga  taacagataa  cgctccttac  agtgagatag  tgaattattt  gaaagtccac     720
agagacaaag  aggaaattgt  gttcagaacg  ctttcgtact  tgatggagt   gaactttgct     780 gcgagggcaa  aaataccagc  acttttctct  gttgctctca  tggacaaaac  cacnccacct    840
tctacagttt  ttgctgctta  caaccattac  gctggtccaa  agaaatcaa   agtgtatcca     900 ttcaacgaac  atgaaggtgg  agaatctttc  cagagaatgg  aggaacttcg  ctttatgaaa     960
aggattctaa  aagggaattc  aaagcatga                                          990
```

<210> SEQ ID NO 30
<211> LENGTH: 329
<212> TYPE: PRT

<213> ORGANISM: Thermotoga sp. RQ2b
<220> FEATURE:
<221> NAME/KEY: MISC_FEATURE
<222> LOCATION: (278)..(278)
<223> OTHER INFORMATION: Xaa is Ala, Val, Ser, or Thr.

<400> SEQUENCE: 30

```
Met Ala Leu Phe Asp Met Pro Leu Glu Lys Leu Arg Ser Tyr Leu Pro
 1               5                  10                  15

Asp Arg Tyr Glu Glu Asp Phe Asp Leu Phe Trp Lys Glu Thr Leu
             20                  25                  30

Glu Glu Ser Arg Lys Phe Pro Leu Asp Pro Ile Phe Glu Arg Val Asp
             35                  40                  45

Tyr Leu Leu Glu Asn Val Glu Val Tyr Asp Val Thr Phe Ser Gly Tyr
 50                  55                  60

Arg Gly Gln Arg Ile Lys Ala Trp Leu Ile Leu Pro Val Val Lys Lys
 65                  70                  75                  80

Glu Glu Arg Leu Pro Cys Ile Val Glu Phe Ile Gly Tyr Arg Gly Gly
                 85                  90                  95

Arg Gly Phe Pro Phe Asp Trp Leu Phe Trp Ser Ser Ala Gly Tyr Ala
                100                 105                 110

His Phe Val Met Asp Thr Arg Gly Gln Gly Thr Ser Arg Val Lys Gly
             115                 120                 125

Asp Thr Pro Asp Tyr Cys Asp Glu Pro Ile Asn Pro Gln Phe Pro Gly
130                 135                 140

Phe Met Thr Arg Gly Ile Leu Asp Pro Arg Thr Tyr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
                180                 185                 190

Gly Ile Ala Leu Ala Val Ala Ala Leu Ser Glu Ile Pro Lys Ala Leu
            195                 200                 205

Val Ser Asn Val Pro Phe Leu Cys His Phe Arg Arg Ala Val Gln Ile
210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Xaa Pro Pro Ser Thr Val Phe Ala Ala Tyr Asn
275                 280                 285

His Tyr Ala Gly Pro Lys Glu Ile Lys Val Tyr Pro Phe Asn Glu His
            290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325
```

<210> SEQ ID NO 31
<211> LENGTH: 136
<212> TYPE: PRT
<213> ORGANISM: Artificial Sequence
<220> FEATURE:
<223> OTHER INFORMATION: Thermotoga C-terminal consensus sequence
<220> FEATURE:
<221> NAME/KEY: MISC_FEATURE

```
<222> LOCATION: (2)..(2)
<223> OTHER INFORMATION: Xaa is any amino acid.
<220> FEATURE:
<221> NAME/KEY: MISC_FEATURE
<222> LOCATION: (13)..(13)
<223> OTHER INFORMATION: Xaa is any amino acid.
<220> FEATURE:
<221> NAME/KEY: MISC_FEATURE
<222> LOCATION: (17)..(20)
<223> OTHER INFORMATION: Xaa is any amino acid.
<220> FEATURE:
<221> NAME/KEY: MISC_FEATURE
<222> LOCATION: (23)..(25)
<223> OTHER INFORMATION: Xaa is any amino acid.
<220> FEATURE:
<221> NAME/KEY: MISC_FEATURE
<222> LOCATION: (32)..(33)
<223> OTHER INFORMATION: Xaa is any amino acid.
<220> FEATURE:
<221> NAME/KEY: MISC_FEATURE
<222> LOCATION: (38)..(39)
<223> OTHER INFORMATION: Xaa is any amino acid.
<220> FEATURE:
<221> NAME/KEY: MISC_FEATURE
<222> LOCATION: (41)..(42)
<223> OTHER INFORMATION: Xaa is any amino acid.
<220> FEATURE:
<221> NAME/KEY: MISC_FEATURE
<222> LOCATION: (45)..(45)
<223> OTHER INFORMATION: Xaa is any amino acid.
<220> FEATURE:
<221> NAME/KEY: MISC_FEATURE
<222> LOCATION: (48)..(51)
<223> OTHER INFORMATION: Xaa is any amino acid.
<220> FEATURE:
<221> NAME/KEY: MISC_FEATURE
<222> LOCATION: (53)..(53)
<223> OTHER INFORMATION: Xaa is any amino acid.
<220> FEATURE:
<221> NAME/KEY: MISC_FEATURE
<222> LOCATION: (55)..(55)
<223> OTHER INFORMATION: Xaa is any amino acid.
<220> FEATURE:
<221> NAME/KEY: MISC_FEATURE
<222> LOCATION: (58)..(58)
<223> OTHER INFORMATION: Xaa is any amino acid.
<220> FEATURE:
<221> NAME/KEY: MISC_FEATURE
<222> LOCATION: (59)..(60)
<223> OTHER INFORMATION: Xaa is any amino acid.
<220> FEATURE:
<221> NAME/KEY: MISC_FEATURE
<222> LOCATION: (75)..(75)
<223> OTHER INFORMATION: Xaa is any amino acid.
<220> FEATURE:
<221> NAME/KEY: MISC_FEATURE
<222> LOCATION: (79)..(79)
<223> OTHER INFORMATION: Xaa is any amino acid.
<220> FEATURE:
<221> NAME/KEY: MISC_FEATURE
<222> LOCATION: (86)..(86)
<223> OTHER INFORMATION: Xaa is any amino acid.
<220> FEATURE:
<221> NAME/KEY: MISC_FEATURE
<222> LOCATION: (90)..(91)
<223> OTHER INFORMATION: Xaa is any amino acid.
<220> FEATURE:
<221> NAME/KEY: MISC_FEATURE
<222> LOCATION: (104)..(104)
<223> OTHER INFORMATION: Xaa is any amino acid.
<220> FEATURE:
<221> NAME/KEY: MISC_FEATURE
<222> LOCATION: (108)..(108)
<223> OTHER INFORMATION: Xaa is any amino acid.
<220> FEATURE:
<221> NAME/KEY: MISC_FEATURE
<222> LOCATION: (110)..(110)
<223> OTHER INFORMATION: Xaa is any amino acid.
<220> FEATURE:
<221> NAME/KEY: MISC_FEATURE
```

```
<222> LOCATION: (112)..(113)
<223> OTHER INFORMATION: Xaa is any amino acid.
<220> FEATURE:
<221> NAME/KEY: MISC_FEATURE
<222> LOCATION: (116)..(116)
<223> OTHER INFORMATION: Xaa is any amino acid.
<220> FEATURE:
<221> NAME/KEY: MISC_FEATURE
<222> LOCATION: (118)..(118)
<223> OTHER INFORMATION: Xaa is any amino acid.
<220> FEATURE:
<221> NAME/KEY: MISC_FEATURE
<222> LOCATION: (123)..(123)
<223> OTHER INFORMATION: Xaa is any amino acid.
<220> FEATURE:
<221> NAME/KEY: MISC_FEATURE
<222> LOCATION: (126)..(128)
<223> OTHER INFORMATION: Xaa is any amino acid.
<220> FEATURE:
<221> NAME/KEY: MISC_FEATURE
<222> LOCATION: (130)..(132)
<223> OTHER INFORMATION: Xaa is any amino acid.
<220> FEATURE:
<221> NAME/KEY: MISC_FEATURE
<222> LOCATION: (134)..(134)
<223> OTHER INFORMATION: Xaa is any amino acid.
<220> FEATURE:
<221> NAME/KEY: MISC_FEATURE
<222> LOCATION: (136)..(136)
<223> OTHER INFORMATION: Xaa is any amino acid.

<400> SEQUENCE: 31

Gly Xaa Ser Gln Gly Gly Gly Ile Ala Leu Ala Val Xaa Ala Leu Ser
1               5                   10                  15

Xaa Xaa Xaa Xaa Ala Leu Xaa Xaa Val Pro Phe Leu Cys His Xaa
            20                  25                  30

Xaa Arg Ala Val Gln Xaa Xaa Asp Xaa Xaa Pro Tyr Xaa Glu Ile Xaa
            35                  40                  45

Xaa Xaa Xaa Lys Xaa His Xaa Asp Lys Xaa Xaa Xaa Val Phe Arg Thr
    50                  55                  60

Leu Ser Tyr Phe Asp Gly Val Asn Phe Ala Xaa Arg Ala Lys Xaa Pro
65                  70                  75                  80

Ala Leu Phe Ser Val Xaa Leu Met Asp Xaa Xaa Ile Cys Pro Pro Ser
                85                  90                  95

Thr Tyr Phe Ala Ala Tyr Asn Xaa Tyr Ala Gly Xaa Lys Xaa Ile Xaa
                100                 105                 110

Xaa Tyr Pro Xaa Asn Xaa His Glu Gly Gly Xaa Ser Phe Xaa Xaa Xaa
        115                 120                 125

Glu Xaa Xaa Xaa Phe Xaa Lys Xaa
    130                 135

<210> SEQ ID NO 32
<211> LENGTH: 325
<212> TYPE: PRT
<213> ORGANISM: Thermotoga neapolitana

<400> SEQUENCE: 32

Met Ala Phe Phe Asp Met Pro Leu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
            35                  40                  45

Phe His Leu Lys Thr Val Glu Thr Tyr Asp Val Thr Phe Ser Gly Tyr
    50                  55                  60
```

Arg Gly Gln Arg Ile Lys Gly Trp Leu Leu Val Pro Lys Leu Ala Glu
 65                  70                  75                  80

Glu Lys Leu Pro Cys Val Val Gln Tyr Ile Gly Tyr Asn Gly Gly Arg
             85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Ser Gln Gly Gly Gly
            180                 185                 190

Ile Ala Leu Ala Val Ser Ala Leu Ser Asn Arg Val Lys Ala Leu Leu
            195                 200                 205

Cys Asp Val Pro Phe Leu Cys His Phe Arg Arg Ala Val Gln Leu Val
210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
                325

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33
atggctttct ttgacatgcc gctg                                    24

<210> SEQ ID NO 34
<211> LENGTH: 27
<212> TYPE: DNA
<213> ORGANISM: Artificial Sequence
<220> FEATURE:
<223> OTHER INFORMATION: Primer

<400> SEQUENCE: 34
ttagccttct tcgaacaggc gtttcag                                 27

<210> SEQ ID NO 35
<211> LENGTH: 978
<212> TYPE: DNA
<213> ORGANISM: Thermotoga neapolitana

<400> SEQUENCE: 35

```
atggctttct tgacatgcc gctggaagaa ctgaaaaagt accgtccgga acgttacgag      60
gaaaaagact ttgacgaatt ttggcgcgaa accctgaaag aatccgaggg tttcccactg    120
gacccggtat ttgaaaaagt tgacttccac ctgaagaccg tcgaaactta cgacgtcacc    180
ttcagcggtt atcgtggcca gcgtatcaaa ggttggctgc tggtaccgaa actggcggaa    240
gagaaactgc cgtgtgttgt tcagtacatt ggttacaacg gtggccgtgg tttcccgcac    300
gactggctgt tctggccgtc tatgggttac atctgcttcg ttatggacac ccgtggtcag    360
ggtagcggtt ggatgaaggg tgatactccg gactacccgg aaggtccggt ggacccgcag    420
taccccgggct tcatgacgcg cggcatcctg gatcctggca cctattacta ccgtcgtgtg    480
tttgtcgatg ccgtgcgcgc cgttgaagcc gctatcagct ccccacgcgt cgattctcgt    540
aaagtggtag ttgctggtgg ctctcaaggt ggcggcattg cactggcagt tccgcgctg     600
tccaaccgtg ttaaagccct gctgtgcgat gttccgttcc tgtgccactt ccgtcgtgcg    660
gtacagctgg tggacaccca cccgtacgta gaaattacga acttcctgaa acccatcgt     720
gataaagaag agatcgtatt ccgtaccctg tcttactttg atggcgttaa ttttgcggct    780
cgtgcaaaag taccggcgct gttcagcgta ggtctgatgg acactatttg tccgccgtct    840
accgtattcg cagcctacaa ccactacgct ggtccgaaag aaatccgcat ctacccgtac    900
aacaaccacg aaggtggtgg ttctttccag gcaatcgaac aggttaaatt cctgaaacgc    960
ctgttcgaag aaggctaa                                                 978
```

<210> SEQ ID NO 36
<211> LENGTH: 325
<212> TYPE: PRT
<213> ORGANISM: Thermotoga maritima

<400> SEQUENCE: 36

```
Met Ala Phe Phe Asp Leu Pro Leu Glu Glu Leu Lys Lys Tyr Arg Pro
  1               5                  10                  15

Glu Arg Tyr Glu Glu Lys Asp Phe Asp Glu Phe Trp Glu Glu Thr Leu
             20                  25                  30

Ala Glu Ser Glu Lys Phe Pro Leu Asp Pro Val Phe Glu Arg Met Glu
         35                  40                  45

Ser His Leu Lys Thr Val Glu Ala Tyr Asp Val Thr Phe Ser Gly Tyr
     50                  55                  60

Arg Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190
```

```
Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
        210                 215                 220

Asp Thr His Pro Tyr Ala Glu Ile Thr Asn Phe Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Cys Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 37
<211> LENGTH: 978
<212> TYPE: DNA
<213> ORGANISM: Thermotoga maritima

<400> SEQUENCE: 37
atggccttct tcgatttacc actcgaagaa ctgaagaaat atcgtccaga gcggtacgaa      60
gagaaagact tcgatgagtt ctgggaagag acactcgcag agagcgaaaa gttcccctta     120
gaccccgtct tcgagaggat ggagtctcac ctcaaaacag tcgaagcgta cgatgtcacc     180
ttctccggat acaggggaca gaggatcaaa gggtggctcc ttgttccaaa actggaagaa     240
gaaaaacttc cctgcgttgt gcagtacata ggatacaacg gtggaagagg attccctcac     300
gactggctgt tctggccttc tatgggttac atatgtttcg tcatggatac tcgaggtcag     360
ggaagcggct ggctgaaagg agacacaccg gattaccctg agggtcccgt tgaccctcag     420
tatccaggat tcatgacaag aggaatactg atcccagaa cttactacta cagacgagtc     480 ttcacgacg ctgtcagagc cgttgaagct gctgcttctt ttcctcaggt agatcaagaa     540
agaatcgtga tagctggagg cagtcagggt ggcggaatag cccttgcggt gagcgctctc     600
tcaaagaaag caaaggctct tctgtgcgat gtgccgtttc tgtgtcactt cagaagagca     660
gtacagcttg tggatacgca tccatacgcg gagatcacga actttctaaa gacccacaga     720
gacaaggaag aaatcgtgtt caggactctt tcctatttcg atggagtgaa cttcgcagcc     780
agagcgaaga tccctgcgct gttttctgtg gtctcatgg acaacatttg tcctccttca     840
acggttttcg ctgcctacaa ttactacgct ggaccgaagg aaatcagaat ctatccgtac     900
aacaaccacg agggaggagg ctctttccaa gcggttgaac aggtgaaatt cttgaaaaaa     960
ctatttgaga aaggctaa                                                    978

<210> SEQ ID NO 38
<211> LENGTH: 47
<212> TYPE: DNA
<213> ORGANISM: Artificial Sequence
<220> FEATURE:
<223> OTHER INFORMATION: Primer

<400> SEQUENCE: 38
```

```
taagaattct aaggaatagg acatggcgtt tcttcgacct gcctctg        47
```

<210> SEQ ID NO 39
<211> LENGTH: 36
<212> TYPE: DNA
<213> ORGANISM: Artificial Sequence
<220> FEATURE:
<223> OTHER INFORMATION: Primer

<400> SEQUENCE: 39

```
aaactgcagt tagcccttct caaacagttt cttcag                    36
```

<210> SEQ ID NO 40
<211> LENGTH: 978
<212> TYPE: DNA
<213> ORGANISM: Artificial Sequence
<220> FEATURE:
<223> OTHER INFORMATION: Codon optimized sequence

<400> SEQUENCE: 40

```
atggctttct ttgacatgcc gctggaagaa ctgaaaaagt accgtccgga acgttacgag    60
gaaaaagact tgacgaatt ttggcgcgaa accctgaaag aatccgaggg tttcccactg    120
gacccggtat ttgaaaaagt tgacttccac ctgaagaccg tcgaaactta cgacgtcacc   180
ttcagcggtt atcgtggcca gcgtatcaaa ggttggctgc tggtaccgaa actggcggaa   240
gagaaactgc cgtgtgttgt tcagtacatt ggttacaacg gtggccgtgg tttcccgcac   300
gactggctgt tctggccgtc tatgggttac atctgcttcg ttatggacac ccgtggtcag   360
ggtagcggtt ggatgaaggg tgatactccg gactacccgg aaggtccggt ggacccgcag   420
tacccgggct tcatgacgcg cggcatcctg gatcctggca cctattacta ccgtcgtgtg   480
tttgtcgatg ccgtgcgcgc cgttgaagcc gctatcagct cccacgcgt cgattctcgt    540
aaagtggtag ttgctggtgg ctctcaaggt ggcggcattg cactggcagt ttccgcgctg   600
tccaaccgtg ttaaagccct gctgtgcgat gttccgttcc tgtgccactt ccgtcgtgcg   660
gtacagctgg tggacacccca cccgtacgta gaaattacga acttcctgaa aacccatcgt   720
gataaagaag agatcgtatt ccgtaccctg tcttactttg atggcgttaa ttttgcggct   780
cgtgcaaaag taccggcgct gttcagcgta ggtctgatgg acactatttg tccgccgtct   840
accgtattcg cagcctacaa ccactacgct ggtccgaaag aaatccgcat ctacccgtac   900
aacaaccacg aaggtggtgg ttctttccag gcaatcgaac aggttaaatt cctgaaacgc   960
ctgttcgaag aaggctaa                                                978
```

<210> SEQ ID NO 41
<211> LENGTH: 975
<212> TYPE: DNA
<213> ORGANISM: Artificial Sequence
<220> FEATURE:
<223> OTHER INFORMATION: Codon optimized sequence

<400> SEQUENCE: 41

```
atggcgttct tcgacctgcc tctggaagaa ctgaagaaat accgtccaga gcgttacgaa    60
gagaaggact tcgacgagtt ctgggaggaa actctggcgg agagcgaaaa gtttccgctg   120
gacccagtgt tcgagcgtat ggaatctcac ctgaaaaccg tggaggcata tgacgttact   180
ttttctggtt accgtggcca gcgtatcaaa ggctggctgc tggttccgaa actggaggaa   240
gaaaaactgc cgtgcgtagt tcagtacatc ggttacaacg gtggccgtgg ctttccgcac   300
gattggctgt tctggccgtc tatgggctac atttgcttcg tcatggatac tcgtggtcag   360
```

-continued

```
ggttccggct ggctgaaagg cgatactccg gattatccgg agggcccggt agacccgcag    420 tacccctggct tcatgacgcg tggtattctg gatccgcgta cctattacta tcgccgcgtt    480
tttaccgatg cagttcgtgc cgtagaggcc gcggcttctt tccctcaggt tgaccaggag    540
cgtattgtta tcgctggtgg ctcccagggt ggcggcatcg ccctggcggt atctgcgctg    600
agcaagaaag ctaaggcact gctgtgtgac gtcccgttcc tgtgtcactt ccgtcgcgct    660
gttcagctgg tagatacccca tccgtacgcg gagattacta acttcctgaa aactcaccgc    720
gacaaagaag aaatcgtttt ccgcaccctg tcctatttcg acggcgttaa cttcgcggct    780
cgtgcaaaaa ttccggcact gttctctgtt ggtctgatgg acaacatctg ccctccttct    840
accgttttcg cggcatataa ctattatgcg ggtccgaaag aaatccgtat ctatccgtac    900
aacaaccacg aaggcggtgg tagctttcag gctgttgaac aagtgaaatt cctgaagaaa    960 ctgttttgaga agggc                                                    975
```

<210> SEQ ID NO 42
<211> LENGTH: 23
<212> TYPE: DNA
<213> ORGANISM: Artificial Sequence
<220> FEATURE:
<223> OTHER INFORMATION: Primer

<400> SEQUENCE: 42
ggacactatt ggcccgccgt cta    23

<210> SEQ ID NO 43
<211> LENGTH: 23
<212> TYPE: DNA
<213> ORGANISM: Artificial Sequence
<220> FEATURE:
<223> OTHER INFORMATION: Primer

<400> SEQUENCE: 43
tagacggcgg gccaatagtg tcc    23

<210> SEQ ID NO 44
<211> LENGTH: 23
<212> TYPE: DNA
<213> ORGANISM: Artificial Sequence
<220> FEATURE:
<223> OTHER INFORMATION: Primer

<400> SEQUENCE: 44
ggacactatt gcgccgccgt cta    23

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
tagacggcgg cgcaatagtg tcc    23

<210> SEQ ID NO 46
<211> LENGTH: 23
<212> TYPE: DNA
<213> ORGANISM: Artificial Sequence
<220> FEATURE:
<223> OTHER INFORMATION: Primer

<400> SEQUENCE: 46

```
ggacactatt gtgccgccgt cta                                              23

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
tagacggcgg cacaatagtg tcc                                              23

<210> SEQ ID NO 48
<211> LENGTH: 23
<212> TYPE: DNA
<213> ORGANISM: Artificial Sequence
<220> FEATURE:
<223> OTHER INFORMATION: Primer

<400> SEQUENCE: 48
ggacactatt ctgccgccgt cta                                              23

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49
tagacggcgg cagaatagtg tcc                                              23

<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
ggacactatt attccgccgt cta                                              23

<210> SEQ ID NO 51
<211> LENGTH: 23
<212> TYPE: DNA
<213> ORGANISM: Artificial Sequence
<220> FEATURE:
<223> OTHER INFORMATION: Primer

<400> SEQUENCE: 51
tagacggcgg aataatagtg tcc                                              23

<210> SEQ ID NO 52
<211> LENGTH: 23
<212> TYPE: DNA
<213> ORGANISM: Artificial Sequence
<220> FEATURE:
<223> OTHER INFORMATION: Primer

<400> SEQUENCE: 52
ggacactatt ccgccgccgt cta                                              23

<210> SEQ ID NO 53
<211> LENGTH: 23
<212> TYPE: DNA
<213> ORGANISM: Artificial Sequence
<220> FEATURE:
```

-continued

<223> OTHER INFORMATION: Primer

<400> SEQUENCE: 53
tagacggcgg cggaatagtg tcc                                             23

<210> SEQ ID NO 54
<211> LENGTH: 23
<212> TYPE: DNA
<213> ORGANISM: Artificial Sequence
<220> FEATURE:
<223> OTHER INFORMATION: Primer

<400> SEQUENCE: 54
ggacactatt tttccgccgt cta                                             23

<210> SEQ ID NO 55
<211> LENGTH: 23
<212> TYPE: DNA
<213> ORGANISM: Artificial Sequence
<220> FEATURE:
<223> OTHER INFORMATION: Primer

<400> SEQUENCE: 55
tagacggcgg aaaaatagtg tcc                                             23

<210> SEQ ID NO 56
<211> LENGTH: 23
<212> TYPE: DNA
<213> ORGANISM: Artificial Sequence
<220> FEATURE:
<223> OTHER INFORMATION: Primer

<400> SEQUENCE: 56
ggacactatt tatccgccgt cta                                             23

<210> SEQ ID NO 57
<211> LENGTH: 23
<212> TYPE: DNA
<213> ORGANISM: Artificial Sequence
<220> FEATURE:
<223> OTHER INFORMATION: Primer

<400> SEQUENCE: 57
tagacggcgg ataaatagtg tcc                                             23

<210> SEQ ID NO 58
<211> LENGTH: 23
<212> TYPE: DNA
<213> ORGANISM: Artificial Sequence
<220> FEATURE:
<223> OTHER INFORMATION: Primer

<400> SEQUENCE: 58
ggacactatt tggccgccgt cta                                             23

<210> SEQ ID NO 59
<211> LENGTH: 23
<212> TYPE: DNA
<213> ORGANISM: Artificial Sequence
<220> FEATURE:
<223> OTHER INFORMATION: Primer

<400> SEQUENCE: 59
tagacggcgg ccaaatagtg tcc                                             23

<210> SEQ ID NO 60

```
<211> LENGTH: 23
<212> TYPE: DNA
<213> ORGANISM: Artificial Sequence
<220> FEATURE:
<223> OTHER INFORMATION: Primer

<400> SEQUENCE: 60
ggacactatt agcccgccgt cta                                              23

<210> SEQ ID NO 61
<211> LENGTH: 23
<212> TYPE: DNA
<213> ORGANISM: Artificial Sequence
<220> FEATURE:
<223> OTHER INFORMATION: Primer

<400> SEQUENCE: 61
tagacggcgg gctaatagtg tcc                                              23

<210> SEQ ID NO 62
<211> LENGTH: 23
<212> TYPE: DNA
<213> ORGANISM: Artificial Sequence
<220> FEATURE:
<223> OTHER INFORMATION: Primer

<400> SEQUENCE: 62
ggacactatt accccgccgt cta                                              23

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
tagacggcgg ggtaatagtg tcc                                              23

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
ggacactatt cagccgccgt cta                                              23

<210> SEQ ID NO 65
<211> LENGTH: 23
<212> TYPE: DNA
<213> ORGANISM: Artificial Sequence
<220> FEATURE:
<223> OTHER INFORMATION: Primer

<400> SEQUENCE: 65
tagacggcgg ctgaatagtg tcc                                              23

<210> SEQ ID NO 66
<211> LENGTH: 23
<212> TYPE: DNA
<213> ORGANISM: Artificial Sequence
<220> FEATURE:
<223> OTHER INFORMATION: Primer

<400> SEQUENCE: 66
```
ggacactatt aacccgccgt cta                                              23

<210> SEQ ID NO 67
<211> LENGTH: 23
<212> TYPE: DNA
<213> ORGANISM: Artificial Sequence
<220> FEATURE:
<223> OTHER INFORMATION: Primer

<400> SEQUENCE: 67
tagacggcgg gttaatagtg tcc                                              23

<210> SEQ ID NO 68
<211> LENGTH: 23
<212> TYPE: DNA
<213> ORGANISM: Artificial Sequence
<220> FEATURE:
<223> OTHER INFORMATION: Primer

<400> SEQUENCE: 68
ggacactatt gatccgccgt cta                                              23

<210> SEQ ID NO 69
<211> LENGTH: 23
<212> TYPE: DNA
<213> ORGANISM: Artificial Sequence
<220> FEATURE:
<223> OTHER INFORMATION: Primer

<400> SEQUENCE: 69
tagacggcgg atcaatagtg tcc                                              23

<210> SEQ ID NO 70
<211> LENGTH: 23
<212> TYPE: DNA
<213> ORGANISM: Artificial Sequence
<220> FEATURE:
<223> OTHER INFORMATION: Primer

<400> SEQUENCE: 70
ggacactatt gaaccgccgt cta                                              23

<210> SEQ ID NO 71
<211> LENGTH: 23
<212> TYPE: DNA
<213> ORGANISM: Artificial Sequence
<220> FEATURE:
<223> OTHER INFORMATION: Primer

<400> SEQUENCE: 71
tagacggcgg ttcaatagtg tcc                                              23

<210> SEQ ID NO 72
<211> LENGTH: 23
<212> TYPE: DNA
<213> ORGANISM: Artificial Sequence
<220> FEATURE:
<223> OTHER INFORMATION: Primer

<400> SEQUENCE: 72
ggacactatt cgtccgccgt cta                                              23

<210> SEQ ID NO 73
<211> LENGTH: 23
<212> TYPE: DNA
<213> ORGANISM: Artificial Sequence
<220> FEATURE:

<223> OTHER INFORMATION: Primer

<400> SEQUENCE: 73
tagacggcgg acgaatagtg tcc                                          23

<210> SEQ ID NO 74
<211> LENGTH: 23
<212> TYPE: DNA
<213> ORGANISM: Artificial Sequence
<220> FEATURE:
<223> OTHER INFORMATION: Primer

<400> SEQUENCE: 74
ggacactatt catccgccgt cta                                          23

<210> SEQ ID NO 75
<211> LENGTH: 23
<212> TYPE: DNA
<213> ORGANISM: Artificial Sequence
<220> FEATURE:
<223> OTHER INFORMATION: Primer

<400> SEQUENCE: 75
tagacggcgg atgaatagtg tcc                                          23

<210> SEQ ID NO 76
<211> LENGTH: 23
<212> TYPE: DNA
<213> ORGANISM: Artificial Sequence
<220> FEATURE:
<223> OTHER INFORMATION: Primer

<400> SEQUENCE: 76
ggacactatt aaaccgccgt cta                                          23

<210> SEQ ID NO 77
<211> LENGTH: 23
<212> TYPE: DNA
<213> ORGANISM: Artificial Sequence
<220> FEATURE:
<223> OTHER INFORMATION: Primer

<400> SEQUENCE: 77
tagacggcgg tttaatagtg tcc                                          23

<210> SEQ ID NO 78
<211> LENGTH: 23
<212> TYPE: DNA
<213> ORGANISM: Artificial Sequence
<220> FEATURE:
<223> OTHER INFORMATION: Primer

<400> SEQUENCE: 78
ggacactatt atgccgccgt cta                                          23

<210> SEQ ID NO 79
<211> LENGTH: 23
<212> TYPE: DNA
<213> ORGANISM: Artificial Sequence
<220> FEATURE:
<223> OTHER INFORMATION: Primer

<400> SEQUENCE: 79
tagacggcgg cataatagtg tcc                                          23

<210> SEQ ID NO 80

```
<211> LENGTH: 23
<212> TYPE: DNA
<213> ORGANISM: Artificial Sequence
<220> FEATURE:
<223> OTHER INFORMATION: Primer

<400> SEQUENCE: 80
gatggacact ggctgtccgc cgt                                              23

<210> SEQ ID NO 81
<211> LENGTH: 23
<212> TYPE: DNA
<213> ORGANISM: Artificial Sequence
<220> FEATURE:
<223> OTHER INFORMATION: Primer

<400> SEQUENCE: 81
acggcggaca gccagtgtcc atc                                              23

<210> SEQ ID NO 82
<211> LENGTH: 23
<212> TYPE: DNA
<213> ORGANISM: Artificial Sequence
<220> FEATURE:
<223> OTHER INFORMATION: Primer

<400> SEQUENCE: 82
gatggacact gcgtgtccgc cgt                                              23

<210> SEQ ID NO 83
<211> LENGTH: 23
<212> TYPE: DNA
<213> ORGANISM: Artificial Sequence
<220> FEATURE:
<223> OTHER INFORMATION: Primer

<400> SEQUENCE: 83
acggcggaca cgcagtgtcc atc                                              23

<210> SEQ ID NO 84
<211> LENGTH: 23
<212> TYPE: DNA
<213> ORGANISM: Artificial Sequence
<220> FEATURE:
<223> OTHER INFORMATION: Primer

<400> SEQUENCE: 84
gatggacact gtgtgtccgc cgt                                              23

<210> SEQ ID NO 85
<211> LENGTH: 23
<212> TYPE: DNA
<213> ORGANISM: Artificial Sequence
<220> FEATURE:
<223> OTHER INFORMATION: Primer

<400> SEQUENCE: 85
acggcggaca cacagtgtcc atc                                              23

<210> SEQ ID NO 86
<211> LENGTH: 23
<212> TYPE: DNA
<213> ORGANISM: Artificial Sequence
<220> FEATURE:
<223> OTHER INFORMATION: Primer

<400> SEQUENCE: 86
```

```
gatggacact ctgtgtccgc cgt                                                23

<210> SEQ ID NO 87
<211> LENGTH: 23
<212> TYPE: DNA
<213> ORGANISM: Artificial Sequence
<220> FEATURE:
<223> OTHER INFORMATION: Primer

<400> SEQUENCE: 87
acggcggaca cagagtgtcc atc                                                23

<210> SEQ ID NO 88
<211> LENGTH: 23
<212> TYPE: DNA
<213> ORGANISM: Artificial Sequence
<220> FEATURE:
<223> OTHER INFORMATION: Primer

<400> SEQUENCE: 88
gatggacact tgctgtccgc cgt                                                23

<210> SEQ ID NO 89
<211> LENGTH: 23
<212> TYPE: DNA
<213> ORGANISM: Artificial Sequence
<220> FEATURE:
<223> OTHER INFORMATION: Primer

<400> SEQUENCE: 89
acggcggaca gcaagtgtcc atc                                                23

<210> SEQ ID NO 90
<211> LENGTH: 23
<212> TYPE: DNA
<213> ORGANISM: Artificial Sequence
<220> FEATURE:
<223> OTHER INFORMATION: Primer

<400> SEQUENCE: 90
gatggacact ccgtgtccgc cgt                                                23

<210> SEQ ID NO 91
<211> LENGTH: 23
<212> TYPE: DNA
<213> ORGANISM: Artificial Sequence
<220> FEATURE:
<223> OTHER INFORMATION: Primer

<400> SEQUENCE: 91
acggcggaca cggagtgtcc atc                                                23

<210> SEQ ID NO 92
<211> LENGTH: 23
<212> TYPE: DNA
<213> ORGANISM: Artificial Sequence
<220> FEATURE:
<223> OTHER INFORMATION: Primer

<400> SEQUENCE: 92
gatggacact ttttgtccgc cgt                                                23

<210> SEQ ID NO 93
<211> LENGTH: 23
<212> TYPE: DNA
<213> ORGANISM: Artificial Sequence
<220> FEATURE:
```

<223> OTHER INFORMATION: Primer

<400> SEQUENCE: 93
acggcggaca aaaagtgtcc atc                                          23

<210> SEQ ID NO 94
<211> LENGTH: 23
<212> TYPE: DNA
<213> ORGANISM: Artificial Sequence
<220> FEATURE:
<223> OTHER INFORMATION: Primer

<400> SEQUENCE: 94
gatggacact tattgtccgc cgt                                          23

<210> SEQ ID NO 95
<211> LENGTH: 23
<212> TYPE: DNA
<213> ORGANISM: Artificial Sequence
<220> FEATURE:
<223> OTHER INFORMATION: Primer

<400> SEQUENCE: 95
acggcggaca ataagtgtcc atc                                          23

<210> SEQ ID NO 96
<211> LENGTH: 23
<212> TYPE: DNA
<213> ORGANISM: Artificial Sequence
<220> FEATURE:
<223> OTHER INFORMATION: Primer

<400> SEQUENCE: 96
gatggacact tggtgtccgc cgt                                          23

<210> SEQ ID NO 97
<211> LENGTH: 23
<212> TYPE: DNA
<213> ORGANISM: Artificial Sequence
<220> FEATURE:
<223> OTHER INFORMATION: Primer

<400> SEQUENCE: 97
acggcggaca ccaagtgtcc atc                                          23

<210> SEQ ID NO 98
<211> LENGTH: 23
<212> TYPE: DNA
<213> ORGANISM: Artificial Sequence
<220> FEATURE:
<223> OTHER INFORMATION: Primer

<400> SEQUENCE: 98
gatggacact agctgtccgc cgt                                          23

<210> SEQ ID NO 99
<211> LENGTH: 23
<212> TYPE: DNA
<213> ORGANISM: Artificial Sequence
<220> FEATURE:
<223> OTHER INFORMATION: Primer

<400> SEQUENCE: 99
acggcggaca gctagtgtcc atc                                          23

<210> SEQ ID NO 100

```
<211> LENGTH: 23
<212> TYPE: DNA
<213> ORGANISM: Artificial Sequence
<220> FEATURE:
<223> OTHER INFORMATION: Primer

<400> SEQUENCE: 100
gatggacact acctgtccgc cgt                                              23

<210> SEQ ID NO 101
<211> LENGTH: 23
<212> TYPE: DNA
<213> ORGANISM: Artificial Sequence
<220> FEATURE:
<223> OTHER INFORMATION: Primer

<400> SEQUENCE: 101
acggcggaca ggtagtgtcc atc                                              23

<210> SEQ ID NO 102
<211> LENGTH: 23
<212> TYPE: DNA
<213> ORGANISM: Artificial Sequence
<220> FEATURE:
<223> OTHER INFORMATION: Primer

<400> SEQUENCE: 102
gatggacact cagtgtccgc cgt                                              23

<210> SEQ ID NO 103
<211> LENGTH: 23
<212> TYPE: DNA
<213> ORGANISM: Artificial Sequence
<220> FEATURE:
<223> OTHER INFORMATION: Primer

<400> SEQUENCE: 103
acggcggaca ctgagtgtcc atc                                              23

<210> SEQ ID NO 104
<211> LENGTH: 23
<212> TYPE: DNA
<213> ORGANISM: Artificial Sequence
<220> FEATURE:
<223> OTHER INFORMATION: Primer

<400> SEQUENCE: 104
gatggacact aactgtccgc cgt                                              23

<210> SEQ ID NO 105
<211> LENGTH: 23
<212> TYPE: DNA
<213> ORGANISM: Artificial Sequence
<220> FEATURE:
<223> OTHER INFORMATION: Primer

<400> SEQUENCE: 105
acggcggaca gttagtgtcc atc                                              23

<210> SEQ ID NO 106
<211> LENGTH: 23
<212> TYPE: DNA
<213> ORGANISM: Artificial Sequence
<220> FEATURE:
<223> OTHER INFORMATION: Primer

<400> SEQUENCE: 106
```

```
gatggacact gattgtccgc cgt                                              23

<210> SEQ ID NO 107
<211> LENGTH: 23
<212> TYPE: DNA
<213> ORGANISM: Artificial Sequence
<220> FEATURE:
<223> OTHER INFORMATION: Primer

<400> SEQUENCE: 107
acggcggaca atcagtgtcc atc                                              23

<210> SEQ ID NO 108
<211> LENGTH: 23
<212> TYPE: DNA
<213> ORGANISM: Artificial Sequence
<220> FEATURE:
<223> OTHER INFORMATION: Primer

<400> SEQUENCE: 108
gatggacact gaatgtccgc cgt                                              23

<210> SEQ ID NO 109
<211> LENGTH: 23
<212> TYPE: DNA
<213> ORGANISM: Artificial Sequence
<220> FEATURE:
<223> OTHER INFORMATION: Primer

<400> SEQUENCE: 109
acggcggaca ttcagtgtcc atc                                              23

<210> SEQ ID NO 110
<211> LENGTH: 23
<212> TYPE: DNA
<213> ORGANISM: Artificial Sequence
<220> FEATURE:
<223> OTHER INFORMATION: Primer

<400> SEQUENCE: 110
gatggacact cgttgtccgc cgt                                              23

<210> SEQ ID NO 111
<211> LENGTH: 23
<212> TYPE: DNA
<213> ORGANISM: Artificial Sequence
<220> FEATURE:
<223> OTHER INFORMATION: Primer

<400> SEQUENCE: 111
acggcggaca acgagtgtcc atc                                              23

<210> SEQ ID NO 112
<211> LENGTH: 23
<212> TYPE: DNA
<213> ORGANISM: Artificial Sequence
<220> FEATURE:
<223> OTHER INFORMATION: Primer

<400> SEQUENCE: 112
gatggacact cattgtccgc cgt                                              23

<210> SEQ ID NO 113
<211> LENGTH: 23
<212> TYPE: DNA
<213> ORGANISM: Artificial Sequence
<220> FEATURE:
```

<223> OTHER INFORMATION: Primer

<400> SEQUENCE: 113
acggcggaca atgagtgtcc atc                                              23

<210> SEQ ID NO 114
<211> LENGTH: 23
<212> TYPE: DNA
<213> ORGANISM: Artificial Sequence
<220> FEATURE:
<223> OTHER INFORMATION: Primer

<400> SEQUENCE: 114
gatggacact aaatgtccgc cgt                                              23

<210> SEQ ID NO 115
<211> LENGTH: 23
<212> TYPE: DNA
<213> ORGANISM: Artificial Sequence
<220> FEATURE:
<223> OTHER INFORMATION: Primer

<400> SEQUENCE: 115
acggcggaca tttagtgtcc atc                                              23

<210> SEQ ID NO 116
<211> LENGTH: 23
<212> TYPE: DNA
<213> ORGANISM: Artificial Sequence
<220> FEATURE:
<223> OTHER INFORMATION: Primer

<400> SEQUENCE: 116
gatggacact atgtgtccgc cgt                                              23

<210> SEQ ID NO 117
<211> LENGTH: 23
<212> TYPE: DNA
<213> ORGANISM: Artificial Sequence
<220> FEATURE:
<223> OTHER INFORMATION: Primer

<400> SEQUENCE: 117
acggcggaca catagtgtcc atc                                              23

<210> SEQ ID NO 118
<211> LENGTH: 23
<212> TYPE: DNA
<213> ORGANISM: Artificial Sequence
<220> FEATURE:
<223> OTHER INFORMATION: Primer

<400> SEQUENCE: 118
cgatgttccg ggcctgtgcc act                                              23

<210> SEQ ID NO 119
<211> LENGTH: 23
<212> TYPE: DNA
<213> ORGANISM: Artificial Sequence
<220> FEATURE:
<223> OTHER INFORMATION: Primer

<400> SEQUENCE: 119
agtggcacag gcccggaaca tcg                                              23

<210> SEQ ID NO 120

```
<211> LENGTH: 23
<212> TYPE: DNA
<213> ORGANISM: Artificial Sequence
<220> FEATURE:
<223> OTHER INFORMATION: Primer

<400> SEQUENCE: 120
cgatgttccg gcgctgtgcc act                                            23

<210> SEQ ID NO 121
<211> LENGTH: 23
<212> TYPE: DNA
<213> ORGANISM: Artificial Sequence
<220> FEATURE:
<223> OTHER INFORMATION: Primer

<400> SEQUENCE: 121
agtggcacag cgccggaaca tcg                                            23

<210> SEQ ID NO 122
<211> LENGTH: 23
<212> TYPE: DNA
<213> ORGANISM: Artificial Sequence
<220> FEATURE:
<223> OTHER INFORMATION: Primer

<400> SEQUENCE: 122
cgatgttccg gtgctgtgcc act                                            23

<210> SEQ ID NO 123
<211> LENGTH: 23
<212> TYPE: DNA
<213> ORGANISM: Artificial Sequence
<220> FEATURE:
<223> OTHER INFORMATION: Primer

<400> SEQUENCE: 123
agtggcacag caccggaaca tcg                                            23

<210> SEQ ID NO 124
<211> LENGTH: 23
<212> TYPE: DNA
<213> ORGANISM: Artificial Sequence
<220> FEATURE:
<223> OTHER INFORMATION: Primer

<400> SEQUENCE: 124
cgatgttccg ctgctgtgcc act                                            23

<210> SEQ ID NO 125
<211> LENGTH: 23
<212> TYPE: DNA
<213> ORGANISM: Artificial Sequence
<220> FEATURE:
<223> OTHER INFORMATION: Primer

<400> SEQUENCE: 125
agtggcacag cagcggaaca tcg                                            23

<210> SEQ ID NO 126
<211> LENGTH: 23
<212> TYPE: DNA
<213> ORGANISM: Artificial Sequence
<220> FEATURE:
<223> OTHER INFORMATION: Primer

<400> SEQUENCE: 126
```
cgatgttccg attctgtgcc act                                              23

<210> SEQ ID NO 127
<211> LENGTH: 23
<212> TYPE: DNA
<213> ORGANISM: Artificial Sequence
<220> FEATURE:
<223> OTHER INFORMATION: Primer

<400> SEQUENCE: 127
agtggcacag aatcggaaca tcg                                              23

<210> SEQ ID NO 128
<211> LENGTH: 23
<212> TYPE: DNA
<213> ORGANISM: Artificial Sequence
<220> FEATURE:
<223> OTHER INFORMATION: Primer

<400> SEQUENCE: 128
cgatgttccg ccgctgtgcc act                                              23

<210> SEQ ID NO 129
<211> LENGTH: 23
<212> TYPE: DNA
<213> ORGANISM: Artificial Sequence
<220> FEATURE:
<223> OTHER INFORMATION: Primer

<400> SEQUENCE: 129
agtggcacag cggcggaaca tcg                                              23

<210> SEQ ID NO 130
<211> LENGTH: 23
<212> TYPE: DNA
<213> ORGANISM: Artificial Sequence
<220> FEATURE:
<223> OTHER INFORMATION: Primer

<400> SEQUENCE: 130
cgatgttccg tgcctgtgcc act                                              23

<210> SEQ ID NO 131
<211> LENGTH: 23
<212> TYPE: DNA
<213> ORGANISM: Artificial Sequence
<220> FEATURE:
<223> OTHER INFORMATION: Primer

<400> SEQUENCE: 131
agtggcacag gcacggaaca tcg                                              23

<210> SEQ ID NO 132
<211> LENGTH: 23
<212> TYPE: DNA
<213> ORGANISM: Artificial Sequence
<220> FEATURE:
<223> OTHER INFORMATION: Primer

<400> SEQUENCE: 132
cgatgttccg tatctgtgcc act                                              23

<210> SEQ ID NO 133
<211> LENGTH: 23
<212> TYPE: DNA
<213> ORGANISM: Artificial Sequence
<220> FEATURE:

-continued

<223> OTHER INFORMATION: Primer

<400> SEQUENCE: 133
agtggcacag atacggaaca tcg                 23

<210> SEQ ID NO 134
<211> LENGTH: 23
<212> TYPE: DNA
<213> ORGANISM: Artificial Sequence
<220> FEATURE:
<223> OTHER INFORMATION: Primer

<400> SEQUENCE: 134
cgatgttccg tggctgtgcc act                 23

<210> SEQ ID NO 135
<211> LENGTH: 23
<212> TYPE: DNA
<213> ORGANISM: Artificial Sequence
<220> FEATURE:
<223> OTHER INFORMATION: Primer

<400> SEQUENCE: 135
agtggcacag ccacggaaca tcg                 23

<210> SEQ ID NO 136
<211> LENGTH: 23
<212> TYPE: DNA
<213> ORGANISM: Artificial Sequence
<220> FEATURE:
<223> OTHER INFORMATION: Primer

<400> SEQUENCE: 136
cgatgttccg agcctgtgcc act                 23

<210> SEQ ID NO 137
<211> LENGTH: 23
<212> TYPE: DNA
<213> ORGANISM: Artificial Sequence
<220> FEATURE:
<223> OTHER INFORMATION: Primer

<400> SEQUENCE: 137
agtggcacag gctcggaaca tcg                 23

<210> SEQ ID NO 138
<211> LENGTH: 23
<212> TYPE: DNA
<213> ORGANISM: Artificial Sequence
<220> FEATURE:
<223> OTHER INFORMATION: Primer

<400> SEQUENCE: 138
cgatgttccg accctgtgcc act                 23

<210> SEQ ID NO 139
<211> LENGTH: 23
<212> TYPE: DNA
<213> ORGANISM: Artificial Sequence
<220> FEATURE:
<223> OTHER INFORMATION: Primer

<400> SEQUENCE: 139
agtggcacag ggtcggaaca tcg                 23

<210> SEQ ID NO 140

```
<211> LENGTH: 23
<212> TYPE: DNA
<213> ORGANISM: Artificial Sequence
<220> FEATURE:
<223> OTHER INFORMATION: Primer

<400> SEQUENCE: 140
cgatgttccg cagctgtgcc act                                              23

<210> SEQ ID NO 141
<211> LENGTH: 23
<212> TYPE: DNA
<213> ORGANISM: Artificial Sequence
<220> FEATURE:
<223> OTHER INFORMATION: Primer

<400> SEQUENCE: 141
agtggcacag ctgcggaaca tcg                                              23

<210> SEQ ID NO 142
<211> LENGTH: 23
<212> TYPE: DNA
<213> ORGANISM: Artificial Sequence
<220> FEATURE:
<223> OTHER INFORMATION: Primer

<400> SEQUENCE: 142
cgatgttccg aacctgtgcc act                                              23

<210> SEQ ID NO 143
<211> LENGTH: 23
<212> TYPE: DNA
<213> ORGANISM: Artificial Sequence
<220> FEATURE:
<223> OTHER INFORMATION: Primer

<400> SEQUENCE: 143
agtggcacag gttcggaaca tcg                                              23

<210> SEQ ID NO 144
<211> LENGTH: 23
<212> TYPE: DNA
<213> ORGANISM: Artificial Sequence
<220> FEATURE:
<223> OTHER INFORMATION: Primer

<400> SEQUENCE: 144
cgatgttccg gatctgtgcc act                                              23

<210> SEQ ID NO 145
<211> LENGTH: 23
<212> TYPE: DNA
<213> ORGANISM: Artificial Sequence
<220> FEATURE:
<223> OTHER INFORMATION: Primer

<400> SEQUENCE: 145
agtggcacag atccggaaca tcg                                              23

<210> SEQ ID NO 146
<211> LENGTH: 23
<212> TYPE: DNA
<213> ORGANISM: Artificial Sequence
<220> FEATURE:
<223> OTHER INFORMATION: Primer

<400> SEQUENCE: 146
```
cgatgttccg gaactgtgcc act                                              23

<210> SEQ ID NO 147
<211> LENGTH: 23
<212> TYPE: DNA
<213> ORGANISM: Artificial Sequence
<220> FEATURE:
<223> OTHER INFORMATION: Primer

<400> SEQUENCE: 147
agtggcacag ttccggaaca tcg                                              23

<210> SEQ ID NO 148
<211> LENGTH: 23
<212> TYPE: DNA
<213> ORGANISM: Artificial Sequence
<220> FEATURE:
<223> OTHER INFORMATION: Primer

<400> SEQUENCE: 148
cgatgttccg cgtctgtgcc act                                              23

<210> SEQ ID NO 149
<211> LENGTH: 23
<212> TYPE: DNA
<213> ORGANISM: Artificial Sequence
<220> FEATURE:
<223> OTHER INFORMATION: Primer

<400> SEQUENCE: 149
agtggcacag acgcggaaca tcg                                              23

<210> SEQ ID NO 150
<211> LENGTH: 23
<212> TYPE: DNA
<213> ORGANISM: Artificial Sequence
<220> FEATURE:
<223> OTHER INFORMATION: Primer

<400> SEQUENCE: 150
cgatgttccg catctgtgcc act                                              23

<210> SEQ ID NO 151
<211> LENGTH: 23
<212> TYPE: DNA
<213> ORGANISM: Artificial Sequence
<220> FEATURE:
<223> OTHER INFORMATION: Primer

<400> SEQUENCE: 151
agtggcacag atgcggaaca tcg                                              23

<210> SEQ ID NO 152
<211> LENGTH: 23
<212> TYPE: DNA
<213> ORGANISM: Artificial Sequence
<220> FEATURE:
<223> OTHER INFORMATION: Primer

<400> SEQUENCE: 152
cgatgttccg aaactgtgcc act                                              23

<210> SEQ ID NO 153
<211> LENGTH: 23
<212> TYPE: DNA
<213> ORGANISM: Artificial Sequence
<220> FEATURE:

<223> OTHER INFORMATION: Primer

<400> SEQUENCE: 153
agtggcacag tttcggaaca tcg 23

<210> SEQ ID NO 154
<211> LENGTH: 23
<212> TYPE: DNA
<213> ORGANISM: Artificial Sequence
<220> FEATURE:
<223> OTHER INFORMATION: Primer

<400> SEQUENCE: 154
cgatgttccg atgctgtgcc act 23

<210> SEQ ID NO 155
<211> LENGTH: 23
<212> TYPE: DNA
<213> ORGANISM: Artificial Sequence
<220> FEATURE:
<223> OTHER INFORMATION: Primer

<400> SEQUENCE: 155
agtggcacag catcggaaca tcg 23

<210> SEQ ID NO 156
<211> LENGTH: 23
<212> TYPE: DNA
<213> ORGANISM: Artificial Sequence
<220> FEATURE:
<223> OTHER INFORMATION: Primer

<400> SEQUENCE: 156
cattggttac ggcggtggcc gtg 23

<210> SEQ ID NO 157
<211> LENGTH: 23
<212> TYPE: DNA
<213> ORGANISM: Artificial Sequence
<220> FEATURE:
<223> OTHER INFORMATION: Primer

<400> SEQUENCE: 157
cacggccacc ggcgtaacca atg 23

<210> SEQ ID NO 158
<211> LENGTH: 23
<212> TYPE: DNA
<213> ORGANISM: Artificial Sequence
<220> FEATURE:
<223> OTHER INFORMATION: Primer

<400> SEQUENCE: 158
cattggttac gcgggtggcc gtg 23

<210> SEQ ID NO 159
<211> LENGTH: 23
<212> TYPE: DNA
<213> ORGANISM: Artificial Sequence
<220> FEATURE:
<223> OTHER INFORMATION: Primer

<400> SEQUENCE: 159
cacggccacc gcggtaacca atg 23

<210> SEQ ID NO 160

```
<211> LENGTH: 23
<212> TYPE: DNA
<213> ORGANISM: Artificial Sequence
<220> FEATURE:
<223> OTHER INFORMATION: Primer

<400> SEQUENCE: 160
cattggttac gtgggtggcc gtg                                              23

<210> SEQ ID NO 161
<211> LENGTH: 23
<212> TYPE: DNA
<213> ORGANISM: Artificial Sequence
<220> FEATURE:
<223> OTHER INFORMATION: Primer

<400> SEQUENCE: 161
cacggccacc gtggtaacca atg                                              23

<210> SEQ ID NO 162
<211> LENGTH: 23
<212> TYPE: DNA
<213> ORGANISM: Artificial Sequence
<220> FEATURE:
<223> OTHER INFORMATION: Primer

<400> SEQUENCE: 162
cattggttac ctgggtggcc gtg                                              23

<210> SEQ ID NO 163
<211> LENGTH: 23
<212> TYPE: DNA
<213> ORGANISM: Artificial Sequence
<220> FEATURE:
<223> OTHER INFORMATION: Primer

<400> SEQUENCE: 163
cacggccacc ctggtaacca atg                                              23

<210> SEQ ID NO 164
<211> LENGTH: 23
<212> TYPE: DNA
<213> ORGANISM: Artificial Sequence
<220> FEATURE:
<223> OTHER INFORMATION: Primer

<400> SEQUENCE: 164
cattggttac attggtggcc gtg                                              23

<210> SEQ ID NO 165
<211> LENGTH: 23
<212> TYPE: DNA
<213> ORGANISM: Artificial Sequence
<220> FEATURE:
<223> OTHER INFORMATION: Primer

<400> SEQUENCE: 165
cacggccacc attgtaacca atg                                              23

<210> SEQ ID NO 166
<211> LENGTH: 23
<212> TYPE: DNA
<213> ORGANISM: Artificial Sequence
<220> FEATURE:
<223> OTHER INFORMATION: Primer

<400> SEQUENCE: 166
```

```
cattggttac ccgggtggcc gtg                                              23

<210> SEQ ID NO 167
<211> LENGTH: 23
<212> TYPE: DNA
<213> ORGANISM: Artificial Sequence
<220> FEATURE:
<223> OTHER INFORMATION: Primer

<400> SEQUENCE: 167
cacggccacc ccggtaacca atg                                              23

<210> SEQ ID NO 168
<211> LENGTH: 23
<212> TYPE: DNA
<213> ORGANISM: Artificial Sequence
<220> FEATURE:
<223> OTHER INFORMATION: Primer

<400> SEQUENCE: 168
cattggttac tgcggtggcc gtg                                              23

<210> SEQ ID NO 169
<211> LENGTH: 23
<212> TYPE: DNA
<213> ORGANISM: Artificial Sequence
<220> FEATURE:
<223> OTHER INFORMATION: Primer

<400> SEQUENCE: 169
cacggccacc tgcgtaacca atg                                              23

<210> SEQ ID NO 170
<211> LENGTH: 23
<212> TYPE: DNA
<213> ORGANISM: Artificial Sequence
<220> FEATURE:
<223> OTHER INFORMATION: Primer

<400> SEQUENCE: 170
cattggttac tatggtggcc gtg                                              23

<210> SEQ ID NO 171
<211> LENGTH: 23
<212> TYPE: DNA
<213> ORGANISM: Artificial Sequence
<220> FEATURE:
<223> OTHER INFORMATION: Primer

<400> SEQUENCE: 171
cacggccacc tatgtaacca atg                                              23

<210> SEQ ID NO 172
<211> LENGTH: 23
<212> TYPE: DNA
<213> ORGANISM: Artificial Sequence
<220> FEATURE:
<223> OTHER INFORMATION: Primer

<400> SEQUENCE: 172
cattggttac tggggtggcc gtg                                              23

<210> SEQ ID NO 173
<211> LENGTH: 23
<212> TYPE: DNA
<213> ORGANISM: Artificial Sequence
<220> FEATURE:
```

```
<223> OTHER INFORMATION: Primer

<400> SEQUENCE: 173
cacggccacc tgggtaacca atg                                          23

<210> SEQ ID NO 174
<211> LENGTH: 23
<212> TYPE: DNA
<213> ORGANISM: Artificial Sequence
<220> FEATURE:
<223> OTHER INFORMATION: Primer

<400> SEQUENCE: 174
cattggttac agcggtggcc gtg                                          23

<210> SEQ ID NO 175
<211> LENGTH: 23
<212> TYPE: DNA
<213> ORGANISM: Artificial Sequence
<220> FEATURE:
<223> OTHER INFORMATION: Primer

<400> SEQUENCE: 175
cacggccacc agcgtaacca atg                                          23

<210> SEQ ID NO 176
<211> LENGTH: 23
<212> TYPE: DNA
<213> ORGANISM: Artificial Sequence
<220> FEATURE:
<223> OTHER INFORMATION: Primer

<400> SEQUENCE: 176
cattggttac accggtggcc gtg                                          23

<210> SEQ ID NO 177
<211> LENGTH: 23
<212> TYPE: DNA
<213> ORGANISM: Artificial Sequence
<220> FEATURE:
<223> OTHER INFORMATION: Primer

<400> SEQUENCE: 177
cacggccacc accgtaacca atg                                          23

<210> SEQ ID NO 178
<211> LENGTH: 23
<212> TYPE: DNA
<213> ORGANISM: Artificial Sequence
<220> FEATURE:
<223> OTHER INFORMATION: Primer

<400> SEQUENCE: 178
cattggttac cagggtggcc gtg                                          23

<210> SEQ ID NO 179
<211> LENGTH: 23
<212> TYPE: DNA
<213> ORGANISM: Artificial Sequence
<220> FEATURE:
<223> OTHER INFORMATION: Primer

<400> SEQUENCE: 179
cacggccacc caggtaacca atg                                          23

<210> SEQ ID NO 180
```

```
<211> LENGTH: 23
<212> TYPE: DNA
<213> ORGANISM: Artificial Sequence
<220> FEATURE:
<223> OTHER INFORMATION: Primer

<400> SEQUENCE: 180
cattggttac tttggtggcc gtg                                    23

<210> SEQ ID NO 181
<211> LENGTH: 23
<212> TYPE: DNA
<213> ORGANISM: Artificial Sequence
<220> FEATURE:
<223> OTHER INFORMATION: Primer

<400> SEQUENCE: 181
cacggccacc tttgtaacca atg                                    23

<210> SEQ ID NO 182
<211> LENGTH: 23
<212> TYPE: DNA
<213> ORGANISM: Artificial Sequence
<220> FEATURE:
<223> OTHER INFORMATION: Primer

<400> SEQUENCE: 182
cattggttac gatggtggcc gtg                                    23

<210> SEQ ID NO 183
<211> LENGTH: 23
<212> TYPE: DNA
<213> ORGANISM: Artificial Sequence
<220> FEATURE:
<223> OTHER INFORMATION: Primer

<400> SEQUENCE: 183
cacggccacc gatgtaacca atg                                    23

<210> SEQ ID NO 184
<211> LENGTH: 23
<212> TYPE: DNA
<213> ORGANISM: Artificial Sequence
<220> FEATURE:
<223> OTHER INFORMATION: Primer

<400> SEQUENCE: 184
cattggttac gaaggtggcc gtg                                    23

<210> SEQ ID NO 185
<211> LENGTH: 23
<212> TYPE: DNA
<213> ORGANISM: Artificial Sequence
<220> FEATURE:
<223> OTHER INFORMATION: Primer

<400> SEQUENCE: 185
cacggccacc gaagtaacca atg                                    23

<210> SEQ ID NO 186
<211> LENGTH: 23
<212> TYPE: DNA
<213> ORGANISM: Artificial Sequence
<220> FEATURE:
<223> OTHER INFORMATION: Primer

<400> SEQUENCE: 186
```
cattggttac cgtggtggcc gtg 23

<210> SEQ ID NO 187
<211> LENGTH: 23
<212> TYPE: DNA
<213> ORGANISM: Artificial Sequence
<220> FEATURE:
<223> OTHER INFORMATION: Primer

<400> SEQUENCE: 187
cacggccacc cgtgtaacca atg 23

<210> SEQ ID NO 188
<211> LENGTH: 23
<212> TYPE: DNA
<213> ORGANISM: Artificial Sequence
<220> FEATURE:
<223> OTHER INFORMATION: Primer

<400> SEQUENCE: 188
cattggttac catggtggcc gtg 23

<210> SEQ ID NO 189
<211> LENGTH: 23
<212> TYPE: DNA
<213> ORGANISM: Artificial Sequence
<220> FEATURE:
<223> OTHER INFORMATION: Primer

<400> SEQUENCE: 189
cacggccacc catgtaacca atg 23

<210> SEQ ID NO 190
<211> LENGTH: 23
<212> TYPE: DNA
<213> ORGANISM: Artificial Sequence
<220> FEATURE:
<223> OTHER INFORMATION: Primer

<400> SEQUENCE: 190
cattggttac aaaggtggcc gtg 23

<210> SEQ ID NO 191
<211> LENGTH: 23
<212> TYPE: DNA
<213> ORGANISM: Artificial Sequence
<220> FEATURE:
<223> OTHER INFORMATION: Primer

<400> SEQUENCE: 191
cacggccacc aaagtaacca atg 23

<210> SEQ ID NO 192
<211> LENGTH: 23
<212> TYPE: DNA
<213> ORGANISM: Artificial Sequence
<220> FEATURE:
<223> OTHER INFORMATION: Primer

<400> SEQUENCE: 192
cattggttac atgggtggcc gtg 23

<210> SEQ ID NO 193
<211> LENGTH: 23
<212> TYPE: DNA
<213> ORGANISM: Artificial Sequence
<220> FEATURE:

<223> OTHER INFORMATION: Primer

<400> SEQUENCE: 193
cacggccacc atggtaacca atg                                              23

<210> SEQ ID NO 194
<211> LENGTH: 23
<212> TYPE: DNA
<213> ORGANISM: Artificial Sequence
<220> FEATURE:
<223> OTHER INFORMATION: Primer

<400> SEQUENCE: 194
ggacaacatc gtgcctcctt cta                                              23

<210> SEQ ID NO 195
<211> LENGTH: 23
<212> TYPE: DNA
<213> ORGANISM: Artificial Sequence
<220> FEATURE:
<223> OTHER INFORMATION: Primer

<400> SEQUENCE: 195
tagaaggagg cacgatgttg tcc                                              23

<210> SEQ ID NO 196
<211> LENGTH: 23
<212> TYPE: DNA
<213> ORGANISM: Artificial Sequence
<220> FEATURE:
<223> OTHER INFORMATION: Primer

<400> SEQUENCE: 196
ggacaacatc gcgcctcctt cta                                              23

<210> SEQ ID NO 197
<211> LENGTH: 23
<212> TYPE: DNA
<213> ORGANISM: Artificial Sequence
<220> FEATURE:
<223> OTHER INFORMATION: Primer

<400> SEQUENCE: 197
tagaaggagg cgcgatgttg tcc                                              23

<210> SEQ ID NO 198
<211> LENGTH: 23
<212> TYPE: DNA
<213> ORGANISM: Artificial Sequence
<220> FEATURE:
<223> OTHER INFORMATION: Primer

<400> SEQUENCE: 198
ggacaacatc tcacctcctt cta                                              23

<210> SEQ ID NO 199
<211> LENGTH: 23
<212> TYPE: DNA
<213> ORGANISM: Artificial Sequence
<220> FEATURE:
<223> OTHER INFORMATION: Primer

<400> SEQUENCE: 199
tagaaggagg tgagatgttg tcc                                              23

<210> SEQ ID NO 200

```
<211> LENGTH: 23
<212> TYPE: DNA
<213> ORGANISM: Artificial Sequence
<220> FEATURE:
<223> OTHER INFORMATION: Primer

<400> SEQUENCE: 200
ggacaacatc acccctcctt cta                                             23

<210> SEQ ID NO 201
<211> LENGTH: 23
<212> TYPE: DNA
<213> ORGANISM: Artificial Sequence
<220> FEATURE:
<223> OTHER INFORMATION: Primer

<400> SEQUENCE: 201
tagaaggagg ggtgatgttg tcc                                             23

<210> SEQ ID NO 202
<211> LENGTH: 326
<212> TYPE: PRT
<213> ORGANISM: Thermotoga lettingae

<400> SEQUENCE: 202

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Gly Arg
                85                  90                  95

Gly Phe Pro Tyr Asp Trp Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
        195                 200                 205

Cys Asp Val Pro Phe Leu Cys His Tyr Lys Arg Ala Val Gln Ile Thr
    210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270
```

```
Met Asp Asp Ile Cys Pro Pro Ser Thr Val Phe Ala Ala Tyr Asn Tyr
            275                 280                 285

Tyr Ala Gly Glu Lys Asp Ile Arg Ile Tyr Pro Tyr Asn Asn His Glu
        290                 295                 300

Gly Gly Gly Ser Phe His Thr Leu Glu Lys Leu Lys Phe Val Lys Lys
305                 310                 315                 320

Thr Ile Ser Met Arg Glu
                325

<210> SEQ ID NO 203
<211> LENGTH: 325
<212> TYPE: PRT
<213> ORGANISM: Thermotoga petrophilia

<400> SEQUENCE: 203

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320
```

Leu Phe Glu Lys Gly
            325

<210> SEQ ID NO 204
<211> LENGTH: 325
<212> TYPE: PRT
<213> ORGANISM: Thermotoga sp. RQ2

<400> SEQUENCE: 204

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Lys Gly
            325

<210> SEQ ID NO 205
<211> LENGTH: 329
<212> TYPE: PRT
<213> ORGANISM: Thermotoga sp. RQ2

<400> SEQUENCE: 205

```
Met Ala Leu Phe Asp Met Pro Leu Glu Lys Leu Arg Ser Tyr Leu Pro
1               5                   10                  15

Asp Arg Tyr Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp
            35                  40                  45

Tyr Leu Leu Glu Asn Val Glu Val Tyr Asp Val Thr Phe Ser Gly Tyr
        50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly
                85                  90                  95

Arg Gly Phe Pro Phe Asp Trp Leu Phe Trp Ser Ser Ala Gly Tyr Ala
                100                 105                 110

His Phe Val Met Asp Thr Arg Gly Gln Gly Thr Ser Arg Val Lys Gly
            115                 120                 125

Asp Thr Pro Asp Tyr Cys Asp Glu Pro Ile Asn Pro Gln Phe Pro Gly
        130                 135                 140

Phe Met Thr Arg Gly Ile Leu Asp Pro Arg Thr Tyr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
                180                 185                 190

Gly Ile Ala Leu Ala Val Ala Ala Leu Ser Glu Ile Pro Lys Ala Leu
            195                 200                 205

Val Ser Asn Val Pro Phe Leu Cys His Phe Arg Arg Ala Val Gln Ile
        210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
                260                 265                 270

Leu Met Asp Lys Thr Cys Pro Pro Ser Thr Val Phe Ala Ala Tyr Asn
            275                 280                 285

His Tyr Ala Gly Pro Lys Glu Ile Lys Val Tyr Pro Phe Asn Glu His
        290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325
```

<210> SEQ ID NO 206
<211> LENGTH: 50
<212> TYPE: DNA
<213> ORGANISM: artificial sequence
<220> FEATURE:
<223> OTHER INFORMATION: primer

<400> SEQUENCE: 206
taactgcagt aaggaggaat aggacatggc cttcttcgat ttacccactc    50

<210> SEQ ID NO 207

```
<211> LENGTH: 38
<212> TYPE: DNA
<213> ORGANISM: artificial sequence
<220> FEATURE:
<223> OTHER INFORMATION: primer

<400> SEQUENCE: 207
tgatctagat tagcctttct caaatagttt tttcaaga                            38

<210> SEQ ID NO 208
<211> LENGTH: 1012
<212> TYPE: DNA
<213> ORGANISM: Thermotoga maritima

<400> SEQUENCE: 208
taactgcagt aaggaggaat aggacatggc cttcttcgat ttaccactcg aagaactgaa    60
gaaatatcgt ccagagcggt acgaagagaa agacttcgat gagttctggg aagagacact   120
cgcagagagc gaaaagttcc ccttagaccc cgtcttcgag aggatggagt ctcacctcaa   180
aacagtcgaa gcgtacgatg tcaccttctc cggatacagg ggacagagga tcaaagggtg   240
gctccttgtt ccaaaactgg aagaagaaaa acttccctgc gttgtgcagt acataggata   300
caacggtgga agaggattcc ctcacgactg gctgttctgg ccttctatgg gttacatatg   360
tttcgtcatg gatactcgag gtcagggaag cggctggctg aaaggagaca caccggatta   420
ccctgagggt cccgttgacc ctcagtatcc aggattcatg acaagaggaa tactggatcc   480
cagaacttac tactacagac gagtcttcac ggacgctgtc agagccgttg aagctgctgc   540
ttcttttcct caggtagatc aagaaagaat cgtgatagct ggaggcagtc agggtggcgg   600
aatagccctt gcggtgagcg ctctctcaaa gaaagcaaag gctcttctgt gcgatgtgcc   660
gtttctgtgt cacttcagaa gagcagtaca gcttgtggat acgcatccat acgcggagat   720
cacgaacttt ctaaagaccc acagagacaa ggaagaaatc gtgttcagga ctctttccta   780
tttcgatgga gtgaacttcg cagccagagc gaagatccct gcgctgtttt ctgtgggtct   840
catggacaac atttgtcctc cttcaacggt tttcgctgcc tacaattact acgctggacc   900
gaaggaaatc agaatctatc cgtacaacaa ccacgaggga ggaggctctt tccaagcggt   960
tgaacaggtg aaattcttga aaaaactatt tgagaaaggc taatctagat ca          1012
```